US006713580B2

(12) United States Patent
Johnson et al.

(10) Patent No.: US 6,713,580 B2
(45) Date of Patent: Mar. 30, 2004

(54) QUATERNARY AMINO ACIDS ON SOLID SUPPORTS

(75) Inventors: Michael Johnson, Greensboro, NC (US); Keqiang Li, Greensboro, NC (US); Elso DiFranco, Greensboro, NC (US); Daljit S. Dhanoa, Wakefield, MA (US)

(73) Assignee: Pharmacore, Inc., High Point, NC (US)

( * ) Notice: Subject to any disclaimer, the term of this patent is extended or adjusted under 35 U.S.C. 154(b) by 0 days.

(21) Appl. No.: 10/008,953

(22) Filed: Dec. 6, 2001

(65) Prior Publication Data

US 2002/0086949 A1 Jul. 4, 2002

Related U.S. Application Data

(60) Provisional application No. 60/251,728, filed on Dec. 6, 2000.

(51) Int. Cl.$^7$ .............................. C08F 2/00; C08L 89/00; A61K 38/00; C07K 7/00; C07K 38/00
(52) U.S. Cl. .................... 526/199; 525/54.1; 525/54.11; 525/348; 525/374; 525/375; 525/380; 525/386; 514/9; 530/300; 530/317; 530/333; 530/334; 530/335
(58) Field of Search ............................ 526/199; 525/54.1, 525/54.11, 348, 374, 375, 380, 386; 514/9; 530/300, 317, 333, 334, 335

(56) References Cited

U.S. PATENT DOCUMENTS

| | | | |
|---|---|---|---|
| 4,535,167 A | 8/1985 | Freidinger et al. | |
| 4,631,211 A | 12/1986 | Houghten | |
| 4,757,153 A | 7/1988 | Hansen, Jr. et al. | |
| 5,280,093 A | 1/1994 | Jacquier et al. | |
| 5,545,568 A | 8/1996 | Ellman et al. | |
| 6,025,371 A | 2/2000 | Gordeev et al. | |
| 6,117,940 A | 9/2000 | Mjalli | |
| 6,121,054 A | 9/2000 | Lebl | |
| 6,124,462 A | 9/2000 | Li | |
| 6,207,861 B1 | 3/2001 | Nash et al. | |

FOREIGN PATENT DOCUMENTS

WO   WO 01/83575 A1   11/2001

OTHER PUBLICATIONS

PCT International Search Report for PCT/US 01/46585 mailed Mar. 5, 2003.
Boojamra et al. "An expedient and high–yielding method for the solid–phase synthesis of diverse 1,4–benzodiazapine–2, 5–diones" J. Org. Chem. 60:5742–5743 (1995).
Bunin et al., "The combinatorial synthesis and chemical and biological evaluation of a 1,4–benzodiazepine library" Proc. Natl. Acad. Sci. USA 91:4708–4712 (1994).
Cao, X. et al., "Synthesis of NH–acyl–α–aminoamides on rink resin: inhibitors of the hematopoietic protein tyrosine phosphatase" Bioorg. Med. Chem. Lett., vol. 5, 1995, 2953–2958.
Demharter, A. et al. Synthesis of Chiral 1,1'—Iminodicarboxylic Acid Derivatives from—α Amino Acids Aldehydes, Isocyanides, and Alcohols by the Diastereoselective Five–Center–Four–Component Reactron. Angew. Chem. Int. Ed. Engl. 35: 173–175 (1996).
Dressman et al. "Solid phase synthesis of hydantions using a carbamate linker and a novel cyclization/cleavage step" Tetrahedron Lett. 37:937–940 (1996).
Faust, "Geminal Benzotriazolyl Ethoxy derivatives–Efficient auxiliaries in the synthesis of unsaturated carbonyl compounds", J. Prakt. Chem., 1997, vol. 339, p. 98–100.
Geysen et al., "Use of peptide synthesis to probe viral antigens for epitopes to a resolution of a single amino acid" Proc. Natl. Acad. Sci. USA 81:3998–4002 (1984).
Gordon et al., "Applications of combinatorial technologies to drug discovery. 2. Combinatorial organic synthesis, library screening strategies, and future directions" J. Med. Chem. 37:1385–1401 (1994).
Grant, G.A., ed., "Synthetic Peptides. A User's Guide" Oxford Press. A title page and table of contents. 2002.
Greene, T.W., "Protection for the Amino Group" Protective Groups in Organic Synthesis, John Wiley & Sons, New York, NY, Chapter 7 (1981).
Hermkens et al., "Solid–phase organic reactions: A review of the recent literature" Tetrahedron 52:4527–4554 (1996).
Keating, et al., "Molecular diversity via a convertible isocyanide in the Ugi four component condensation" J. Am. Chem. Soc. 1995, vol. 117, 7842–7843.
Keating, T.A. et al. "Postcondensation Modifications of Ugi Four–Component Products: 1–Isocyanocyclohexene as a convertible Isocyanide Mechanism of Conversion, Synthesis of Diverse Structures, and Demonstration of Resin Capture". J. Am. Chem. Soc. 1996, vol. 118, No. 11,pp 2574–2583.
Kitaguchi et al."Enzymatic formation of an isopeptide bond involving the ϵ–amino group of lysine" Tetrahedron Lett., 1988, vol. 29, pp. 5487–5488.
Kunz, H. et al. "Carbohydrates as chiral templates: diastereoselective Ugi synthesis of (S) amino acids using o–acylated d–arabinopyranosylamine as the auxiliary" Tetrahedron, Lett., 1989, vol. 30, pp. 4109–4110.

(List continued on next page.)

Primary Examiner—James J. Seidleck
Assistant Examiner—Olga Asinovsky
(74) Attorney, Agent, or Firm—Kilpatrick Stockton LLP; Charles W. Calkins

(57) ABSTRACT

The present invention relates to novel templates useful for generating novel compounds and to compounds produced utilizing the templates. The templates comprise quaternary amino acids that may be linked to solid supports. These templates make possible the production of novel classes of chemical compounds through a plurality of chemical reactions. The templates are advantageous for use in drug discovery regimes.

67 Claims, 8 Drawing Sheets-

OTHER PUBLICATIONS

Linderman, "Enhanced diastereoselectivity in the asymmetric Ugi reaction using a new convertible isonitrile" J. Org. Chem., 1999, vol. 64, pp. 336–337.

Marshall et al., "Phosphorodithioate DNA as a potential therapeutic drug" Science 259:1564–1570 (1993).

Merrifield, "Solid phase peptide synthsis. I. The synthesis of a tetrapeptide" J. Am. Chem. Soc. 85:2149–2154 (1963).

Mjalli, et al., "Solid phase synthesis of pyrroles derived from a four component condensation" Tetrahedron Lett., 1996, vol. 37, pp. 2943–2946.

Plunkett et al. "Solid–phase synthesis of structurally diverse 1.4–benzodiazapine derivatives using the Stille coupling reaction" J. Am. Chem. Soc. 117:3306–3307 (1995).

Siglmüller et al. "Chiral ferrocenylalkylamines from (–)–menthone" Tetrahedron, 1986, vol. 42, pp. 5931–5940.

Ugi, I., Isonitrile Chemistry, p. 1, Academic Press, New York and London, 1971.

Ugi, I., "From Isocyanides via four–component condensations to antibiotic syntheses" Angew Chem., Int. Ed. Engl., 1982, vol. 21, pp. 810–819.

Ugi, I., "Perspektiven von Multikomponentenreaktionen und deren Bibliotheken" J. Prakt. Chem., 1997, Vol, 339, p. 499–516.

Z = Wang resin

Z = Wang Resin

Z = Wang Resin

Z = Wang resin

Z = Merrifield resin

Z = Merrifield resin

Z = Merrifield resin

Z = Merrifield resin

QUATERNARY AMINO ACIDS ON SOLID SUPPORTS

STATEMENT OF RELATED APPLICATIONS

The present application claims priority under 35 USC 119 from U.S. Provisional Application Ser. No. 60/251,728 filed Dec. 6, 2000, entitled "Quaternary Amino Acids on Solid Supports" the disclosure of which is incorporated herein by reference.

FIELD OF THE INVENTION

The present invention relates to novel templates useful for generating novel compounds and to compounds produced utilizing the templates. The templates comprise quaternary amino acids that may be linked to solid supports. These templates make possible the production of novel classes of chemical compounds through a plurality of chemical reactions. The templates are advantageous for use in drug discovery regimes.

BACKGROUND OF THE INVENTION

The use of solid phase synthesis techniques for the synthesis of polypeptides and oligonucleotides is known. More recently, the use of solid phase techniques for the synthesis of small organic molecules has become a major focus of research. Of prime importance has been the ability of solid phase techniques to be automated, with an attendant increase in compound throughput and efficiency in research. This has been exploited with great vigor in the area of pharmaceutical research where it has been estimated that 10,000 compounds must be synthesized and tested in order to find one new drug (*Science* 259:1564, (1993)). The focus on combinatorial chemistry techniques to increase compound throughput has now become almost universal in the pharmaceutical and agricultural industries.

An additional aspect of combinatorial chemistry relates to the chemical diversity of the compound stocks that are available for screening by the pharmaceutical companies in the search for new lead structures. These have tended to be limited to the classes of compounds previously investigated through medicinal chemical techniques within each company. Therefore, the availability of new classes of molecules for screening has become a major need.

As a consequence of the development of efficient automation equipment and processes, parallel synthesis techniques have become the most extensively used method in combinatorial chemistry. The field of pharmaceutical and agricultural research has a strong need for highly flexible technologies and chemical building blocks with and without the polymer support to generate a large number of novel classes of compounds for screening and clinical testing.

Thus, templates such as those presented in the present invention are highly desirable and valuable, in particular in the synthesis of peptides and of amino acid containing compounds for drug discovery.

SUMMARY OF THE INVENTION

The present invention provides support templates that may be utilized to generate novel compounds. The support templates comprise amino acids that may be linked to polymeric supports to form a platform for chemical discovery.

In general terms the present invention provides quaternary amino acids that are capable of being used as templates for the synthesis of other molecules including peptides, other amino acids, and other compounds that may be useful in pharmaceutical, agricultural, food product and/or related settings. The quaternary amino acids may be linked to a solid support to form a template that may be utilized in solid phase synthesis techniques that advantageously permit compounds with intermediates relatively unstable to other techniques to be synthesized and isolated. Embodiments of the present invention may be utilized in combinatorial chemistry using parallel synthesis techniques to create and screen large libraries of potentially useful compounds.

Details and embodiments of the present invention are set forth below and in the appended drawings.

DETAILED DESCRIPTION OF THE INVENTION

Figure 1:
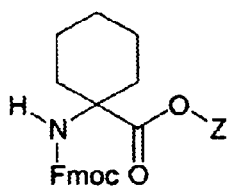
FIGS. 1–8 provide structures for a variety of compounds of the present invention.
Figure 1:
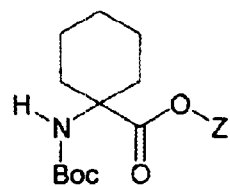
Figure 1:
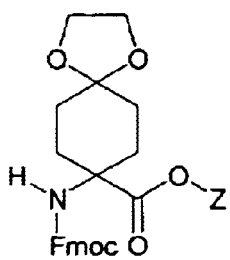
Figure 1:
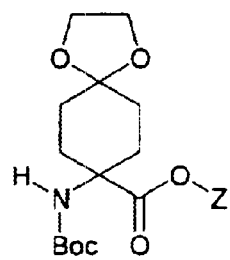
Figure 1:
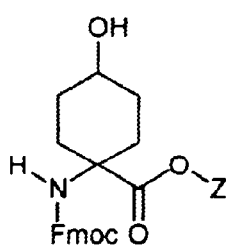
Figure 1:
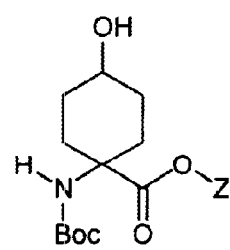
Figure 1:
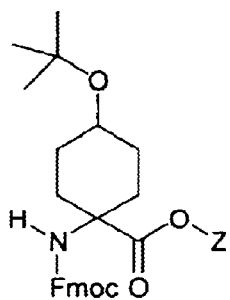
Figure 1:
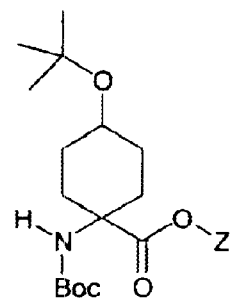
Figure 1:
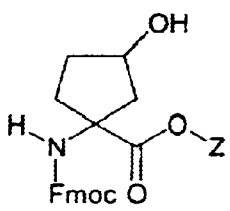
Figure 1:
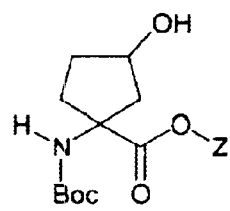
Figure 2:
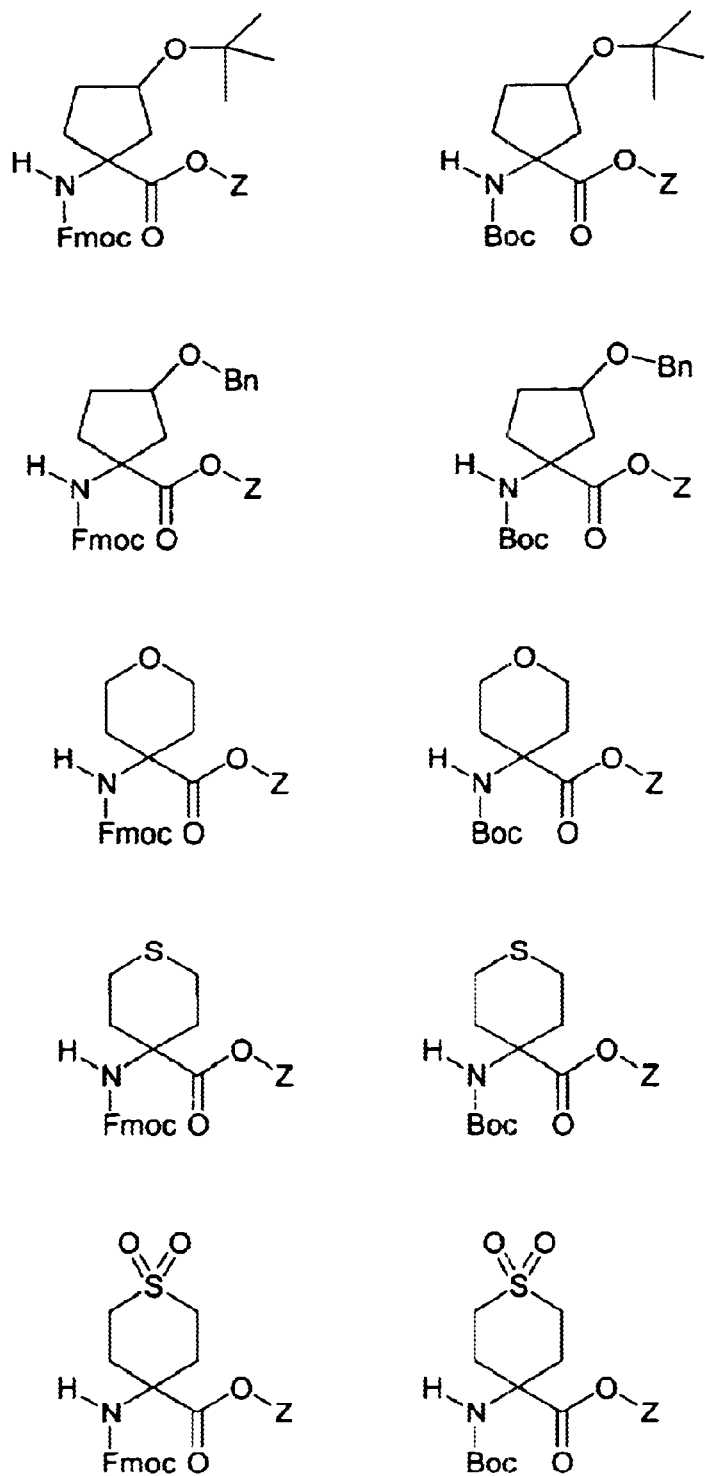
Figure 3:
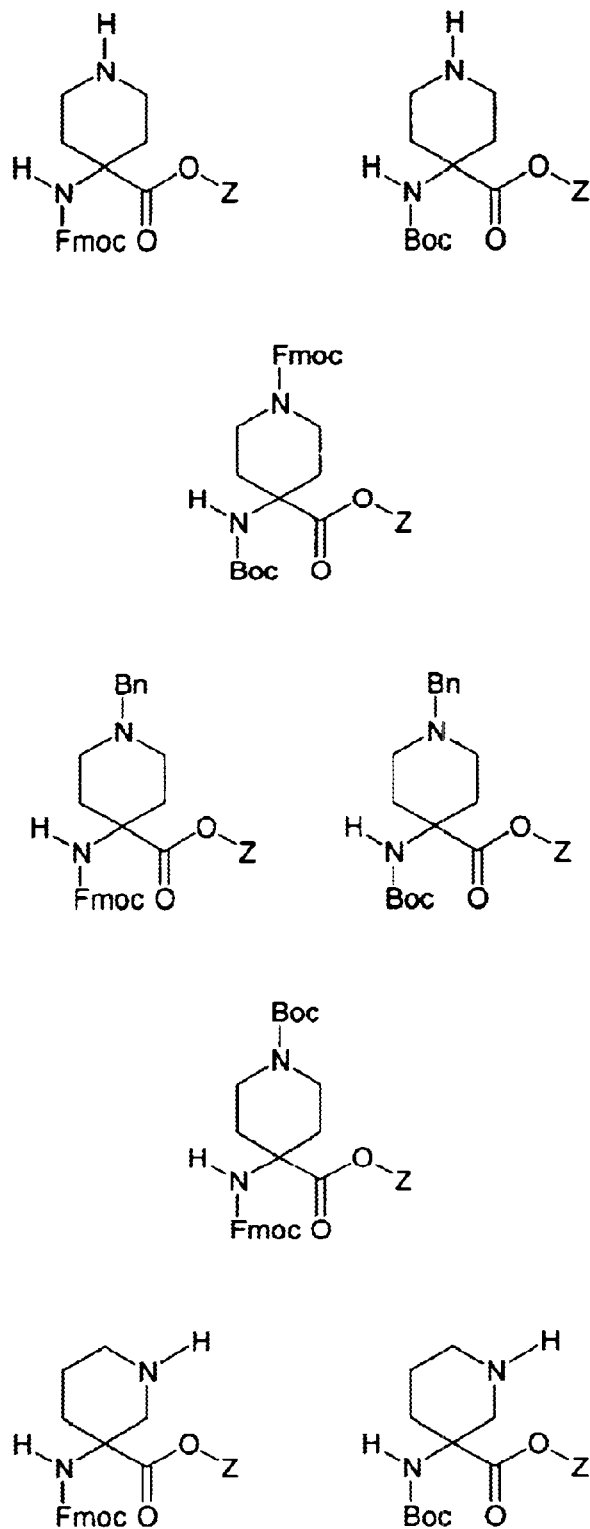
Figure 4:
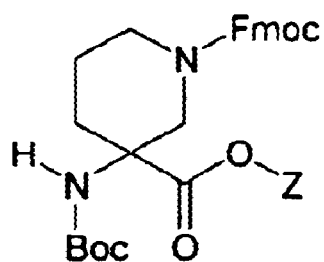
Figure 4:
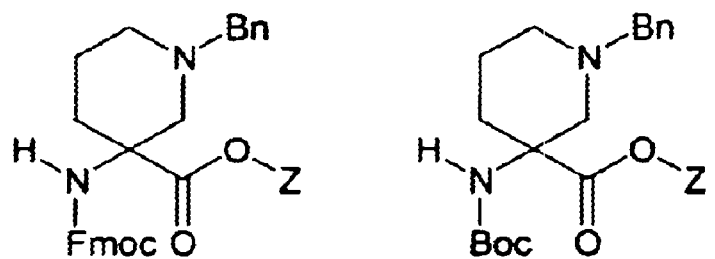
Figure 4:
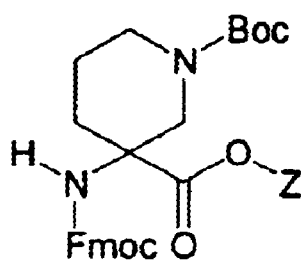
Figure 5:
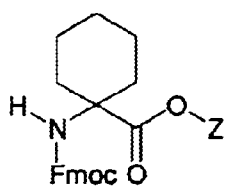
Figure 5:
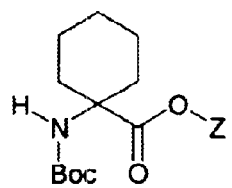
Figure 5:
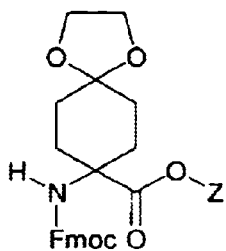
Figure 5:
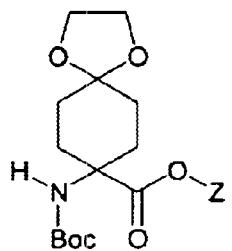
Figure 5:
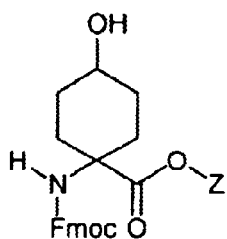
Figure 5:
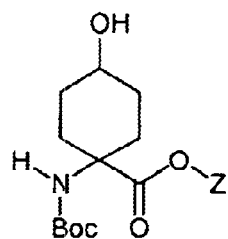
Figure 5:
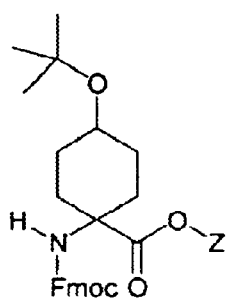
Figure 5:
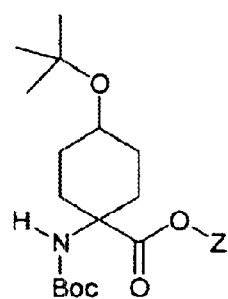
Figure 5:
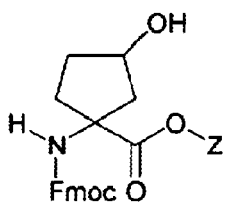
Figure 5:
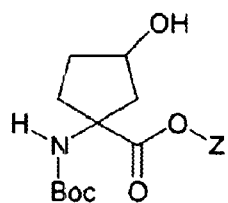
Figure 6:
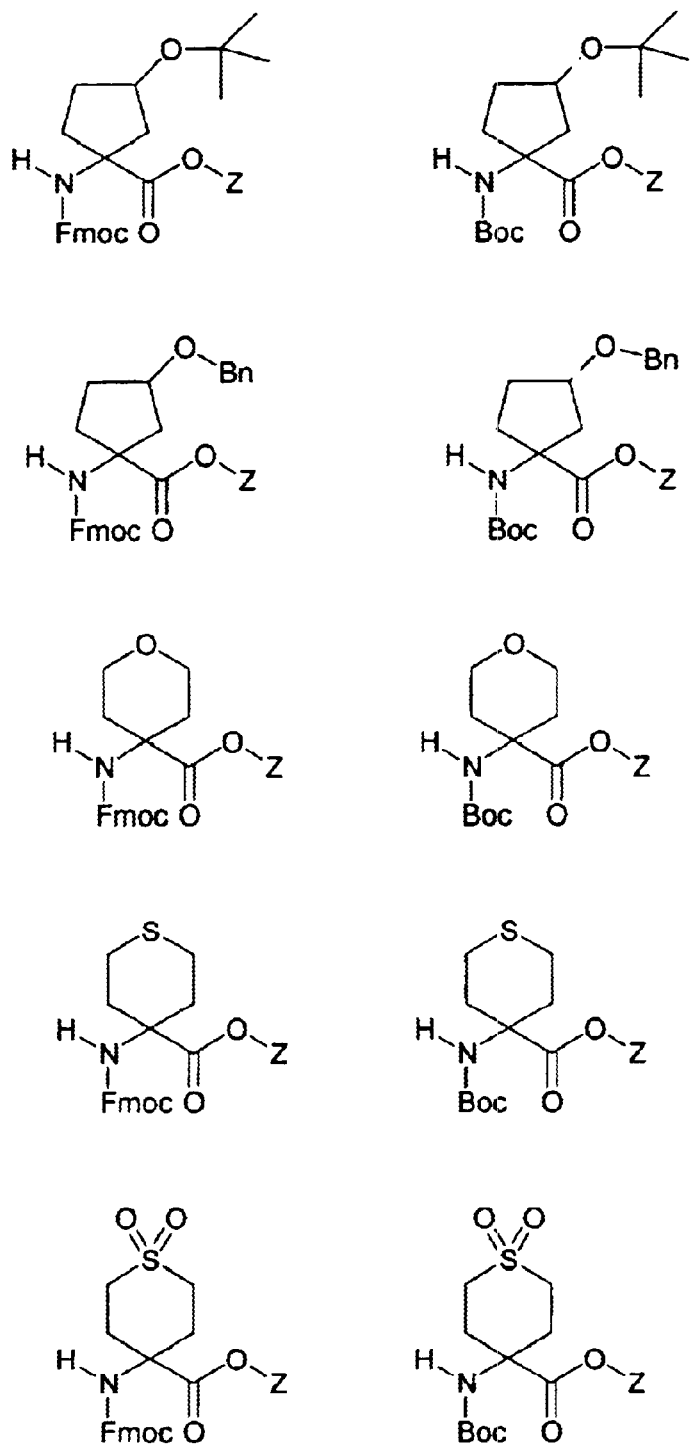
Figure 7:
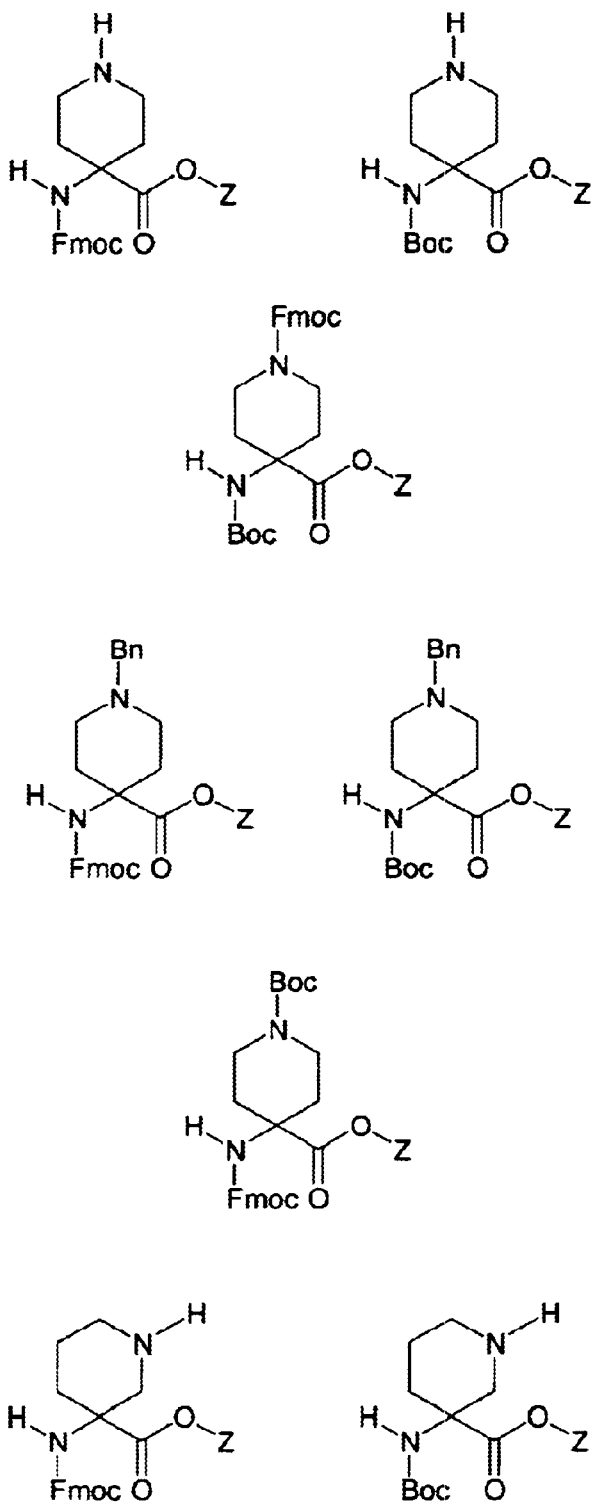
Figure 8:
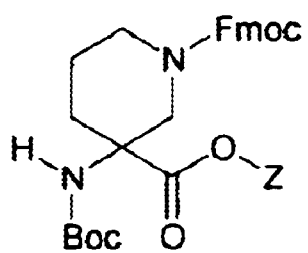
Figure 8:
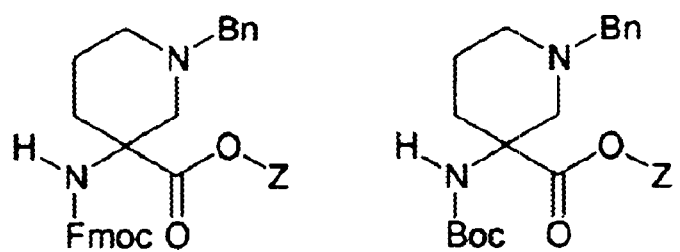
Figure 8:
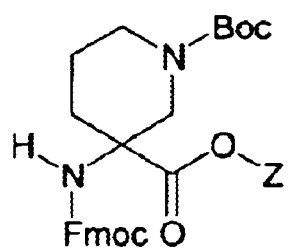

In one aspect, the present invention provides quaternary amino acid templates which are represented by the formula:

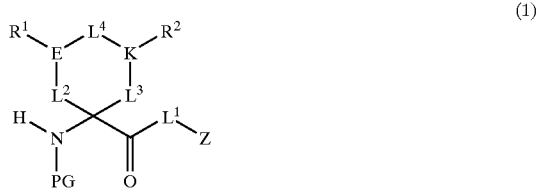

(1)

in which the letter Z represents the residue of a solid polymer support. Preferably, Z comprises the Merrifield resin, hydroxymethyl resin, Wang resin, aminomethyl resin, SASRIN resin, TentaGel S AC resin, TentaGel PHB resin, or TentaGel S $NH_2$ resin. Particularly preferred embodiments are those in which Z comprises the Merrifield resin or the Wang resin.

The symbol $L^1$ represents a divalent linkage comprising a divalent group of the formula —O—, —NH—, or —O—$CH_2$—$C_6H_4$—$CH_2O$—. Preferably, $L^1$ comprises —O— or NH—.

The symbol $L^2$ represents a divalent linkage comprising an alkylene, alkenylene, alkynylene, or a direct single bond. In preferred embodiments, $L^2$ comprises methylene, ethylene, or a direct single bond. More preferably, $L^2$ comprises —$CH_2$—, —$CH_2CH_2$—, or a direct single bond.

The symbol $L^3$ represents a divalent linkage comprising an alkylene, alkenylene, alkynylene, or a direct single bond. In preferred embodiments, $L^2$ comprises methylene, ethylene, or a direct single bond. More preferably, $L^3$ comprises —$CH_2$—, —$CH_2CH_2$—, or a direct single bond.

The symbol $L^4$ represents a divalent linkage comprising alkylene, —O—, —S—, —C(O)—, —S(O)—, —$S(O)_2$—,

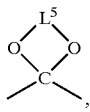

or a direct single or double bond, in which $L^5$ comprises —$CH_2CH_2$— or —$CH_2CH_2CH_2$—. In preferred embodiments, $L^4$ comprises lower alkylene, —O—, —S—, —C(O)—, —S(O)—, —$S(O)_2$—,

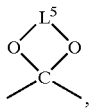

or a direct single bond. More preferably, $L^4$ comprises —$CH_2$—, —O—, —S—, —C(O)—, —S(O)—, —$S(O)_2$—,

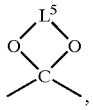

or a direct single bond.

The letter E represents a divalent linkage comprising —N—, —CH—, or —C=. In preferred embodiments, E comprises —N— or —CH—.

The letter K represents a divalent linkage comprising —N—, —CH—, or —C=. In preferred embodiments, K comprises —N— or —CH—.

Preferably, the groups $L^2$, $L^3$, $L^4$, E, and K are chosen to comprise a ring with 3 to 8 members.

The symbol PG represents a group comprising a hydrogen or an amino protecting group. In preferred embodiments, PG comprises hydrogen, benzyloxycarbonyl, 9-fluorenylmethoxycarbonyl, allyloxycarbonyl, phenyl, benzyl or t-butoxycarbonyl. More preferably, PG comprises hydrogen, benzyloxycarbonyl, 9-fluorenylmethoxycarbonyl, or t-butoxycarbonyl.

The symbol $R^1$ represents a group comprising alkyl, alkenyl, alkynyl, cycloalkyl, heterocyclyl, aryl, heteroaryl, hydrogen, halo, —O—$G^3$, —O—$G^4$, —$G^3$, —$G^4$, or —N($G^3$)$G^4$, in which $G^3$ and $G^4$ independently represent groups comprising

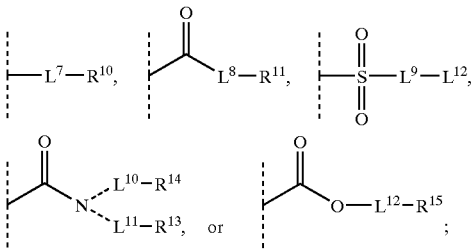

where $L^7$, $L^8$, $L^9$, $L^{10}$, $L^{11}$ $L^{12}$ independently represent groups comprising alkylene, alkenylene, alkynylene, cycloalkylene, cycloalkenylene, arylene, heterocyclylene, heteroarylene, fused cycloalkylarylene, fused cycloakylheteroarylene, fused heterocyclylarylene, fused heterocyclylheteroarylene, or a direct bond; and $R^{10}$, $R^{11}$, $R^{12}$, $R^{13}$, $R^{14}$, $R^{15}$ independently represent groups comprising alkyl, alkenyl, alkynyl, cycloalkyl, cycloalkenyl, heterocyclyl, heteroaryl, aryl, fused cycloalkylaryl, fused cycloakylheteroaryl, fused heterocyclylaryl, fused heterocyclylheteroaryl, —$NR^{18}R^{19}$, —$OR^{18}$, —$SR^{18}$, or hydrogen, where $R^{18}$ and $R^{19}$ independently represent groups comprising hydrogen, alkyl, alkynyl, alkenyl, cycloalkyl, cycloalkenyl, aryl, heterocyclyl, or heteroaryl. In preferred embodiments, $R^1$ comprises alkyl, alkenyl, alkynyl, cycloalkyl, heterocyclyl, aryl, heteroaryl, hydrogen, halo, —O—$G^3$, —O—$G^4$, —$G^3$, —$G^4$, or —N($G^3$)$G^4$, in which $G^3$ and $G^4$ independently represent groups comprising

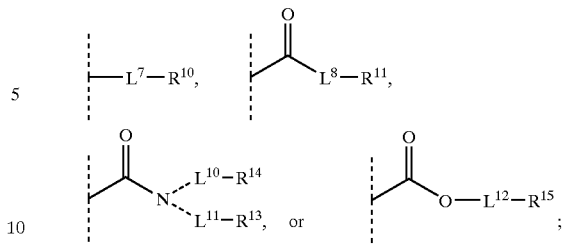

where $L^7$, $L^8$, $L^{10}$, $L^{11}$, $L^{12}$ independently represent groups comprising alkylene, alkenylene, alkynylene, cycloalkylene, cycloalkenylene, arylene, heterocyclylene, heteroarylene, fused cycloalkylarylene, fused cycloakylheteroarylene, fused heterocyclylarylene, fused heterocyclylheteroarylene, or a direct bond; and $R^{10}$, $R^{11}$, $R^{13}$, $R^{14}$, $R^{15}$ independently represent groups comprising alkyl, alkenyl, alkynyl, cycloalkyl, cycloalkenyl, heterocyclyl, heteroaryl, aryl, fused cycloalkylaryl, fused cycloakylheteroaryl, fused heterocyclylaryl, fused heterocyclylheteroaryl, —$NR^{18}R^{19}$, —$OR^{18}$, —$SR^{18}$, or hydrogen, where $R^{18}$ and $R^{19}$ independently represent groups comprising hydrogen, alkyl, alkynyl, alkenyl, cycloalkyl, cycloalkenyl, aryl, heterocyclyl, or heteroaryl. More preferably, $R^1$ comprises hydrogen, halo, and —$OG^3$ where $G^3$ comprises

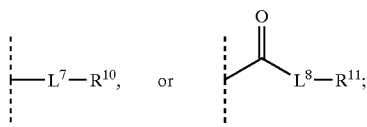

where $L^7$, $L^8$ independently represent groups comprising alkylene, alkenylene, alkynylene, cycloalkylene, cycloalkenylene, arylene, heterocyclylene, heteroarylene, fused cycloalkylarylene, fused cycloakylheteroarylene, fused heterocyclylarylene, fused heterocyclylheteroarylene, or a direct bond; and $R^{10}$, $R^{11}$ independently represent groups comprising alkyl, alkenyl, alkynyl, cycloalkyl, cycloalkenyl, heterocyclyl, heteroaryl, aryl, fused cycloalkylaryl, fused cycloakylheteroaryl, fused heterocyclylaryl, fused heterocyclylheteroaryl, —$NR^{18}R^{19}$, $OR^{18}$, $SR^{18}$, or hydrogen, where $R^{18}$ and $R^{19}$ independently represent groups comprising hydrogen, alkyl, alkynyl, alkenyl, cycloalkyl, cycloalkenyl, aryl, heterocyclyl, or heteroaryl. Even more preferably, $R^1$ comprises hydrogen, halogen, —OH, —O-tert-butyl, or —O-benzyl.

The symbol $R^2$ represents a group comprising alkyl, alkenyl, alkynyl, cycloalkyl, heterocyclyl, aryl, heteroaryl, hydrogen, halo, —O—$G^3$, —O—$G^4$, —$G^3$, —$G^4$, or —N($G^3$)$G^4$, in which $G^3$ and $G^4$ independently represent groups comprising

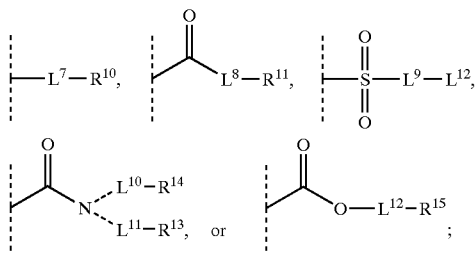

where $L^7$, $L^8$, $L^9$, $L^{10}$ $L^{11}$, $L^{12}$ independently represent groups comprising alkylene, alkenylene, alkynylene, cycloalkylene, cycloalkenylene, arylene, heterocyclylene, heteroarylene, fused cycloalkylarylene, fused cycloakylheteroarylene, fused heterocyclylarylene, fused heterocyclylheteroarylene, or a direct bond; and $R^{10}$, $R^{11}$, $R^{12}$, $R^{13}$, $R^{14}$, $R^{15}$ independently represent groups comprising alkyl, alkenyl, alkynyl, cycloalkyl, cycloalkenyl, heterocyclyl, heteroaryl, aryl, fused cycloalkylaryl, fused cycloakylheteroaryl, fused heterocyclylaryl, fused heterocyclylheteroaryl, —$NR^{18}R^{19}$, —$OR^{18}$, —$SR^{18}$, or hydrogen, where $R^{18}$ and $R^{19}$ independently represent hydrogen, alkyl, alkynyl, alkenyl, cycloalkyl, cycloalkenyl, aryl, heterocyclyl, or heteroaryl. In preferred embodiments, $R^2$ comprises alkyl, alkenyl, alkynyl, cycloalkyl, heterocyclyl, aryl, heteroaryl, hydrogen, halo, —O—$G^3$, —O—$G^4$, —$G^3$, —$G^4$, or —$N(G^3)G^4$, in which $G^3$ and $G^4$ independently represent groups comprising

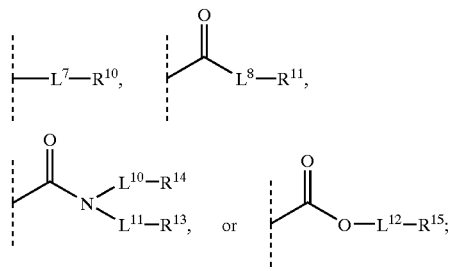

where $L^7$, $L^8$, $L^{10}$, $L^{11}$, $L^{12}$ independently represent groups comprising alkylene, alkenylene, alkynylene, cycloalkylene, cycloalkenylene, arylene, heterocyclylene, heteroarylene, fused cycloalkylarylene, fused cycloakylheteroarylene, fused heterocyclylarylene, fused heterocyclylheteroarylene, or a direct bond; and $R^{10}$, $R^{11}$, $R^{13}$, $R^{14}$, $R^{15}$ independently represent groups comprising alkyl, alkenyl, alkynyl, cycloalkyl, cycloalkenyl, heterocyclyl, heteroaryl, aryl, fused cycloalkylaryl, fused cycloakylheteroaryl, fused heterocyclylaryl, fused heterocyclylheteroaryl, —$NR^{18}R^{19}$, —$OR^{18}$, —$SR^{18}$, or hydrogen, where $R^{18}$ and $R^{19}$ independently represent groups comprise hydrogen, alkyl, alkynyl, alkenyl, cycloalkyl, cycloalkenyl, aryl, heterocyclyl, or heteroaryl. More preferably, $R^2$ comprises alkyl, alkenyl, alkynyl, cycloalkyl, heterocyclyl, aryl, heteroaryl, hydrogen, or —$G^5$, in which $G^5$ comprises

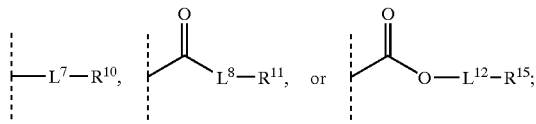

where $L^7$, $L^8$, $L^{12}$ independently represent groups comprising alkylene, alkenylene, alkynylene, cycloalkylene, cycloalkenylene, arylene, heterocyclylene, heteroarylene, fused cycloalkylarylene, fused cycloakylheteroarylene, fused heterocyclylarylene, fused heterocyclylheteroarylene, or a direct bond; and $R^{10}$, $R^{11}$, $R^{15}$ independently represent groups comprising alkyl, alkenyl, alkynyl, cycloalkyl, cycloalkenyl, heterocyclyl, heteroaryl, aryl, fused cycloalkylaryl, fused cycloakylheteroaryl, fused heterocyclylaryl, fused heterocyclylheteroaryl, —$NR^{18}R^{19}$, —$OR^{18}$, —$SR^{18}$, or hydrogen, where $R^{18}$ and $R^{19}$ independently represent groups comprising hydrogen, alkyl, alkynyl, alkenyl, cycloalkyl, cycloalkenyl, aryl, heterocyclyl, or heteroaryl. Even more preferably, $R^2$ comprises hydrogen, benzyl, benzyloxycarbonyl, 9-fluorenylmethoxycarbonyl, or t-butoxycarbonyl.

$R^1$ and $R^2$ may be taken together to constitute a cycloalkyl or heterocyclyl ring, or, where L comprises a direct bond, $R^1$ and $R^2$ may be taken together to constitute a fused aryl or heteroaryl ring.

In a second aspect, the amino acid templates of the present invention are represented by formula (1a):

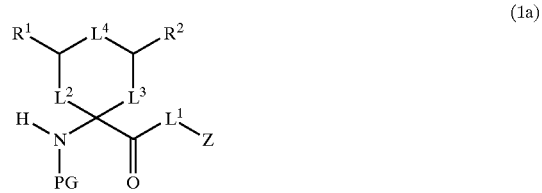

(1a)

in which Z comprises the Merrifield resin, hydroxymethyl resin, Wang resin, or aminomethyl resin; E and K independently comprise CH—; $L^1$ comprises —O— or —NH—; $L^2$ and $L^3$ independently comprise —$CH_2$—, —$CH_2CH_2$—, or a direct single bond; $L^4$ comprises —$CH_2$—, —C(O)—,

or a direct single bond; $L^5$ comprises $CH_2CH_2$— or $CH_2CH_2CH_2$—; PG comprises hydrogen, benzyloxycarbonyl, 9-fluorenylmethoxycarbonyl, or t-butoxycarbonyl; and $R^1$ and $R^2$ independently represent groups comprising alkyl, alkenyl, alkynyl, cycloalkyl, heterocyclyl, aryl, heteroaryl, hydrogen, halo, —O—$G^3$, —O—$G^4$, —$G^3$, —$G^4$, or —$N(G^3)G^4$, where $R^1$ and $R^2$ may be taken together to constitute a cycloalkyl or heterocyclyl ring, $G^3$ and $G^4$ independently represent groups comprising

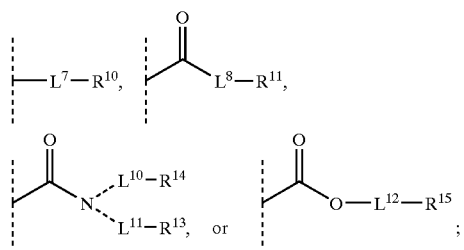

where $L^7$, $L^8$, $L^{10}$, $L^{11}$, $L^{12}$ independently represent groups comprising alkylene, alkenylene, alkynylene, cycloalkylene, cycloalkenylene, arylene, heterocyclylene, heteroarylene, fused cycloalkylarylene, fused cycloakylheteroarylene, fused heterocyclylarylene, fused heterocyclylheteroarylene, or a direct bond; and $R^{10}$, $R^{11}$ $R^{13}$, $R^{14}$, $R^{15}$ independently represent groups comprising alkyl, alkenyl, alkynyl, cycloalkyl, cycloalkenyl, heterocyclyl, heteroaryl, aryl, fused cycloalkylaryl, fused cycloakylheteroaryl, fused heterocyclylaryl, fused heterocyclylheteroaryl, —$NR^{18}R^{19}$, —$OR^{18}$, —$SR^{18}$, or hydrogen, where $R^{18}$ and $R^{19}$ independently represent groups comprising hydrogen, alkyl, alkynyl, alkenyl, cycloalkyl, cycloalkenyl, aryl, heterocyclyl, or heteroaryl.

In an embodiment of the second aspect, the amino acid templates of the present invention are represented by formula (1b):

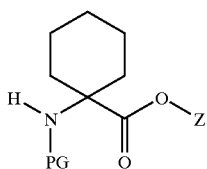
(1b)

in which Z comprises the Wang or Merrifield resin; $L^1$ comprises —O—; $L^2$ comprises —$CH_2$—; $L^3$ comprises $CH_2$—; $L^4$ comprises a —$CH_2$—; E and K independently comprise CH—; PG comprises hydrogen, benzyloxycarbonyl, 9-fluorenylmethoxycarbonyl, or t-butoxycarbonyl; and $R^1$ and $R^2$ independently comprise hydrogen.

In a second embodiment of the second aspect, the amino acid templates of the present invention, in which Z comprises the Wang resin, are represented by the formulae:

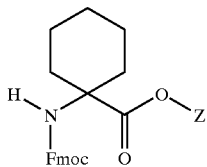 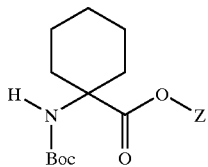

In a third embodiment of the second aspect, the amino acid templates of the present invention, in which Z comprises the Merrifield resin, are represented by the formulae:

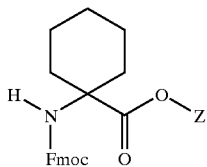 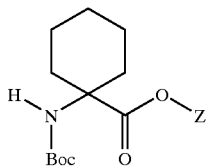

In a fourth embodiment of the second aspect, the amino acid templates of the present invention are represented by formula (1c):

(1c)

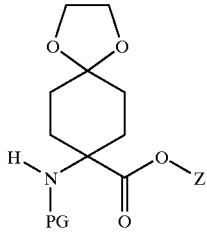

in which Z comprises the Wang or Merrifield resin; $L^1$ comprises —O—; $L^2$ comprises —$CH_2$—; $L^3$ comprises $CH_2$—; $L^4$ comprises

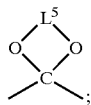

$L^5$ comprises $CH_2CH_2$—; E and K independently comprise —CH—; PG comprises hydrogen, benzyloxycarbonyl, 9-fluorenylmethoxycarbonyl, or t-butoxycarbonyl; and $R^1$ and $R^2$ independently comprise hydrogen.

In a fifth embodiment of the second aspect, the amino acid templates of the present invention, in which Z comprises the Wang resin, are represented by the formulae:

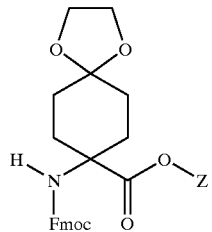 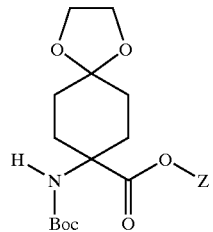

In a sixth embodiment of the second aspect, the amino acid templates of the present invention, in which Z comprises the Merrifield resin, are represented by the formulae:

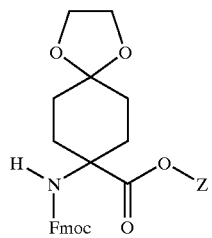 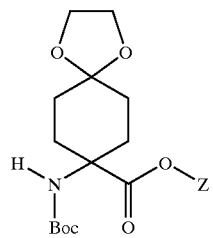

In a seventh embodiment of the second aspect, the amino acid templates of the present invention are represented by the formula (1d):

(1d)

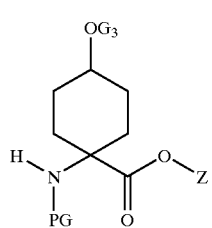

in which Z comprises the Wang or Merrifield resin; $L^1$ comprises O—; $L^2$ comprises —$CH_2CH_2$—; $L^3$ comprises $CH_2$—; $L^4$ comprises a direct single bond; E comprises —CH—; K comprises —CH—; $R^2$ comprises H; and $R^1$ comprises —$OG^3$ where $G^3$ is

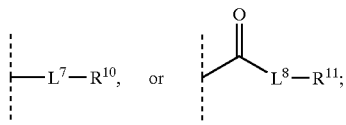

where $L^7$, $L^8$ independently represent groups comprising alkylene, alkenylene, alkynylene, cycloalkylene, cycloalkenylene, arylene, heterocyclylene, heteroarylene, fused cycloalkylarylene, fused cycloakylheteroarylene, fused heterocyclylarylene, fused heterocyclylheteroarylene, or a direct bond; and $R^{10}$, $R^{11}$ independently represent groups comprising alkyl, alkenyl, alkynyl, cycloalkyl, cycloalkenyl, heterocyclyl, heteroaryl, aryl, fused cycloalkylaryl, fused cycloakylheteroaryl, fused heterocyclylaryl, fused heterocyclylheteroaryl, —$NR^{18}R^{19}$, $OR^{18}$, $SR^{18}$, or hydrogen, where $R^{18}$ and $R^{19}$ independently represent groups comprising hydrogen, alkyl, alkynyl, alkenyl, cycloalkyl, cycloalkenyl, aryl, heterocyclyl, or heteroaryl.

In an eighth embodiment of the second aspect, the amino acid templates of the present invention are represented by formula (1e):

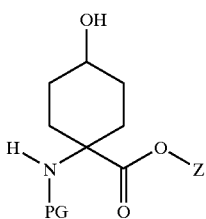
(1e)

in which Z comprises the Wang or Merrifield resin; $L^1$ comprises —O—; $L^2$ comprises —CH$_2$CH$_2$—; $L^3$ comprises CH$_2$—; $L^4$ comprises a direct single bond; E and K independently comprise —CH—; PG comprises hydrogen, benzyloxycarbonyl, 9-fluorenylmethoxycarbonyl, or t-butoxycarbonyl; $R^1$ comprises OH; and $R^2$ comprises hydrogen.

In a ninth embodiment of the second aspect, the amino acid templates of the present invention, in which Z comprises the Wang resin, are represented by the formulae:

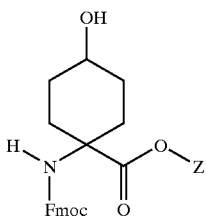 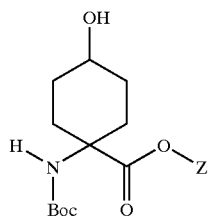

In a tenth embodiment of the second aspect, the amino acid templates of the present invention, in which Z comprises the Merrifield resin, are represented by the formulae:

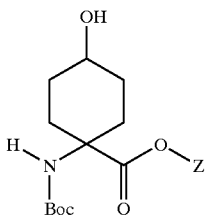 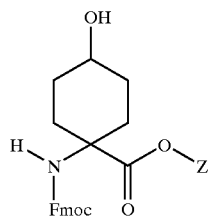

In an eleventh embodiment of the second aspect, the amino acid templates of the present invention are represented by formula (1g):

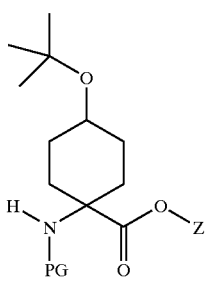
(1g)

in which Z comprises the Wang or Merrifield resin; $L^1$ comprises —O—; $L^2$ comprises —CH$_2$CH$_2$—; $L^3$ comprises CH$_2$—; $L^4$ comprises a direct single bond; E and K independently comprise —CH—; PG comprises hydrogen, benzyloxycarbonyl, 9-fluorenylmethoxycarbonyl, or t-butoxycarbonyl; $R^1$ comprises O-tert-butyl; and $R^2$ comprises hydrogen.

In a twelfth embodiment of the second aspect, the amino acid templates of the present invention, in which Z comprises the Wang resin, are represented by the formulae:

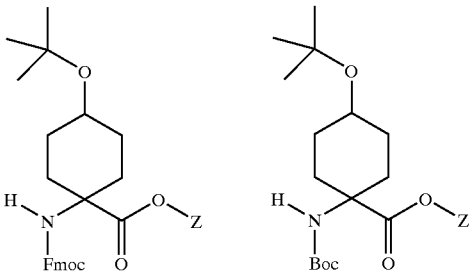

In a thirteenth embodiment of the second aspect, the amino acid templates of the present invention, in which Z represents the Merrifield resin, are represented by the formulae:

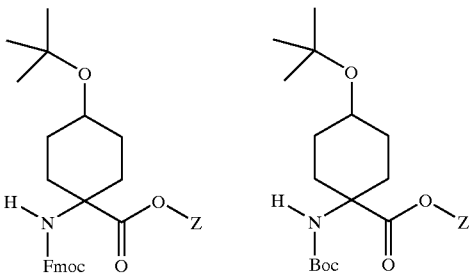

In an fourteenth embodiment of the second aspect, the amino acid templates of the present invention are represented by formula (1h):

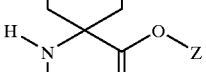
(1h)

in which Z comprises the Wang or Merrifield resin; $L^1$ comprises O—; $L^2$ comprises —CH$_2$—; $L^3$ comprises CH$_2$—; $L^4$ comprises a direct single bond; E and K independently comprise —CH—; PG comprises hydrogen, benzyloxycarbonyl, 9-fluorenylmethoxy-carbonyl, or t-butoxycarbonyl; $R^1$ comprises —O—$G^3$; and $R^2$ comprises hydrogen, where $G^3$ represents a group comprising

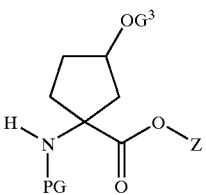

where $L^7$, $L^8$ independently represent groups comprising independently, alkylene, alkenylene, alkynylene, cycloalkylene, cycloalkenylene, arylene, heterocyclylene, heteroarylene, fused cycloalkylarylene, fused cycloakylheteroarylene, fused heterocyclylarylene, fused heterocyclylheteroarylene, or a direct bond; and $R^{10}$, $R^{11}$ independently represent groups comprising alkyl, alkenyl, alkynyl, cycloalkyl, cycloalkenyl, heterocyclyl, heteroaryl, aryl, fused cycloalkylaryl, fused cycloakylheteroaryl, fused heterocyclylaryl, fused heterocyclylheteroaryl, —$NR^{18}R^{19}$, —$OR^{18}$, —$SR^{18}$, or hydrogen, where $R^{18}$ and $R^{19}$ independently represent groups comprising hydrogen, alkyl, alkynyl, alkenyl, cycloalkyl, cycloalkenyl, aryl, heterocyclyl, or heteroaryl.

In a fifteenth embodiment of the second aspect, the amino acid templates of the present invention are represented by the formula (1i):

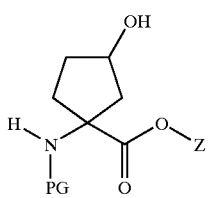

(1i)

in which Z comprises the Wang or Merrifield resin; $L^1$ comprises —O—; $L^2$ comprises —$CH_2$—; $L^3$ comprises —$CH_2$—; $L^4$ comprises a direct single bond; E and K independently comprise —CH—; PG comprises hydrogen, benzyloxycarbonyl, 9-fluorenylmethoxy-carbonyl, or t-butoxycarbonyl; $R^1$ comprises OH; and $R^2$ comprises hydrogen.

In a sixteenth embodiment of the second aspect, the amino acid templates of the present invention, in which Z comprises the Wang resin, are represented by the formulae:

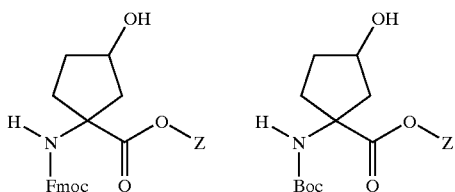

In a seventeenth embodiment of the second aspect, the amino acid templates of the present invention, in which Z comprises the Merrifield resin, are represented by the formulae:

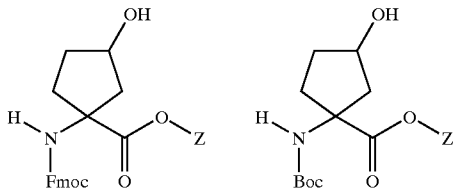

In an eighteenth embodiment of the second aspect, the amino acid templates of the present invention are represented by the formula (1j):

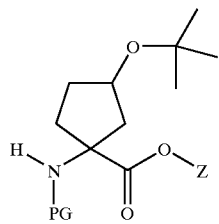

(1j)

in which Z comprises the Wang or Merrifield resin; $L^1$ comprises O—; $L^2$ comprises —$CH_2$—; $L^3$ comprises $CH_2$—; $L^4$ comprises a direct single bond; E and K independently comprise —CH—; PG comprises hydrogen, benzyloxycarbonyl, 9-fluorenylmethoxy-carbonyl, or t-butoxycarbonyl; $R^1$ comprises O-tert-butyl; and $R^2$ comprises hydrogen.

In a nineteenth embodiment of the second aspect, the amino acid templates of the present invention, in which Z comprises the Wang resin, are represented by the formulae:

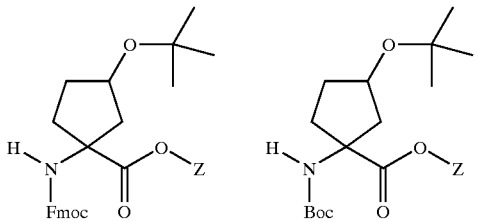

In a twentieth embodiment of the second aspect, the amino acid templates of the present invention, in which Z comprises the Merrifield resin, are represented by the formulae:

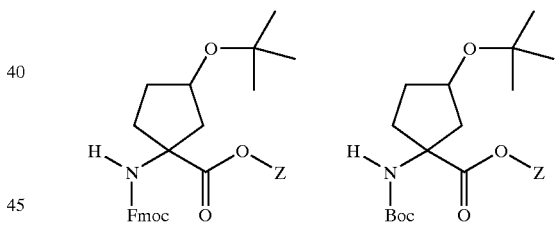

In an twenty-first aspect of the second embodiment, the amino acid templates of the present invention are represented by the formula (1k):

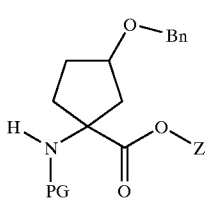

(1k)

in which Z comprises the Wang or Merrifield resin; $L^1$ comprises O—; $L^2$ comprises —$CH_2$—; $L^3$ comprises $CH_2$—; $L^4$ comprises a direct single bond; E and K independently comprise —CH—; PG comprises hydrogen, benzyloxycarbonyl, 9-fluorenylmethoxy-carbonyl, or t-butoxycarbonyl; $R^1$ comprises O—benzyl; and $R^2$ comprises hydrogen.

In a twenty-second embodiment of the second aspect, the amino acid templates of the present invention, in which Z comprises the Wang resin, are represented by the formulae:

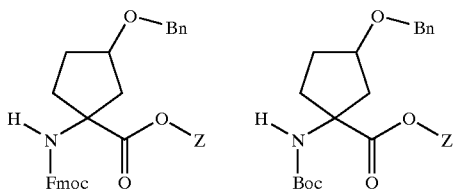

In a twenty-third embodiment of the second aspect, the amino acid templates of the present invention, in which Z comprises the Merrifield resin, are represented by the formulae:

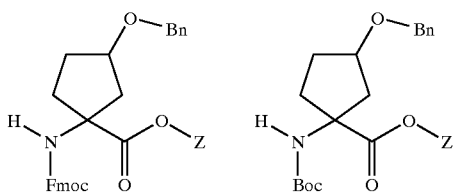

In a third aspect, the amino acid templates of the present invention are represented by formula (1a):

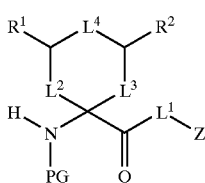

(1a)

in which Z comprises the Merrifield resin, hydroxymethyl resin, Wang resin, or aminomethyl resin; E and K independently comprise —CH—; $L^1$ comprises —O— or —NH—; $L^2$ and $L^3$ independently comprise —CH$_2$—, —CH$_2$CH$_2$—, or a direct single bond; $L^4$ comprises —O—, —S—, —S(O)—, or —S(O)$_2$—; PG comprises hydrogen, benzyloxycarbonyl, 9-fluorenylmethoxycarbonyl, or t-butoxycarbonyl; and $R^1$ and $R^2$ independently represent groups comprising alkyl, alkenyl, alkynyl, cycloalkyl, heterocyclyl, aryl, heteroaryl, hydrogen, halo, —O—G$^3$, —O—G$^4$, —G$^3$, —G$^4$, or —N(G$^3$)G$^4$, where $R^1$ and $R^2$ may be taken together to constitute a cycloalkyl or heterocyclyl ring, and G$^3$ and G$^4$ independently represent groups comprising

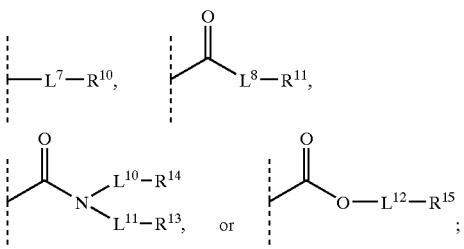

where $L^7$, $L^8$, $L^{10}$, $L^{11}$, $L^{12}$ independently represent groups comprising alkylene, alkenylene, alkynylene, cycloalkylene, cycloalkenylene, arylene, heterocyclylene, heteroarylene, fused cycloalkylarylene, fused cycloakylheteroarylene, fused heterocyclylarylene, fused heterocyclylheteroarylene, or a direct bond; and $R^{10}$, $R^{11}$, $R^{13}$, $R^{14}$, $R^{15}$ independently represent groups comprising alkyl, alkenyl, alkynyl, cycloalkyl, cycloalkenyl, heterocyclyl, heteroaryl, aryl, fused cycloalkylaryl, fused cycloakylheteroaryl, fused heterocyclylaryl, fused heterocyclylheteroaryl, —NR$^{18}$R$^{19}$, —OR$^{18}$, —SR$^{18}$, or hydrogen, where $R^{18}$ and $R^{19}$ independently represent groups comprising hydrogen, alkyl, alkynyl, alkenyl, cycloalkyl, cycloalkenyl, aryl, heterocyclyl, or heteroaryl.

In an embodiment of the third aspect, the amino acid templates of the present invention are represented by formula (1l):

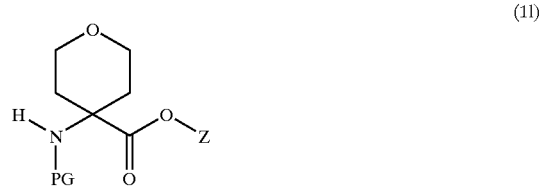

(1l)

in which Z comprises the Wang or Merrifield resin; $L^1$ comprises O—; $L^2$ comprises —CH$_2$—; $L^3$ comprises —CH$_2$—; $L^4$ comprises a —O—; E and K independently comprise —CH—; PG comprises hydrogen, benzyloxycarbonyl, 9-fluorenylmethoxycarbonyl, or t-butoxycarbonyl; and $R^1$ and $R^2$ independently comprise hydrogen.

In a second embodiment of the third aspect, the amino acid templates of the present invention, in which Z comprises the Wang resin, are represented by the formulae:

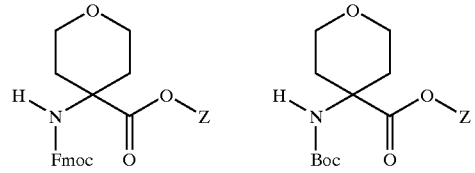

In a third embodiment of the third aspect, the amino acid templates of the present invention, in which Z comprises the Merrifield resin, are represented by the formulae:

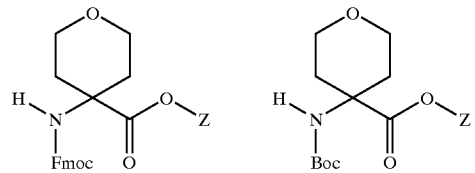

In a fourth embodiment of the third aspect, the amino acid templates of the present invention are represented by formula (1m):

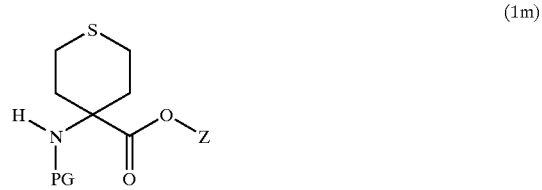

(1m)

in which Z comprises the Wang or Merrifield resin; $L^1$ comprises O—; $L^2$ comprises —CH$_2$—; $L^3$ comprises $CH_2$—; $L^4$ comprises a S—; E and K independently comprise —CH—; PG comprises hydrogen, benzyloxycarbonyl, 9-fluorenylmethoxycarbonyl, or t-butoxycarbonyl; and $R^1$ and $R^2$ independently comprise hydrogen.

In a fifth embodiment of the third aspect, the amino acid templates of the present invention, in which Z comprises the Wang resin, are represented by the formulae:

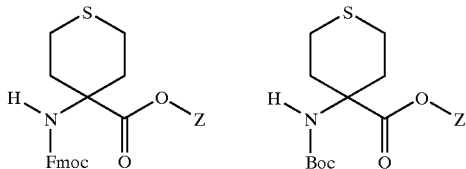

In a sixth embodiment of the third aspect, the amino acid templates of the present invention, in which Z comprises the Merrifield resin, are represented by the formulae:

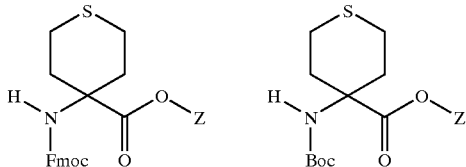

In a seventh embodiment of the third aspect, the amino acid templates of the present invention are represented by formula (1n):

(1n)

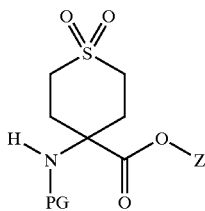

in which Z comprises the Wang or Merrifield resin; $L^1$ comprises O—; $L^2$ comprises —$CH_2$—; $L^3$ comprises $CH_2$—; $L^4$ comprises a $S(O)_2$—; E and K independently comprise —CH—; PG comprises hydrogen, benzyloxycarbonyl, 9-fluorenylmethoxycarbonyl, or t-butoxycarbonyl; and $R^1$ and $R^2$ independently comprise hydrogen.

In an eighth embodiment of the third aspect, the amino acid templates of the present invention, in which Z comprises the Wang resin, are represented by the formulae:

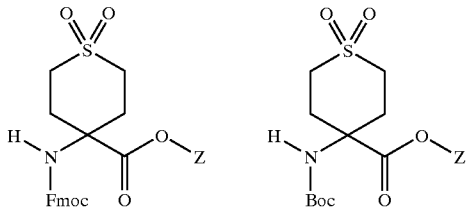

In a ninth embodiment of the third aspect, the amino acid templates of the present invention, in which Z comprises the Merrifield resin, are represented by the formulae:

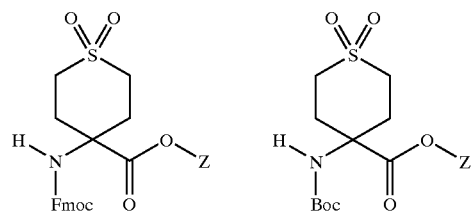

In a fourth aspect, the amino acid templates of the present invention are represented by formula (1o):

(1o)

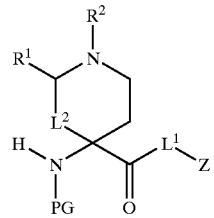

in which Z comprises the Merrifield resin, hydroxymethyl resin, Wang resin, or aminomethyl resin; E comprises —CH—; K comprises N—; $L^1$ comprises O— or N—; $L^2$ comprises —$CH_2$—, —$CH_2CH_2$—, or a direct single bond; $L^3$ comprises —$CH_2CH_2$—; $L^4$ comprises a direct single bond; PG comprises hydrogen, benzyloxycarbonyl, 9-fluorenylmethoxycarbonyl, or t-butoxycarbonyl; $R^1$ comprises alkyl, alkenyl, alkynyl, cycloalkyl, heterocyclyl, aryl, heteroaryl, hydrogen, halo, —O—$G^3$, —$G^3$, or —N($G^3$)$G^4$ where $G^3$ and $G^4$ independently represent groups comprising

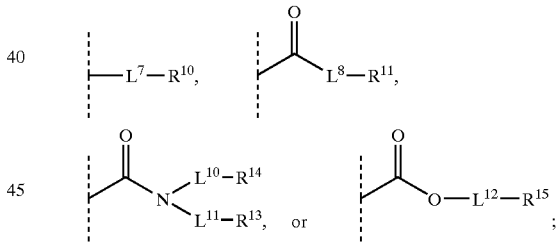

where $L^7$, $L^8$, $L^{10}$, $L^{11}$, $L^{12}$ independently represent groups comprising alkylene, alkenylene, alkynylene, cycloalkylene, cycloalkenylene, arylene, heterocyclylene, heteroarylene, fused cycloalkylarylene, fused cycloakylheteroarylene, fused heterocyclylarylene, fused heterocyclylheteroarylene, or a direct bond; and $R^{10}$, $R^{11}$, $R^{13}$, $R^{14}$, $R^{15}$ independently represent a group comprising alkyl, alkenyl, alkynyl, cycloalkyl, cycloalkenyl, heterocyclyl, heteroaryl, aryl, fused cycloalkylaryl, fused cycloakylheteroaryl, fused heterocyclylaryl, fused heterocyclylheteroaryl, —$NR^{18}R^{19}$, —$OR^{18}$, —$SR^{18}$, or hydrogen, where $R^{18}$ and $R^{19}$ independently represent groups comprising hydrogen, alkyl, alkynyl, alkenyl, cycloalkyl, cycloalkenyl, aryl, heterocyclyl, or heteroaryl; and $R^2$ comprises alkyl, alkenyl, alkynyl, cycloalkyl, heterocyclyl, aryl, heteroaryl, hydrogen, or —$G^5$, where $G^5$ represents a group comprising

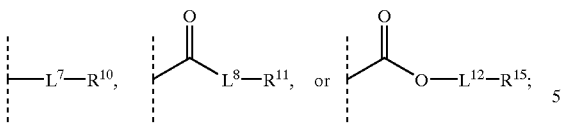

where $L^7$, $L^8$, $L^{12}$ independently represent groups comprising alkylene, alkenylene, alkynylene, cycloalkylene, cycloalkenylene, arylene, heterocyclylene, heteroarylene, fused cycloalkylarylene, fused cycloakylheteroarylene, fused heterocyclylarylene, fused heterocylylheteroarylene, or a direct bond; and $R^{10}$, $R^{11}$, $R^{15}$ independently represent groups comprising alkyl, alkenyl, alkynyl, cycloalkyl, cycloalkenyl, heterocyclyl, heteroaryl, aryl, fused cycloalkylaryl, fused cycloakylheteroaryl, fused heterocyclylaryl, fused heterocyclylheteroaryl, —$NR^{18}R^{19}$, —$OR^{18}$, —$SR^{18}$, or hydrogen, where $R^{18}$ and $R^{19}$ independently represent groups comprising hydrogen, alkyl, alkynyl, alkenyl, cycloalkyl, cycloalkenyl, aryl, heterocyclyl, or heteroaryl.

In an embodiment of the fourth aspect, the amino acid templates of the present invention are represented by formula (1p):

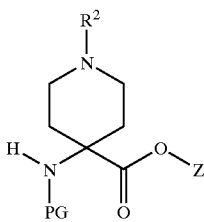

(1p)

in which Z comprises the Wang or Merrifield resin; $L^1$ comprises —O—; $L^2$ comprises —$CH_2$—; $L^3$ comprises $CH_2CH_2$—; $L^4$ comprises a direct single bond; E comprises CH—; K comprises N—; PG comprises hydrogen, benzyloxycarbonyl, 9-fluorenylmethoxycarbonyl, or t-butoxycarbonyl; $R^1$ comprises hydrogen; and $R^2$ comprises alkyl, alkenyl, alkynyl, cycloalkyl, heterocyclyl, aryl, heteroaryl, hydrogen, or —$G^5$, where $G^5$ represents a group comprising

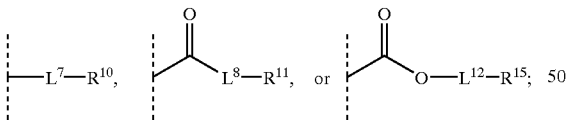

where $L^7$, $L^8$, $L^{12}$ independently represent groups comprising alkylene, alkenylene, alkynylene, cycloalkylene, cycloalkenylene, arylene, heterocyclylene, heteroarylene, fused cycloalkylarylene, fused cycloakylheteroarylene, fused heterocyclylarylene, fused heterocylylheteroarylene, or a direct bond; and $R^{10}$, $R^{11}$, $R^{15}$ independently represent groups comprising alkyl, alkenyl, alkynyl, cycloalkyl, cycloalkenyl, heterocyclyl, heteroaryl, aryl, fused cycloalkylaryl, fused cycloakylheteroaryl, fused heterocyclylaryl, fused heterocyclylheteroaryl, —$NR^{18}R^{19}$, —$OR^{18}$, —$SR^{18}$, or hydrogen, where $R^{18}$ and $R^{19}$ independently represent groups comprising hydrogen, alkyl, alkynyl, alkenyl, cycloalkyl, cycloalkenyl, aryl, heterocyclyl, or heteroaryl.

In a second embodiment of the fourth aspect, the amino acid templates of the present invention are represented by formula (1q):

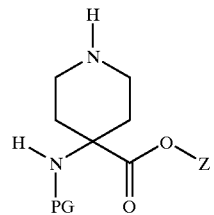

(1q)

in which Z comprises the Wang or Merrifield resin; $L^1$ comprises O—; $L^2$ comprises —$CH_2$—; $L^3$ comprises $CH_2CH_2$—; $L^4$ comprises a direct single bond; E comprises —CH—; K comprises —N—; PG comprises hydrogen, benzyloxycarbonyl, 9-fluorenylmethoxycarbonyl, or t-butoxycarbonyl; and $R^1$ and $R^2$ independently comprise hydrogen.

In a third embodiment of the fourth aspect, the amino acid templates of the present invention, in which Z comprises the Wang resin, are represented by the formulae:

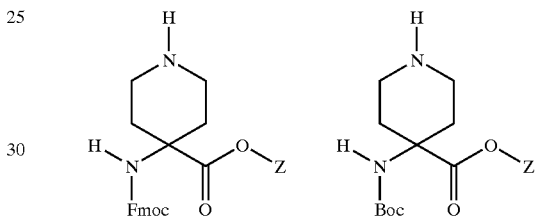

In a fourth embodiment of the fourth aspect, the amino acid templates of the present invention, in which Z comprises the Merrifield resin, are represented by the formulae:

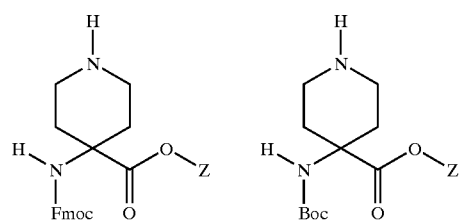

In a fifth embodiment of the fourth aspect, the amino acid templates of the present invention are represented by formula (1r):

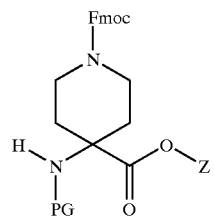

(1r)

in which Z comprises the Wang or Merrifield resin; $L^1$ comprises O—; $L^2$ comprises —$CH_2$—; $L^3$ comprises $CH_2CH_2$—; $L^4$ comprises a direct single bond; E comprises —CH—; K comprises —N—; PG comprises hydrogen, benzyloxycarbonyl, 9-fluorenylmethoxycarbonyl, or t-butoxycarbonyl; $R^1$ comprises hydrogen, and $R^2$ comprises 9-fluorenylmethoxycarbonyl.

In a sixth embodiment of the fourth aspect, the amino acid templates of the present invention, in which Z comprises the Wang resin, are represented by the formula:

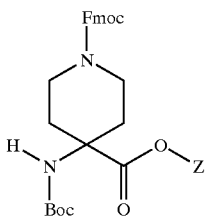

In an seventh embodiment of the fourth aspect, the amino acid templates of the present invention, in which Z comprises the Merrifield resin, are represented by the formula:

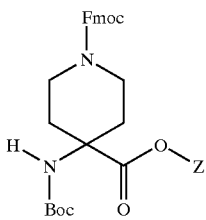

In a eighth embodiment of the fourth aspect, the amino acid templates of the present invention are represented by formula (1s):

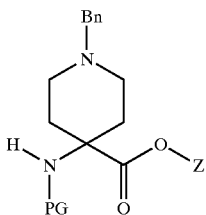
(1s)

in which Z comprises the Wang or Merrifield resin; $L^1$ comprises —O—; $L^2$ comprises —CH$_2$—; $L^3$ comprises —CH$_2$CH$_2$—; $L^4$ comprises a direct single bond; E comprises —CH—; K comprises —N—; PG comprises hydrogen, benzyloxycarbonyl, 9-fluorenylmethoxycarbonyl, or t-butoxycarbonyl; $R^1$ comprises hydrogen; and $R^2$ comprises benzyl.

In a ninth embodiment of the fourth aspect, the amino acid templates of the present invention, in which Z comprises the Wang resin, are represented by the formulae:

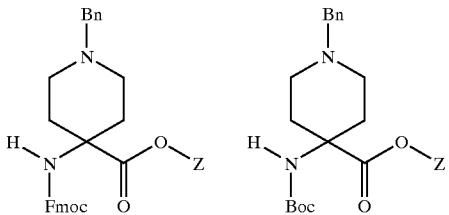

In an tenth embodiment of the fourth aspect, the amino acid templates of the present invention, in which Z comprises the Merrifield resin, are represented by the formulae:

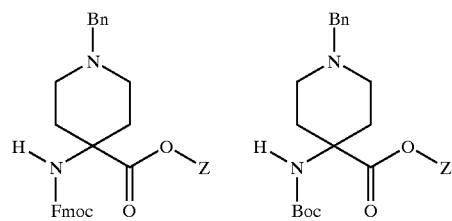

In a eleventh embodiment of the fourth aspect, the amino acid templates of the present invention are represented by formula (1t):

(1t)

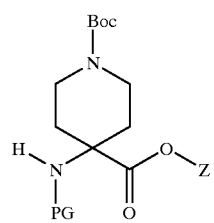

in which Z comprises the Wang or Merrifield resin; $L^1$ comprises —O—; L comprises —CH$_2$—; $L^3$ comprises —CH$_2$CH$_2$—; $L^4$ comprises a direct single bond; E comprises —CH—; K comprises —N—; PG comprises hydrogen, benzyloxycarbonyl, 9-fluorenylmethoxycarbonyl, or t-butoxycarbonyl; $R^1$ comprises hydrogen; and $R^2$ comprises benzyloxycarbonyl.

In a twelfth embodiment of the fourth aspect, the amino acid templates of the present invention, in which Z comprises the Wang resin, are represented by the formula:

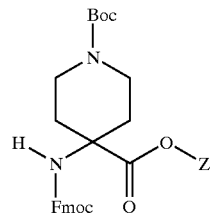

In an thirteenth embodiment of the fourth aspect, the amino acid templates of the present invention, in which Z comprises the Merrifield resin, are represented by the formula:

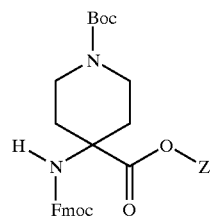

In a fifth aspect, the amino acid templates of the present invention are represented by formula (1v):

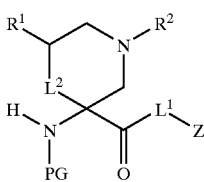

(1v)

in which Z comprises the Merrifield resin, hydroxymethyl resin, Wang resin, or aminomethyl resin; E comprises —CH—; K comprises N—; $L^1$ comprises O— or N—; $L^2$ comprises $CH_2$—, —$CH_2CH_2$—, or a direct single bond; $L^3$ comprises —$CH_2$—; $L^4$ comprises $CH_2$—; PG comprises hydrogen, benzyloxycarbonyl, 9-fluorenylmethoxycarbonyl, or t-butoxycarbonyl; $R^1$ comprises alkyl, alkenyl, alkynyl, cycloalkyl, heterocyclyl, aryl, heteroaryl, hydrogen, halo, —O—$G^3$, —$G^3$, or —N($G^3$)$G^4$ where $G^3$ and $G^4$ independently represent groups comprising

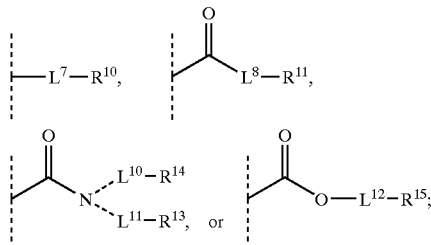

where $L^7$, $L^8$, $L^{10}$, $L^{11}$, $L^{12}$ independently represent groups comprising alkylene, alkenylene, alkynylene, cycloalkylene, cycloalkenylene, arylene, heterocyclylene, heteroarylene, fused cycloalkylarylene, fused cycloakylheteroarylene, fused heterocyclylarylene, fused heterocyclylheteroarylene, or a direct bond; and $R^{10}$, $R^{11}$, $R^{13}$, $R^{14}$, $R^{15}$ independently represent a group comprising alkyl, alkenyl, alkynyl, cycloalkyl, cycloalkenyl, heterocyclyl, heteroaryl, aryl, fused cycloalkylaryl, fused cycloakylheteroaryl, fused heterocyclylaryl, fused heterocyclylheteroaryl, —$NR^{18}R^{19}$, —$OR^{18}$, —$SR^{18}$, or hydrogen, where $R^{18}$ and $R^{19}$ independently represent groups comprising hydrogen, alkyl, alkynyl, alkenyl, cycloalkyl, cycloalkenyl, aryl, heterocyclyl, or heteroaryl; and $R^2$ comprises alkyl, alkenyl, alkynyl, cycloalkyl, heterocyclyl, aryl, heteroaryl, hydrogen, or —$G^5$, where $G^5$ represents a group comprising

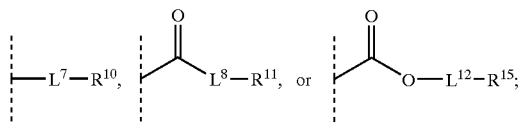

where $L^7$, $L^8$, $L^{12}$ independently represent groups comprising alkylene, alkenylene, alkynylene, cycloalkylene, cycloalkenylene, arylene, heterocyclylene, heteroarylene, fused cycloalkylarylene, fused cycloakylheteroarylene, fused heterocyclylarylene, fused heterocyclylheteroarylene, or a direct bond; and $R^{10}$, $R^{11}$, $R^{15}$ independently represent groups comprising alkyl, alkenyl, alkynyl, cycloalkyl, cycloalkenyl, heterocyclyl, heteroaryl, aryl, fused cycloalkylaryl, fused cycloakylheteroaryl, fused heterocyclylaryl, fused heterocyclylheteroaryl, —$NR^{18}R^{19}$, —$OR^{18}$, —$SR^{18}$, or hydrogen, where $R^{18}$ and $R^{19}$ independently represent groups comprising hydrogen, alkyl, alkynyl, alkenyl, cycloalkyl, cycloalkenyl, aryl, heterocyclyl, or heteroaryl.

In an embodiment of the fifth aspect, the amino acid templates of the present invention are represented by formula (1v):

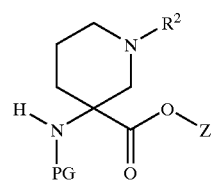

(1v)

in which Z comprises the Wang or Merrifield resin; $L^1$ comprises —O—; $L^2$ comprises $CH_2CH_2$—; $L^3$ comprises —$CH_2$—; $L^4$ comprises $CH_2$—; E comprises CH—; K comprises N—; PG comprises hydrogen, benzyloxycarbonyl, 9-fluorenylmethoxycarbonyl, or t-butoxycarbonyl; $R^1$ comprises hydrogen; and $R^2$ comprises alkyl, alkenyl, alkynyl, cycloalkyl, heterocyclyl, aryl, heteroaryl, hydrogen, or —$G^5$, where Gs represents a group comprising

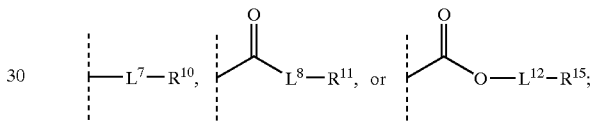

where $L^7$, $L^8$, $L^{12}$ independently represent groups comprising alkylene, alkenylene, alkynylene, cycloalkylene, cycloalkenylene, arylene, heterocyclylene, heteroarylene, fused cycloalkylarylene, fused cycloakylheteroarylene, fused heterocyclylarylene, fused heterocyclylheteroarylene, or a direct bond; and $R^{10}$, $R^{11}$, $R^{15}$ independently represent groups comprising alkyl, alkenyl, alkynyl, cycloalkyl, cycloalkenyl, heterocyclyl, heteroaryl, aryl, fused cycloalkylaryl, fused cycloakylheteroaryl, fused heterocyclylaryl, fused heterocyclylheteroaryl, —$NR^{18}R^{19}$, —$OR^{18}$, —$SR^{18}$, or hydrogen, where $R^{18}$ and $R^{19}$ independently represent groups comprising hydrogen, alkyl, alkynyl, alkenyl, cycloalkyl, cycloalkenyl, aryl, heterocyclyl, or heteroaryl.

In a second embodiment of the fifth aspect, the amino acid templates of the present invention are represented by formula (1w):

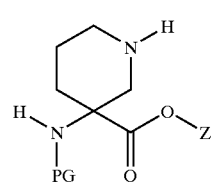

(1w)

in which Z comprises the Wang or Merrifield resin; $L^1$ comprises —O—; $L^2$ comprises —$CH_2CH_2$—; $L^3$ comprises —$CH_2$—; $L^4$ comprises —$CH_2$—; E comprises —CH—; K comprises —N—; PG comprises hydrogen, benzyloxycarbonyl, 9-fluorenylmethoxycarbonyl, or t-butoxycarbonyl; and $R^1$ and $R^2$ independently comprise hydrogen.

In a third embodiment of the fifth aspect, the amino acid templates of the present invention, in which Z comprises the Wang resin, are represented by the formulae:

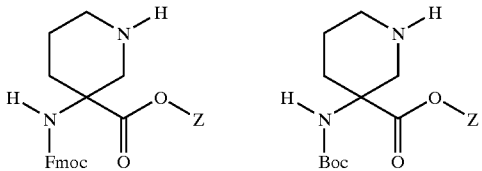

In a fourth embodiment of the fifth aspect, the amino acid templates of the present invention, in which Z comprises the Merrifield resin, are represented by the formulae:

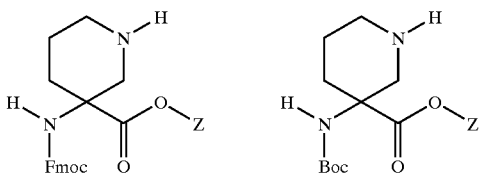

In a fifth embodiment of the fifth aspect, the amino acid templates of the present invention are represented by formula (1x):

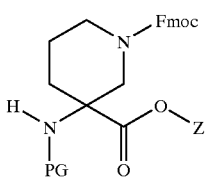

(1x)

in which Z comprises the Wang or Merrifield resin; $L^1$ comprises O—; $L^2$ comprises $CH_2CH_2$—; $L^3$ comprises —$CH_2$—; $L^4$ comprises —$CH_2$—; E comprises —CH—; K comprises —N—; PG comprises hydrogen, benzyloxycarbonyl, 9-fluorenylmethoxycarbonyl, or t-butoxycarbonyl; $R^1$ comprises hydrogen; and $R^2$ comprises 9-fluorenylmethoxycarbonyl.

In a sixth embodiment of the fifth aspect, the amino acid templates of the present invention, in which Z comprises the Wang resin, are represented by the formulae:

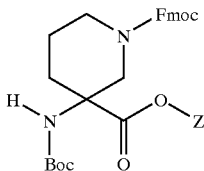

In an seventh embodiment of the fifth aspect, the amino acid templates of the present invention, in which Z comprises the Merrifield resin, are represented by the formulae:

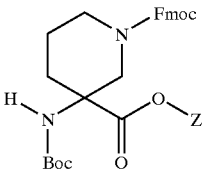

In a eighth embodiment of the fifth aspect, the amino acid templates of the present invention are represented by formula (1y):

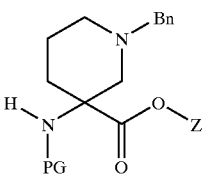

(1y)

in which Z comprises the Wang or Merrifield resin; $L^1$ comprises O—; $L^2$ comprises $CH_2CH_2$—; $L^3$ comprises —$CH_2$—; $L^4$ comprises —$CH_2$—; E comprises —CH—; K comprises —N—; PG comprises hydrogen, benzyloxycarbonyl, 9-fluorenylmethoxycarbonyl, or t-butoxycarbonyl; $R^1$ comprises hydrogen; and $R^2$ comprises benzyl.

In a ninth embodiment of the fifth aspect, the amino acid templates of the present invention, in which Z comprises the Wang resin, are represented by the formulae:

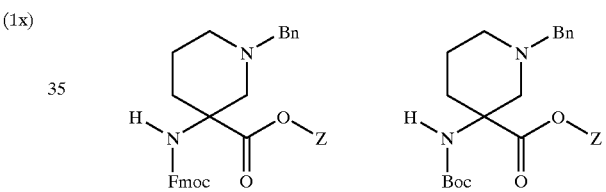

In an tenth embodiment of the fifth aspect, the amino acid templates of the present invention, in which Z comprises the Merrifield resin, are represented by the formulae:

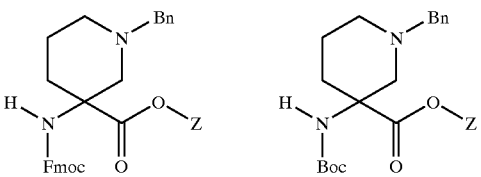

In a eleventh embodiment of the fifth aspect, the amino acid templates of the present invention are represented by formula (1z):

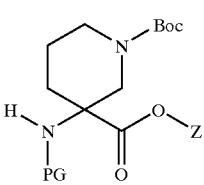

(1z)

in which Z comprises the Wang or Merrifield resin; $L^1$ comprises —O—; $L^2$ comprises —$CH_2CH_2$—; $L^3$ comprises —$CH_2$—; $L^4$ comprises —$CH_2$—; E comprises —CH—; K comprises —N—; PG comprises hydrogen, benzyloxycarbonyl, 9-fluorenylmethoxycarbonyl, or t-butoxycarbonyl; $R^1$ comprises hydrogen; and $R^2$ comprises benzyloxycarbonyl.

In a twelfth embodiment of the fifth aspect, the amino acid templates of the present invention, in which Z comprises the Wang resin, are represented by the formulae:

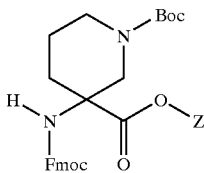

In an thirteenth embodiment of the fifth aspect, the amino acid templates of the present invention, in which Z comprises the Merrifield resin, are represented by the formulae:

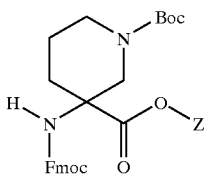

In a sixth aspect, the present invention provides quaternary amino acids which are represented by the formula:

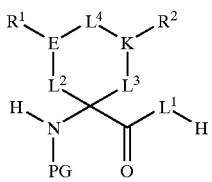

(2)

in which the symbol $L^1$ represents a divalent linkage comprising a divalent group of the formula O—, —NH—, or —O—$CH_2$—$C_6H_4$—$CH_2$O—. Preferably, $L^1$ comprises O— or —NH—.

The symbol $L^2$ represents a divalent linkage comprising an alkylene, alkenylene, alkynylene, or a direct single bond. In preferred embodiments, $L^2$ comprises methylene, ethylene, or a direct single bond. More preferably, $L^2$ comprises $CH_2$—, —$CH_2CH_2$—, or a direct single bond.

The symbol $L^3$ represents a divalent linkage comprising an alkylene, alkenylene, alkynylene, or a direct single bond. In preferred embodiments, $L^2$ comprises methylene, ethylene, or a direct single bond. More preferably, $L^3$ comprises —$CH_2$—, —$CH_2CH_2$—, or a direct single bond.

The symbol $L^4$ represents a divalent linkage comprising alkylene, —O—, —S—, —C(O)—, —S(O)—, —S(O)$_2$—,

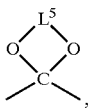

or a direct single or double bond, in which $L^5$ comprises —$CH_2CH_2$— or $CH_2CH_2CH_2$—. In preferred embodiments, $L^4$ comprises lower alkylene, —O—, —S—, —C(O)—, —S(O)—, —S(O)$_2$—,

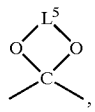

or a direct single bond. More preferably, $L^4$ comprises —$CH_2$—, —O—, —S—, —C(O)—, —S(O)—, —S(O)$_2$—,

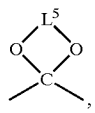

or a direct single bond.

The letter E represents a divalent linkage comprising —N—, —CH—, or —C=. In preferred embodiments, E comprises —N— or —CH—.

The letter K represents a divalent linkage comprising —N—, —CH—, or —C=. In preferred embodiments, K comprises —N— or —CH—.

Preferably, the groups $L^2$, $L^3$, $L^4$, E, and K are chosen to comprise a ring with 3 to 8 members.

The symbol PG represents a group comprising a hydrogen or an amino protecting group. In preferred embodiments, PG comprises hydrogen, benzyloxycarbonyl, 9-fluorenylmethoxycarbonyl, allyloxycarbonyl, phenyl, benzyl or t-butoxycarbonyl. More preferably, PG comprises hydrogen, benzyloxycarbonyl, 9-fluorenylmethoxycarbonyl, or t-butoxycarbonyl.

The symbol $R^1$ represents a group comprising alkyl, alkenyl, alkynyl, cycloalkyl, heterocyclyl, aryl, heteroaryl, hydrogen, halo, —O—$G^3$, —O—$G^4$, —$G^3$, —$G^4$, or —N($G^3$)$G^4$, in which $G^3$ and $G^4$ independently represent groups comprising

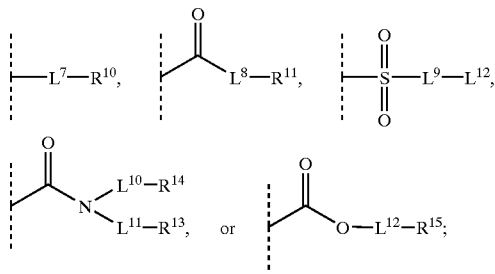

where $L^7$, $L^8$, $L^9$, $L^{10}$, $L^{11}$ $L^{12}$ independently represent groups comprising alkylene, alkenylene, alkynylene, cycloalkylene, cycloalkenylene, arylene, heterocyclylene, heteroarylene, fused cycloalkylarylene, fused cycloakylheteroarylene, fused heterocyclylarylene, fused heterocyclylheteroarylene, or a direct bond; and $R^{10}$, $R^{11}$, $R^{12}$, $R^{13}$, $R^{14}$, $R^{15}$ independently represent groups comprising alkyl, alkenyl, alkynyl, cycloalkyl, cycloalkenyl, heterocyclyl, heteroaryl, aryl, fused cycloalkylaryl, fused cycloakylheteroaryl, fused heterocyclylaryl, fused heterocyclylheteroaryl, —$NR^{18}R^{19}$, —$OR^{18}$, —$SR^{18}$, or hydrogen, where $R^{18}$ and $R^{19}$ independently represent groups comprising hydrogen, alkyl, alkynyl, alkenyl, cycloalkyl, cycloalkenyl, aryl, heterocyclyl, or heteroaryl. In preferred embodiments, $R^1$ comprises alkyl, alkenyl, alkynyl, cycloalkyl, heterocyclyl, aryl, heteroaryl, hydrogen, halo, —O—$G^3$, —O—$G^4$—$G^3$, —$G^4$, or —N($G^3$)$G^4$, in which $G^3$ and $G^4$ independently represent groups comprising

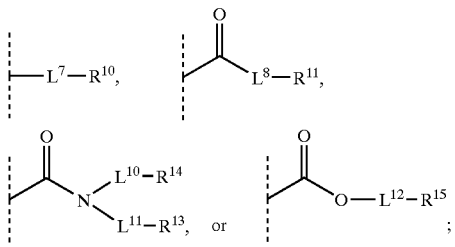

where $L^7$, $L^8$, $L^{10}$, $L^{11}$, $L^{12}$ independently represent groups comprising alkylene, alkenylene, alkynylene, cycloalkylene, cycloalkenylene, arylene, heterocyclylene, heteroarylene, fused cycloalkylarylene, fused cycloakylheteroarylene, fused heterocyclylarylene, fused heterocyclylheteroarylene, or a direct bond; and $R^{10}$, $R^{11}$, $R^{13}$, $R^{14}$, $R^{15}$ independently represent groups comprising alkyl, alkenyl, alkynyl, cycloalkyl, cycloalkenyl, heterocyclyl, heteroaryl, aryl, fused cycloalkylaryl, fused cycloakylheteroaryl, fused heterocyclylaryl, fused heterocyclylheteroaryl, —$NR^{18}R^{19}$, —$OR^{18}$, —$SR^{18}$, or hydrogen, where $R^{18}$ and $R^{19}$ independently represent groups comprising hydrogen, alkyl, alkynyl, alkenyl, cycloalkyl, cycloalkenyl, aryl, heterocyclyl, or heteroaryl. More preferably, $R^1$ comprises hydrogen, halo, and —$OG^3$ where $G^3$ comprises

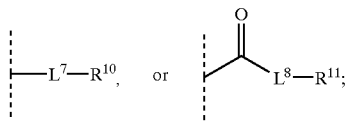

where $L^7$, $L^8$ independently represent groups comprising alkylene, alkenylene, alkynylene, cycloalkylene, cycloalkenylene, arylene, heterocyclylene, heteroarylene, fused cycloalkylarylene, fused cycloakylheteroarylene, fused heterocyclylarylene, fused heterocyclylheteroarylene, or a direct bond; and $R^{10}$, $R^{11}$ independently represent groups comprising alkyl, alkenyl, alkynyl, cycloalkyl, cycloalkenyl, heterocyclyl, heteroaryl, aryl, fused cycloalkylaryl, fused cycloakylheteroaryl, fused heterocyclylaryl, fused heterocyclylheteroaryl, —$NR^{18}R^{19}$, $OR^{18}$, $SR^{18}$, or hydrogen, where $R^{18}$ and $R^{19}$ independently represent groups comprising hydrogen, alkyl, alkynyl, alkenyl, cycloalkyl, cycloalkenyl, aryl, heterocyclyl, or heteroaryl. Even more preferably, $R^1$ comprises hydrogen, halogen, —OH, —O-tert-butyl, or —O-benzyl.

The symbol $R^2$ represents a group comprising alkyl, alkenyl, alkynyl, cycloalkyl, heterocyclyl, aryl, heteroaryl, hydrogen, halo, —O—$G^3$, —O—$G^4$, —$G^3$, —$G^4$, or —$N(G^3)G^4$, in which $G^3$ and $G^4$ independently represent groups comprising

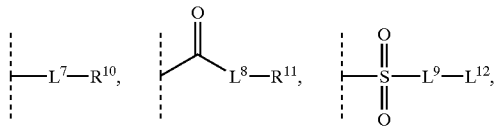

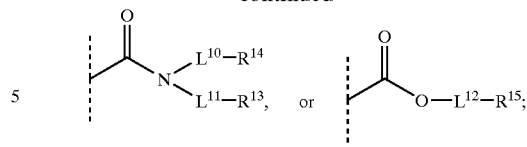

where $L^7$, $L^8$, $L^9$, $L^{10}$, $L^{11}$, $L^{12}$ independently represent groups comprising alkylene, alkenylene, alkynylene, cycloalkylene, cycloalkenylene, arylene, heterocyclylene, heteroarylene, fused cycloalkylarylene, fused cycloakylheteroarylene, fused heterocyclylarylene, fused heterocyclylheteroarylene, or a direct bond; and, $R^{10}$, $R^{11}$, $R^{12}$, $R^{13}$, $R^{14}$, $R^{15}$ independently represent groups comprising alkyl, alkenyl, alkynyl, cycloalkyl, cycloalkenyl, heterocyclyl, heteroaryl, aryl, fused cycloalkylaryl, fused cycloakylheteroaryl, fused heterocyclylaryl, fused heterocyclylheteroaryl, —$NR^{18}R^{19}$, —$OR^{18}$, —$SR^{18}$, or hydrogen, where $R^{18}$ and $R^{19}$ independently represent hydrogen, alkyl, alkynyl, alkenyl, cycloalkyl, cycloalkenyl, aryl, heterocyclyl, or heteroaryl. In preferred embodiments, $R^2$ comprises alkyl, alkenyl, alkynyl, cycloalkyl, heterocyclyl, aryl, heteroaryl, hydrogen, halo, —O—$G^3$, —O—$G^4$, —$G^3$, —$G^4$, or —$N(G^3)G^4$, in which $G^3$ and $G^4$ independently represent groups comprising

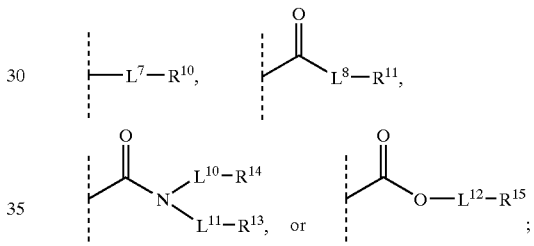

where $L^7$, $L^8$, $L^{10}$, $L^{11}$, $L^{12}$ independently represent groups comprising alkylene, alkenylene, alkynylene, cycloalkylene, cycloalkenylene, arylene, heterocyclylene, heteroarylene, fused cycloalkylarylene, fused cycloakylheteroarylene, fused heterocyclylarylene, fused heterocyclylheteroarylene, or a direct bond; and $R^{10}$, $R^{11}$, $R^{13}$, $R^{14}$, $R^{15}$ independently represent groups comprising alkyl, alkenyl, alkynyl, cycloalkyl, cycloalkenyl, heterocyclyl, heteroaryl, aryl, fused cycloalkylaryl, fused cycloakylheteroaryl, fused heterocyclylaryl, fused heterocyclylheteroaryl, —$NR^{18}R^{19}$, —$OR^{18}$, —$SR^{18}$, or hydrogen, where $R^{18}$ and $R^{19}$ independently represent groups comprise hydrogen, alkyl, alkynyl, alkenyl, cycloalkyl, cycloalkenyl, aryl, heterocyclyl, or heteroaryl. More preferably, $R^2$ comprises alkyl, alkenyl, alkynyl, cycloalkyl, heterocyclyl, aryl, heteroaryl, hydrogen, or 5 in which $G^5$ comprises

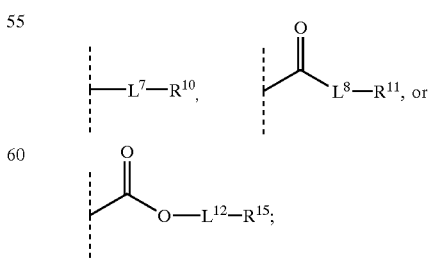

where $L^7$, $L^8$, $L^{12}$ independently represent groups comprising alkylene, alkenylene, alkynylene, cycloalkylene, cycloalkenylene, arylene, heterocyclylene, heteroarylene, fused cycloalkylarylene, fused cycloakylheteroarylene, fused heterocyclylarylene, fused heterocyclylheteroarylene, or a direct bond; and $R^{10}$, $R^{11}$, $R^{15}$ independently represent groups comprising alkyl, alkenyl, alkynyl, cycloalkyl, cycloalkenyl, heterocyclyl, heteroaryl, aryl, fused cycloalkylaryl, fused cycloakylheteroaryl, fused heterocyclylaryl, fused heterocyclylheteroaryl, —$NR^{18}R^{19}$, —$OR^{18}$, —$SR^{18}$, or hydrogen, where $R^{18}$ and $R^{19}$ independently represent groups comprising hydrogen, alkyl, alkynyl, alkenyl, cycloalkyl, cycloalkenyl, aryl, heterocyclyl, or heteroaryl. Even more preferably, $R^2$ comprises hydrogen, benzyl, benzyloxycarbonyl, 9-fluorenylmethoxycarbonyl, or t-butoxycarbonyl.

$R^1$ and $R^2$ may be taken together to constitute a cycloalkyl or heterocyclyl ring, or, where $L^4$ comprises a direct bond, $R^1$ and $R^2$ may be taken together to constitute a fused aryl or heteroaryl ring.

In the compounds of Formula 1, the various functional groups represented should be understood to have a point of attachment at the functional group having the hyphen. In other words, in the case of —O—$G^3$, it should be understood that the point of attachment is the oxygen atom; an example would be tert-butoxy. In the case of a group such as —$CO_2$—$L^{12}$—$R^{15}$, the point of attachment is the carbonyl carbon.

Certain compounds of the present invention possess asymmetric carbon atoms (optical centers); the racemates, diastereomers, geometric isomers and individual isomers are all intented to be encompassed within the scope of the present invention.

The compounds of the present invention may also contain unnatural proportions of atomic isotopes at one or more of the atoms that constitute such compounds. For example, the compounds may be radiolabeled with radioactive isotopes, such as, for example, tritium ($^3H$), iodine-125 ($^{125}I$) or carbon-14 ($^{14}C$). All isotopic variations of the compounds of the present invention, whether radioactive or not, are intended to be encompassed within the scope of the present invention.

As used herein, the term "optionally" means that the subsequently described event(s) may or may not occur, and includes both event(s) which occur and events that do not occur.

As used herein, the term "lower" refers to a group having between one and six carbons.

As used herein, the term "alkyl" refers to a straight or branched chain hydrocarbon having one to ten carbon atoms, optionally substituted with substituents and with multiple degrees of substitution being allowed. Examples of "alkyl" as used herein include, but are not limited to, methyl, n-butyl, n-pentyl, isobutyl, and isopropyl, and the like.

As used herein, the term "alkylene" refers to a straight or branched chain divalent hydrocarbon radical having one to ten carbon atoms, optionally substituted with substituents and with multiple degrees of substitution being allowed. Examples of "alkylene" as used herein include, but are not limited to, methylene, ethylene, and the like.

As used herein, the term "halogen" or "halo" includes iodine, bromine, chlorine and fluorine.

As used herein, the term "alkenyl" refers to a hydrocarbon radical having from two to ten carbons and at least one carbon-carbon double bond, optionally substituted with substituents and with multiple degrees of substitution being allowed.

As used herein, the term "alkenylene" refers to a straight or branched chain divalent hydrocarbon radical having from two to ten carbon atoms and one or more carbon-carbon double bonds, optionally substituted with substituents and with multiple degrees of substitution being allowed. Examples of "alkenylene" as used herein include, but are not limited to, ethene-1,2-diyl, propene-1,3-diyl, and the like.

As used herein, the term "alkynyl" refers to a hydrocarbon radical having from two to ten carbons and at least one carbon-carbon triple bond, optionally substituted with substituents and with multiple degrees of substitution being allowed.

As used herein, the term "alkynylene" refers to a straight or branched chain divalent hydrocarbon radical having from two to ten carbon atoms and one or more carbon-carbon triple bonds, optionally substituted with substituents and with multiple degrees of substitution being allowed. Examples of "alkynylene" as used herein include, but are not limited to, ethyne-1,2-diyl, propyne-1,3-diyl, and the like.

As used herein, "cycloalkyl" refers to an alicyclic hydrocarbon group with one or more degrees of unsaturation, having from three to twelve carbon atoms, optionally substituted with substituents and with multiple degrees of substitution being allowed. Examples of "cycloalkyl" as used herein include, but are not limited to, cyclopropyl, cyclobutyl, cyclopentyl, cyclohexyl, cycloheptyl, or cyclooctyl, and the like.

As used herein, the term "cycloalkylene" refers to an nonaromatic alicyclic divalent hydrocarbon radical having from three to twelve carbon atoms and optionally possessing one or more degrees of unsaturation, optionally substituted with substituents and with multiple degrees of substitution being allowed. Examples of "cycloalkylene" as used herein include, but are not limited to, cyclopropyl-1,1-diyl, cyclopropyl-1,2-diyl, cyclobutyl-1,2-diyl, cyclopentyl-1,3-diyl, cyclohexyl-1,4-diyl, cycloheptyl-1,4-diyl, or cyclooctyl-1,5-diyl, and the like.

As used herein, the term "heterocyclic" or the term "heterocyclyl" refers to a three to twelve-membered heterocyclic ring optionally having one or more degrees of unsaturation containing one or more heteroatomic substitutions selected from S, SO, $SO_2$, O, or N, optionally substituted with substituents and with multiple degrees of substitution being allowed. Such a ring may be optionally fused to one or more of another "heterocyclic" ring(s) or cycloalkyl ring(s). Examples of "heterocyclic" include, but are not limited to, tetrahydrofuran, 1,4-dioxane, 1,3-dioxane, piperidine, pyrrolidine, morpholine, piperazine, and the like.

As used herein, the term "heterocyclylene" refers to a three to twelve-membered heterocyclic ring diradical optionally having one or more degrees of unsaturation containing one or more heteroatoms selected from S, SO, $SO_2$, O, or N, optionally substituted with substituents and with multiple degrees of substitution being allowed. Such a ring may be optionally fused to one or more benzene rings or to one or more of another "heterocyclic" rings or cycloalkyl rings. Examples of "heterocyclylene" include, but are not limited to, tetrahydrofuran-2,5-diyl, morpholine-2,3-diyl, pyran-2,4-diyl, 1,4-dioxane-2,3-diyl, 1,3-dioxane-2,4-diyl, piperidine-2,4-diyl, piperidine-1,4-diyl, pyrrolidine-1,3-diyl, morpholine-2,4-diyl, piperazine-1,4-dyil, and the like.

As used herein, the term "aryl" refers to a benzene ring or to an optionally substituted benzene ring system fused to one or more optionally substituted benzene rings, optionally substituted with substituents and with multiple degrees of substitution being allowed. Examples of aryl include, but are not limited to, phenyl, 2-naphthyl, 1-naphthyl, 1-anthracenyl, and the like.

As used herein, the term "arylene" refers to a benzene ring diradical or to a benzene ring system diradical fused to one or more optionally substituted benzene rings, optionally substituted with substituents and with multiple degrees of substitution being allowed. Examples of "arylene" include, but are not limited to, benzene-1,4-diyl, naphthalene1,8-diyl, and the like.

As used herein, the term "heteroaryl" refers to a five- to seven-membered aromatic ring, or to a polycyclic heterocyclic aromatic ring, containing one or more nitrogen, oxygen, or sulfur heteroatoms, where N-oxides and sulfur monoxides and sulfur dioxides are permissible heteroaromatic substitutions, optionally substituted with substituents and with multiple degrees of substitution being allowed. For polycyclic aromatic ring systems, one or more of the rings may contain one or more heteroatoms. Examples of "heteroaryl" used herein are furan, thiophene, pyrrole, imidazole, pyrazole, triazole, tetrazole, thiazole, oxazole, isoxazole, oxadiazole, thiadiazole, isothiazole, pyridine, pyridazine, pyrazine, pyrimidine, quinoline, isoquinoline, benzofuran, benzothiophene, indole, and indazole, and the like.

As used herein, the term "heteroarylene" refers to a five- to seven-membered aromatic ring diradical, or to a polycyclic heterocyclic aromatic ring diradical, containing one or more nitrogen, oxygen, or sulfur heteroatoms, where N-oxides and sulfur monoxides and sulfur dioxides are permissible heteroaromatic substitutions, optionally substituted with substituents and with multiple degrees of substitution being allowed. For polycyclic aromatic ring system diradicals, one or more of the rings may contain one or more heteroatoms. Examples of "heteroarylene" used herein are furan-2,5-diyl, thiophene-2,4-diyl, 1,3,4-oxadiazole-2,5-diyl, 1,3,4-thiadiazole-2,5-diyl, 1,3-thiazole-2,4-diyl, 1,3-thiazole-2,5-diyl, pyridine-2,4-diyl, pyridine-2,3-diyl, pyridine-2,5-diyl, pyrimidine-2,4-diyl, quinoline-2,3-diyl, and the like.

As used herein, the term "fused cycloalkylaryl" refers to a cycloalkyl group fused to an aryl group, the two having two atoms in common. Examples of "fused cycloalkylaryl" used herein include 1-indanyl, 2-indanyl, 1-(1,2,3,4-tetrahydronaphthyl), and the like.

As used herein, the term "fused cycloalkylheteroaryl" refers to a cycloalkyl group fused to an heteroaryl group, the two having two atoms in common. Examples of "fused cycloalkylheteroaryl" used herein include 5-aza-1-indanyl and the like.

As used herein, the term "fused heterocyclylaryl" refers to a heterocyclyl group fused to an aryl group, the two having two atoms in common. Examples of "fused heterocyclylaryl" used herein include 2,3-benzodioxin and the like.

As used herein, the term "fused heterocyclylheteroaryl" refers to a heterocyclyl group fused to an heteroaryl group, the two having two atoms in common. Examples of "fused heterocyclylheteroaryl" used herein include 3,4-methylenedioxypyridine and the like.

As used herein, the term "direct bond", where part of a structural variable specification, refers to the direct joining of the substituents flanking (preceding and succeeding) the variable. The term "direct single bond" refers to the direct joining of substituents flanking the variable through a single bond. The term "direct double bond" refers to refers to the direct joining of substituents flanking the variable through a double bond.

In the above schemes, "PG" represents an amino protecting group. The term "amino protecting group" as used herein refers to substituents of the amino group commonly employed to block or protect the amino functionality while reacting other functional groups on the compound. Examples of such amino-protecting groups include the formyl group, the trityl group, the phthalimido group, the trichloroacetyl group, the chloroacetyl, bromoacetyl and iodoacetyl groups, urethane-type blocking groups such as benzyloxycarbonyl ("CBZ"), 4-phenylbenzyloxycarbonyl, 2-methylbenzyloxycarbonyl, 4-methoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxy-carbonyl, 2-(4-xenyl)iso-propoxycarbonyl, 1,1-diphenyleth-1-yloxycarbonyl, I, I-diphenylprop-1-yloxycarbonyl, 2-phenylprop-2-yloxycarbonyl, 2-(p-toluyl)prop-2-yloxycarbonyl, cyclopentanyloxycarbonyl, I-methylcyclopentanyloxycarbonyl, cyclohexanyloxycarbonyl, 1-methylcyclohexanyloxycarbonyl, 2-methylcyclohexanyloxycarbonyl, 2-(4-toluylsulfonyl)ethoxycarbonyl, 2(methylsulfonyl)ethoxycarbonyl, 2-(triphenylphosphino)ethoxycarbonyl, 9-fluorenylmethoxycarbonyl ("FMOC"), t-butoxycarbonyl ("BOC"), 2-(trimethylsilyl)ethoxycarbonyl, allyloxycarbonyl, 1-(trimethylsilylmethyl)prop-1-enyloxycarbonyl, 5-benzisoxalylmethoxycarbonyl, 4-acetoxybenzyloxycarbonyl, 2,2,2-trichloroethoxycarbonyl, 2-ethynyl-2-propoxycarbonyl, cyclopropylmethoxycarbonyl, 4-(decyloxy)benzyloxycarbonyl, isobomyloxycarbonyl, 1-piperidyloxycarbonyl and the like; the benzoylmethylsulfonyl group, the 2-(nitro)phenylsulfenyl group, the diphenylphosphine oxide group and like amino-protecting groups. The species of amino-protecting group employed is not critical so long as the derivatized amino group is stable to the condition of subsequent reaction(s) on other positions of the compound of formula 1 and can be removed at the desired point without disrupting the remainder of the molecule. Preferred amino-protecting groups are the t-butoxycarbonyl, 9-fluorenylmethoxycarbonyl, and the benzyloxycarbonyl groups. Similar amino-protecting groups used in the cephalosporin, penicillin and peptide art are also embraced by the above terms. Further examples of groups referred to by the above terms are described by J. W. Barton, "Protective Groups In Organic Chemistry", J. G. W. McOmie, Ed., Plenum Press, New York, N.Y., 1973, Chapter 2, and T. W. Greene, "Protective Groups in Organic Synthesis", John Wiley and Sons, New York, N.Y., 1981, Chapter 7. The related term "protected amino" defines an amino group substituted with an amino-protecting group discussed above.

As used herein, the term "Chemical Library" or "array" comprises an intentionally created collection of differing molecules which can be prepared synthetically and screened for biological activity in a variety of different formats (e.g., libraries of soluble molecules, libraries of molecules bound to a solid support).

The polymeric support referred to above as "Z" may be any known solid support having hydroxyl or amino functionality which enables the protected amino acid structure to be covalently bonded thereto.

As used herein the term "solid support(s)" includes an insoluble substrate that has been appropriately derivatized such that a chemical module can be attached to the surface of the substrate through standard chemical methods. Solid supports include, but are not limited to, beads and particles, such as peptide synthesis resins. See, for example, Merrifield, B., *J Am. Chem. Soc.* 85:2149–2154 (1963); U.S. Pat. No. 4,631,211; Geysenetal., *Proc. Natl. Acad. Sci. USA* 81:3998–4002 (1984). Solid supports can be comprised of many materials, limited primarily by the capacity of the material to be functionalized through synthetic methods. Examples of such materials include, but are not limited to, polymers, plastics, resins, polysaccharides, silicon or silica based materials, and membranes. Preferred resins include Merrifield resin, hydroxymethyl resin, Wang resin, aminomethyl resin (all available from various suppliers including, Advanced ChemTech, Novabiochem, etc.), SASRIN resin (a polystyrene resin available from Bachem Bioscience, Switzerland), and TentaGel S AC, TentaGel PHB, or TentaGel S $NH_2$ resin (polystyrene-polyethylene glycol copolymer resins available from Rapp Polymere, Tubingen, Germany).

The solid support can be purchased with suitable functionality already present such that a chemical module can be attached to the support surface (e.g., Novabiochem, Bachem Bioscience, Rapp Polymere). Alternatively, the solid support can be chemically modified such that a chemical module can be attached to the support surface. (Grant, "Synthetic Peptides: A User's Guide," W. H. Freeman and Co (1992); Hermkens et al, *Tetrahedron* 52:4527–4554 (1996)). The choice of functionality used for attaching a molecule to the solid support will depend on the nature of the compound to be synthesized and the type of solid support. Examples of functionality present on the solid support that can be used to attach a chemical module include, but are not limited to, alkyl or aryl halides, aldehydes, alcohols, ketones, amines, sulfides, carboxyl groups, aldehyde groups, and sulfonyl groups.

Preferably, the functional group on the solid support that permits the attachment of a chemical module will be an alcohol, an amine, an aldehyde, or an acid group. Examples of chemical reactions that can be used to attach a chemical module to the support include, but are not limited to, nucleophilic displacement of a halide or other leaving group, etherification of an alcohol, esterification of an alcohol, amidation of an amine, acetylization of an aldehyde, and ketalization of a ketone. Preferably, the reaction used to attach the chemical module to the solid support will be an esterification of an alcohol, an amidation of an amine, or an acetylization of an aldehyde. For the attachment of certain chemical modules to the solid support, masking of functionality that is not involved in the attachment process, but that is incompatible with the mode of attachment, may be necessary. Prior to the coupling reaction, the amino groups are "protected" through standard methodology for protecting amino groups in the peptide art utilizing the amino protecting groups set forth above.

Abbreviations used are as follows:
Boc=t-butoxycarbonyl
Cbz=benzyloxycarbonyl
DIC=diisopropylcarbodiimide
DCC=dicyclohexylcarbodiimide
DCM=dichloromethane
DIEA=disopropylethylamine
DMAP=N,N-dimethylaminopyridine
DMF=N,N-dimethylformamide
DMSO=dimethylsulfoxide
EDC=1-ethyl-3-(3-dimethylaminopropyl)-carbodiimide hydrochloride
EtOAc=ethyl acetate
Fmoc=9-fluorenylmethoxycarbonyl
g=gram
h=hour
HOBt=1-hydroxybenzotriazole
L=liter
M=molar
MeOH=methanol
mg=milligram
min=minute
ml=milliliter
mM=millimolar
mmol=millimole
mol=mole
N=normal
NMM=N-methylmorpholine, 4-methylmorpholine
NMR=nuclear magnetic resonance spectroscopy
PMA=phosphomolybedic acid
PPTS=pyridinium p-tolunesulfonate
rt=room temperature
TEA=triethylamine
TFA=trifluoroacetic acid
THF=tetrahydrofuran
THP=tetrahydropyranyl
TMSCI=trimethylsilyl chloride The supported amino acids of the present invention are useful as templates in the synthesis of peptides and of amino acid containing compounds for drug discovery. Accordingly, the supported amino acids of the invention are useful in the synthesis of large combinatorial libraries of peptides and other biologically active compounds which possess amino acid moieties of the present invention.

The templates of quaternary amino acids on solid supports of the present invention can be prepared using standard synthetic methods. For exemplary purposes, Schemes 1–7 illustrate general methods for the preparation of amino acid templates of the formula (1).

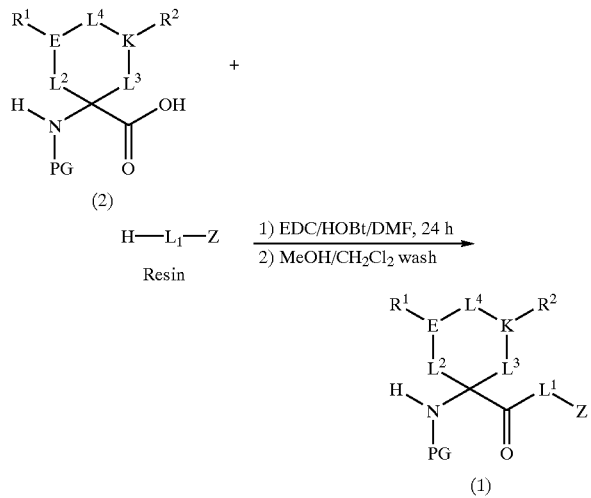

As shown in Scheme 1, compounds of the present invention can be prepared by adding a 3 to 5 fold excess of amino acids of formula (2) to mixture of an appropriate resin, EDC, and HOBt in DMF. The reaction mixture is agitated for over 24 h. The liquid phase is removed in vacuo followed by washings of the resin with methanol and dichloromethane to give resin-bound amino acids of formula (1).

As shown in Scheme 2, quaternary amino acids of formula (2a) containing a cyclopentene skeleton and an appropriate amino protecting group can be anchored to various resins via its carboxyl terminal. A quaternary amino acid of the formula (2a) is added to a polymeric support such as hydroxymethyl resin or aminomethyl, in a solution of EDC, HOBt, and TEA in DMF for 24 h. After shaking the reaction mixture for over 12 h, the mixture is washed with DMF, methanol, and dichloromethane to afford the desired resin-bound amino acid of formula (1aa).

DMF for 24 h. The reaction mixture is processed by removing unconsumed reactants and reagents in vacuo and washed sequentially with methanol, dichloromethane, ethyl acetate, and DMF. The resulting product is dried under vacuum to yield an amino acid of formula (1cc).

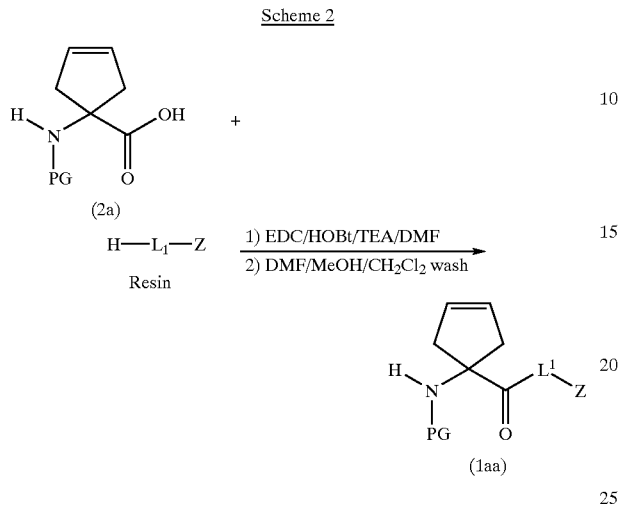

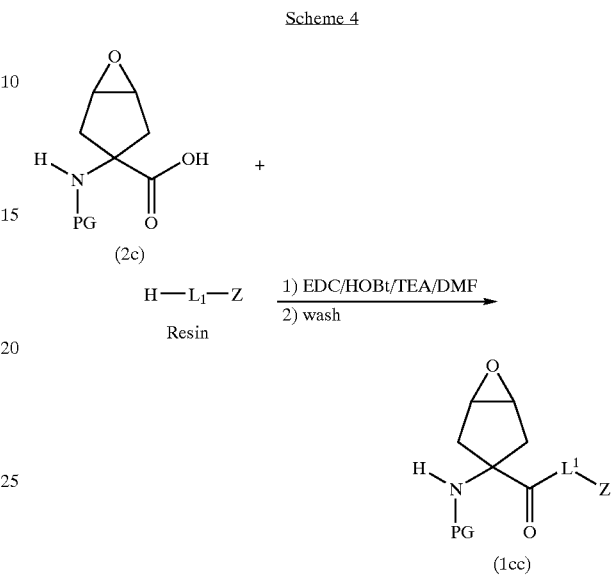

As shown in Scheme 3, trifunctionalized quaternary amino acid templates of formula (1 bb) can be prepared from the corresponding quaternary amino acid (2b) using the conditions described in Schemes 1 and 2. An amino acid of the formula (2b) is treated with the hydroxymethyl resin, wang resin, or aminomethyl resin, in the presence of EDC, HOBt, and TEA in DMF for 24 h. The reaction mixture is processed by removing unconsumed reactants and reagents in vacuo and washed sequentially with methanol, dichloromethane, ethyl acetate, and DMF. The resulting product is dried under vacuum to yield an amino acid of formula (1bb).

As shown in Scheme 5, protected diol containing amino acids of the formula (2d) can be treated with aminomethyl or hydroxymethyl resin and EDC/HOBt/TEA in DMF for over 24 h. The reaction mixture is processed by removing unconsumed reactants and reagents in vacuo and washed sequentially with DMF, methanol, ethyl acetate, and dichloromethane. The resulting product is dried under vacuum to yield an amino acid template of formula (1dd).

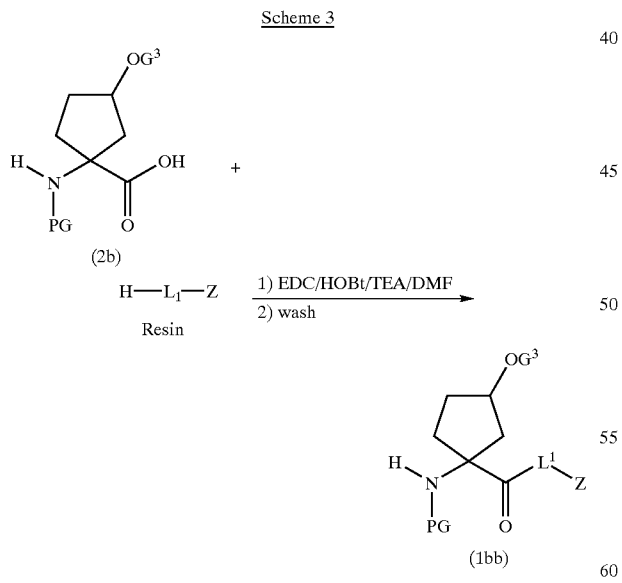

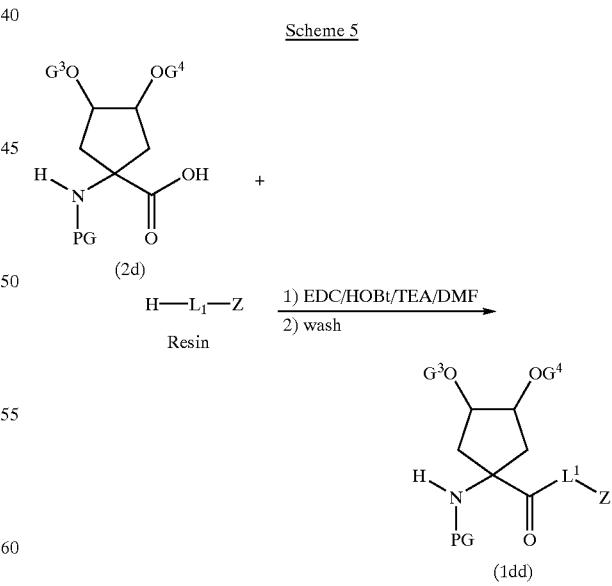

As shown in Scheme 4, epoxide containing amino acid derivatives of formula(2c) can be linked to an appropriate resin to give the amino acid template of formula (1cc) using similar reaction conditions as described above. An epoxide containing amino acid derivative of formula (2c) is treated with a resin in the presence of EDC, HOBt, and TEA in As shown in Scheme 6, highly functionalized amino acids of the formula (2e, where X comprises Cl, Br, I, or —S—$G^4$) can be converted to resin-supported amino acids of formula (1e) by treating the amino acid with EDC, HOBt, and TEA in DMF for over 24 h. The reaction mixture is processed by removing unconsumed reactants and reagents in vacuo and washed sequentially with DMF, methanol, ethyl acetate, and dichloromethane. The resulting product is dried under vacuum to yield an amino acid of formula (1ee).

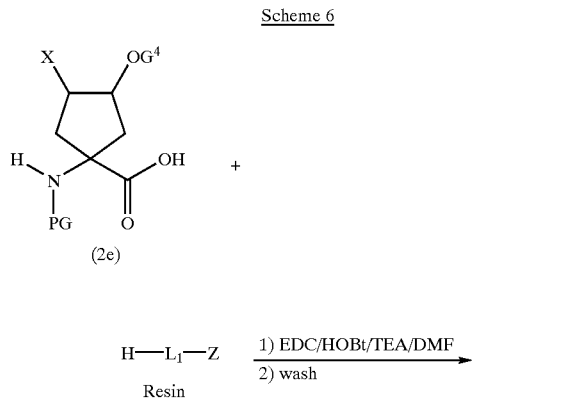

A general procedure for determining the load of amino acids on the Wang resin begins with 325 mg of Wang resin loaded with a quaternary amino acid The loaded resin is charged to a small round bottom flask and 10 ml of 1:1 TFA/CH$_2$Cl is added. The resulting mixture is stirred at ambient temp for 30 min and then the resin is filtered off and the filtrate is concentrated in vacuo and azeotroped with toluene (2×5 ml). $^1$H NMR analysis is used to reveal the amount of quaternary amino acid originally loaded onto the Wang resin.

Amino Acid derivatives (2f) can be treated with hydroxymethyl resin and aminomethyl resin to give the corresponding resin-bound products of the formula (1ff). In these reactants both the amino and the carboxy group must be protected appropriately to allow the reaction to proceed without the formation of any undesirable by-products.

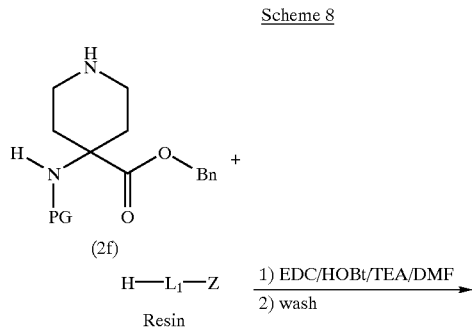

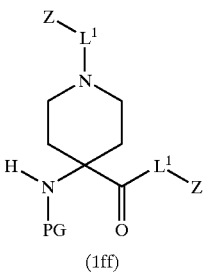

Procedures for determining the load of amino acids on other resins are readily apparent to those of ordinary skill in the art in light of the known general procedure for determining the load of amino acids on the Wang resin.

The quaternary amino acids of formula (2) are used to prepare the supported amino acid templates of the present invention. For example, quaternary amino acids of formula (2) can be prepared according to the general procedures outlined in Schemes 7 and 8.

In Scheme 7, an appropriate ketone, such as cyclohexanone, is reacted with an amino acid/chiral auxiliary or salt thereof, for example, phenyl alanine, and an appropriate convertible isocyanide such as those where R$^4$ is phenyl, cyclohexenyl, cyclohexyl, t-butyl, an amino protecting group, or the like. Solvents of the formula R$^5$OH include methanol, ethanol, or isopropanol, and reaction temperature conditions may be from about 80° to about 220° C. In turn, after cleavage of both the chiral auxiliary amine and the amide portions, the amino acids of formula (2) are provided. Specific examples of the synthesis of quaternary amino acids using this general procedure are described below.

Scheme 8

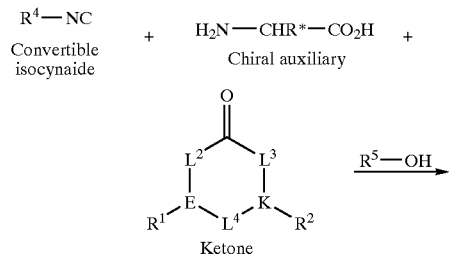

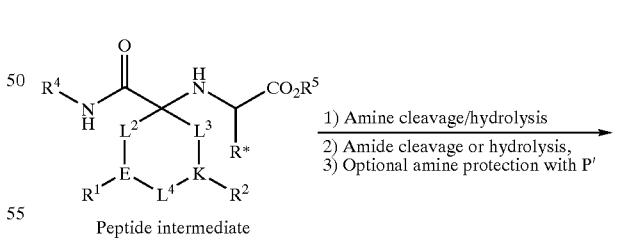

As shown in Scheme 8, amino acids of formula (2) can also be prepared using another general procedure. In Scheme 8, an appropriate dibromoalkanol, such as 1,4-dibromo-2-butanol (3), is protected with a THP group to yield THP protected dibromoalkanol (4). Next, to a suspension of sodium hydride is added a solution of N-(diphenylmethylene) glycine ethyl ester and the THP protected dibromoalkanol (4). After a standard work-up of the reaction mixture, the THP group is removed, and an intermediate quaternary amino ester (5) is obtained.

and HOBt (4 eq.). The resulting mixture was shaken for 24 h. The reaction mixture was then filtered in vacuum to remove reagents and solvents. The remaining resin was washed sequentially by DMF, MeOH, and DCM to yield the resin-bound 4-N-Fmoc-amino-4-carboxytetrahydropyran.

Example 2

The following example illustrates the synthesis of 4-Boc-amino-4-carboxytetrahydropyran Merrifield resin of the present invention.

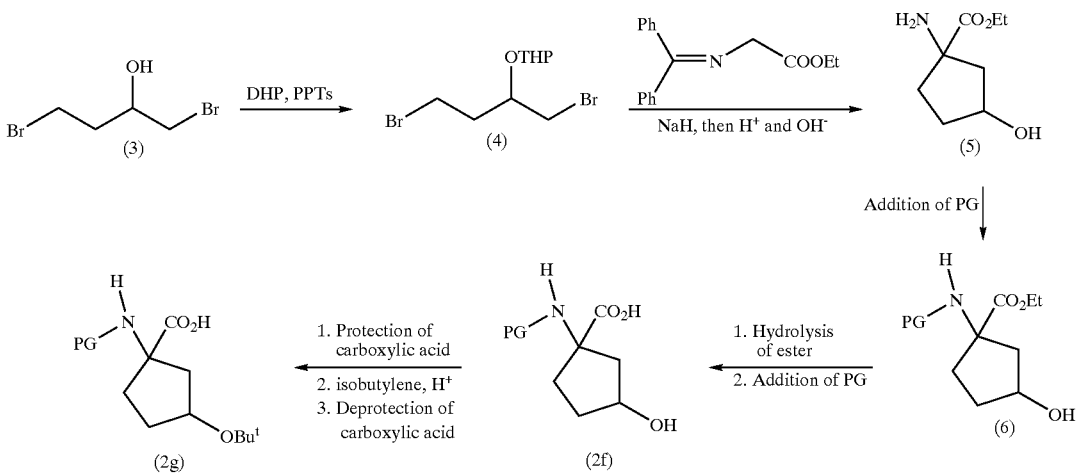

Scheme 9

The intermediate quaternary amino ester (5) is protected with an amino protecting group to yield a protected quaternary amino ester (6). After isolation of the protected quaternary amino ester (6), the ester group is hydrolyzed and the amino protecting group is removed. The free amine is protected again with an amino protecting group to yield a compound of formula (2f) which can be used to prepare the supported amino acid templates of the present invention.

The carboxylic acid of a compound of formula (2f) can be protected, followed by the addition of a tert-butyl group to the free alcohol and the removal of the carboxylic acid protecting group to yield a compound of formula (2g), which can be used to prepare the supported amino acid templates of the present invention.

EXAMPLES

Example 1

The following example illustrates the synthesis of 4-N-Fmoc-amino-4-carboxytetrahydropyran Merrifield resin of the present invention.

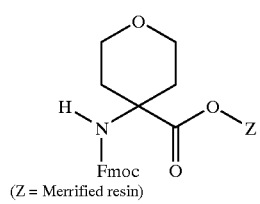
(Z = Merrified resin)

Hydroxymethyl resin (500 mg) was swollen in DMF and 4-N-Fmoc-amino-4-carboxytetrahydropyrane (4 eq.) was added followed by the addition of TEA (6 eq.), DCC (4 eq.), Hydroxymethyl resin (500 mg) was swollen in DMF and 4-Boc-amino-4-carboxytetrahydropyrane (4 eq.) was added followed by the addition of TEA (6 eq.), DCC or EDC (4 equiv), and HOBt (4 eq.). The resulting mixture was shaken for 24 h. The reaction mixture was then filtered in vacuum to remove reagents and solvents. The remaining resin was washed sequentially by DMF, MeOH, and DCM to yield the resin-bound 4-N-Boc-amino-4-carboxytetrahydrpyran.

Example 3

The following example illustrates the synthesis of 4-N-Fmoc-amino-4-N-carboxytetrahyrothiopyran Wang resin of the present invention.

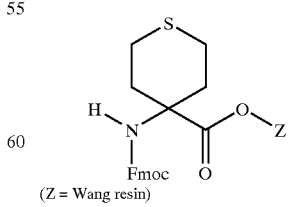
(Z = Wang resin)

Wang resin (500 mg) was swollen in DMF and 4-N-Fmoc-amino-4-N-carboxytetrahyrothiopyran (4 eq.) was added followed by the addition of TEA (6 eq.), DCC or EDC (4 equiv), and HOBt (4 eq.). The resulting mixture was shaken for 24 h. The reaction mixture was then filtered in vacuum to remove reagents and solvents. The remaining resin was washed sequentially by DMF, MeOH, and DCM to yield the resin-bound 4-N-Fmoc-amino-4-N-carboxytetrahyrothiopyran.

Example 4

The following example illustrates the synthesis of 4-N-Boc-amino-4-N-carboxytetrahyrothiopyran Wang resin of the present invention.

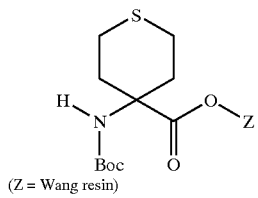
(Z = Wang resin)

Wang resin (500 mg) was swollen in DMF and 4-N-Boc-amino-4-N-carboxytetrahyrothiopyran (4 eq.) was added followed by the addition of TEA (6 eq.), DCC or EDC (4 equiv), and HOBt (4 eq.). The resulting mixture was shaken for 24 h. The reaction mixture was then filtered in vacuum to remove reagents and solvents. The remaining resin was washed sequentially by DMF, MeOH, and DCM to yield the resin-bound 4-N-Boc-amino-4-N-carboxytetrahyrothiopyran.

Example 5

The following example illustrates the synthesis of 4-N-Fmoc-amino-4-N-carboxy-1,1-dioxotetrahyrothiopyran Wang resin of the present invention.

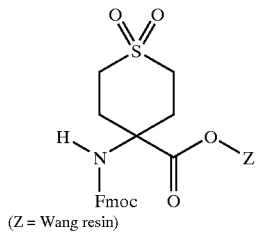
(Z = Wang resin)

Wang resin-bound 4-N-Fmoc-amino-4-N-carboxytetrahyrothiopyran (1g) was swollen in dichloromethane and treated with peracetic acid or m-chloroperbenzoic acid for 24 h. The reaction mixture was filtered in vacuo and then washed with DMF, MeOH, EtOAc and DCM to afford 4-N-Fmoc-amino-4-N-carboxy-1,1-dioxotetrahyrothiopyran Wang resin.

Example 6

The following example illustrates the synthesis of 4-N-Boc-amino-4-N-carboxy-1,1-dioxotetrahyrothiopyran Wang resin of the present invention.

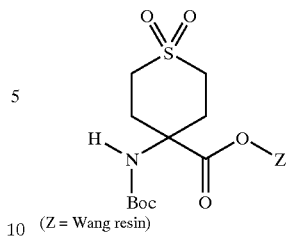
(Z = Wang resin)

Wang resin-bound 4-N-Boc-amino-4-N-Carboxytetrahyrothiopyran (1.2 g) was swollen in dichloromethane and treated with peracetic acid or m-chloroperbenzoic acid for 24 h. The reaction mixture was filtered in vacuo and then washed with DMF, MeOH, EtOAc and DCM to afford 4-N-Boc-amino-4-N-carboxy-1,1-dioxotetrahyrothiopyran Wang resin.

Example 7

The following example illustrates the synthesis 1-N-Boc-4(Fmoc-amino)piperidine-4 carboxylic acid Merrifield resin of the present invention.

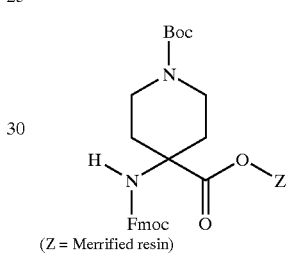
(Z = Merrified resin)

To a DMF suspension of hydroxymethyl resin was added 1-N-Boc-4-N-(Fmoc-amino)piperidine-4-carboxylic acid (500 mg), followed by TEA, DCC and HOBt. The mixture is shaken for 24 h. The solvent and unconsumed reagents were removed in vacuo. The crude product was then washed sequentially with DMF, MeOH, EtOAc and DCM to produce the resin-bound product.

Example 8

The following example illustrates the synthesis of 1-N-Boc-4-N-(Fmoc-amino)piperidine-4-carboxylic acid Wang resin of the present invention.

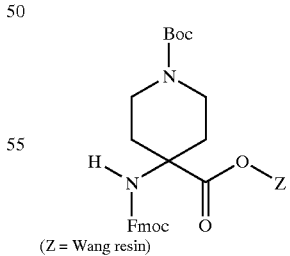
(Z = Wang resin)

A coated (SIGMACOTE®) vial was charged with Wang resin (1.0 g, 1.0 mmol active sites) followed by DMF (5 ml). Then, 1-Boc-4-N-(Fmoc-amino)piperidine-4-carboxylic acid (4.0 mmol) was dissolved in DMF (4 ml) and added to the resin/DMF followed by diisopropylcarbodiimide (0.613 ml, 4.0 mmol). Dimethylaminopyridine (0.122 g, 1.0 mmol)

was dissolved in DMF (1 ml) and added to the above mixture which was then placed on an orbital shaker for 16 hours at ambient temp. The resin was then filtered in a fritted syringe and washed with DMF followed by $CH_2Cl_2$ and MeOH (approximately 30 ml each). The resin was suspended during each wash cycle prior to filtration. The 1-N-Boc-4-N-(Fmoc-amino)piperidine-4-carboxylic acid Wang resin was dried in vacuo to a constant weight (40% loading typical).

Example 9

The following example illustrates the synthesis of 1-N-Fmoc-4-N-(Boc-amino)piperidine-4-carboxylic acid Merrifield resin of the present invention.

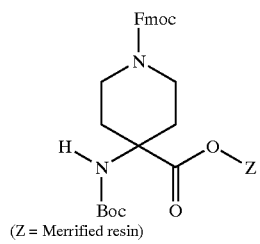

(Z = Merrified resin)

To 1-N-Fmoc-4-N-(Boc-amino)piperidine-4-carboxylic acid (5.0 mmol) in MeOH (24 ml) and water (2.4 ml) was added 20% aq. $Cs_2CO_3$ until pH 7. Volatiles were removed in vacuo. The residue was azeotroped with 1/1 MeOH/toluene (2×10 ml) and dried in vacuo to yield the Cesium salt of 1-N-Fmoc-4-N-(Boc-amino)piperidine-4-carboxylic acid.

A coated (SIGMACOTE®)vial was charged with Merrifield resin (2.0 g, 2.0 mmol active sites) and DMF (13 ml) followed by the Cesium salt of 1-N-Fmoc-4-N-(Boc-amino)piperidine-4-carboxylic acid (2.0 mmol). The mixture was placed in a 50° C. sand bath on an orbital shaker for 20 hours. The resin was then filtered in a fritted syringe and washed with DMF, 50% DMF/$H_2O$, 50% $H_2O$/MeOH, and MeOH (~40 ml each). The resin was suspended during each wash cycle prior to filtration. Drying in vacuo to a constant weight afforded 1-N-Fmoc-4-N-(Boc-amino)piperidine-4-carboxylic acid Merrifield resin. (30% loading typical).

Example 10

The following example illustrates the synthesis of N-Fmoc-amino-3-hydroxycyclopentyl carboxylic acid Merrifield resin of the present invention.

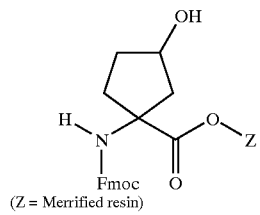

(Z = Merrified resin)

To N-Fmoc-amino-(3-hydroxycyclopentyl)carboxylic acid (5.0 mmol) in MeOH (24 ml) and water (2.4 ml) was added 20% aq. $Cs_2CO_3$ until pH 7. Volatiles were removed in vacuo. The residue was azeotroped with 1/1 MeOH/toluene (2×10 ml) and dried in vacuo to yield the Cesium salt of N-Fmoc-amino-(3-hydroxycyclopentyl)carboxylic acid.

A coated (SIGMACOTE®) vial was charged with Merrifield resin (2.0 g, 2.0 mmol active sites) and DMF (13 ml) followed by the Cesium salt of N-Fmoc-amino-(3-hydroxycyclopentyl)carboxylic acid (2.0 mmol). The mixture was placed in a 50° C. sand bath on an orbital shaker for 20 hours. The resin was then filtered in a fritted syringe and washed with DMF, 50% DMF/$H_2O$, 50% $H_2O$/MeOH, and MeOH (~40 ml each). The resin was suspended during each wash cycle prior to filtration. Drying in vacuo to a constant weight afforded N-Fmoc-amino-(3-hydroxy-cyclopentyl) carboxylic acid Merrifield resin. (30% loading typical).

Example 11

The following example illustrates the synthesis of N-Boc-amino-3-hydroxycyclopentyl-carboxylic acid Merrifield resin of the present invention.

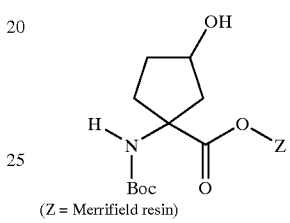

(Z = Merrifield resin)

The N-Boc-amino-(3-hydroxycyclopentyl)carboxylic acid (4 equiv) was added to a DMF suspension of the hydroxymethyl resin. To this mixture is added in 4–5 fold excess of morpholine, DCC, and HOBt. The resulting mixture was shaken for 24 h and then filtered under vacuum which is further washed successively with DMF, MeOH, EtOAc, and DCM under vacuum and the resulting product dried to afford N-Boc-amino-(3-hydroxycyclopentyl) carboxylic acid Merrifield resin.

Example 12

The following example illustrates the synthesis of N-Fmoc-amino-3-tert-butoxycyclopentyl-carboxylic acid Wang resin of the present invention.

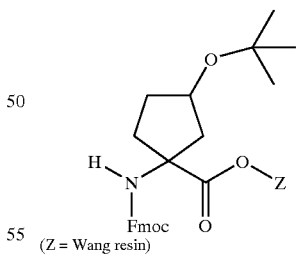

(Z = Wang resin)

The N-Fmoc-amino-3-tert-butoxycyclopentylcarboxylic acid (4 eq.) was added to a DMF suspension of Wang resin. To this mixture was added in 4-fold excess morpholine, DCC, and HOBt. The resulting mixture was shaken for 24 h and then filtered under vacuum to obtain the resin-bound product. It is washed successively with DMF, MeOH, EtOAc, and DCM under vacuum and the resulting product dried to afford N-Fmoc-amino-(3-tert-butoxycyclopentyl) carboxylic acid Wang resin.

Example 13

The following example illustrates the synthesis of 1-N-Fmoc-3-N-(Boc-amino)piperidine-3-carboxylic acid Merrifield resin of the present invention.

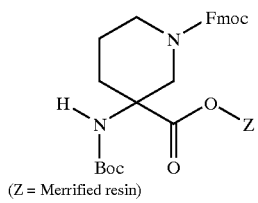

(Z = Merrified resin)

To 1-N-Fmoc-3-N-(Boc-amino)piperidine-3-carboxylic acid (5.0 mmol) in MeOH (24 ml) and water (2.4 ml) was added 20% aq. $Cs_2CO_3$ until pH 7. Volatiles were removed in vacuo. The residue was azeotroped with 1/1 MeOH/toluene (2×10 ml) and dried in vacuo to yield the Cesium salt of 1-N-Fmoc-4-N-(Boc-amino)piperidine-4-carboxylic acid.

A coated (SIGMACOTE®) vial was charged with Merrifield resin (2.0 g, 2.0 mmol active sites) and DMF (13 ml) followed by the Cesium salt of 1-N-Fmoc-3-N-(Boc-amino) piperidine-3-carboxylic acid (2.0 mmol). The mixture was placed in a 50° C. sand bath on an orbital shaker for 20 h. The resin was then filtered in a fritted syringe aid washed with DMF, 50% DMF/$H_2O$, 50% $H_2O$/MeOH, and MeOH (~40 ml each). The resin was suspended during each wash cycle prior to filtration. Drying in vacuo to a constant weight afforded 1-N-Fmoc-3-N-(Boc-amino)piperidine-3-carboxylic acid Merrifield resin. (30% loading typical).

Example 14

The following example illustrates the synthesis of 4-Hydroxy-1-N-Fmoc-amino-1-cyclohexylcarboxylic acid Merrified resin of the present invention.

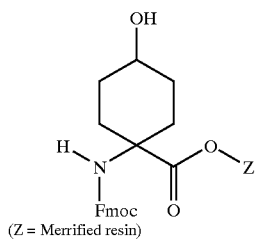

(Z = Merrified resin)

To 4-Hydroxy-1-N-Fmoc-amino-1-cyclohexylcarboxylic acid (5.0 mmol) in MeOH (24 ml) and water (2.4 ml) was added 20% aq. $Cs_2CO_3$ until pH 7. Volatiles were removed in vacuo. The residue was azeotroped with 1/1 MeOH/toluene (2×10 ml) and dried in vacuo to yield the Cesium salt of 4-Hydroxy-1-N-Fmoc-amino-1-cyclohexylcarboxylic acid.

A coated (SIGMACOTE®) vial was charged with Merrifield resin (2.0 g, 2.0 mmol active sites) and DMF (13 ml) followed by the Cesium salt of 4-Hydroxy-1-N-Fmoc-amino-1-cyclohexylcarboxylic acid (2.0 mmol). The mixture was placed in a 50° C. sand bath on an orbital shaker for 20 h. The resin was then filtered in a fritted syringe and washed with DMF, 50% DMF/$H_2O$, 50% $H_2O$/MeOH, and MeOH (~40 ml each). The resin was suspended during each wash cycle prior to filtration. Drying in vacuo to a constant weight afforded 4-Hydroxy-1-N-Fmoc-amino-1-cyclohexylcarboxylic acid Merrifield resin. (30% loading typical).

Example 15

The following example illustrates the synthesis of 4-Hydroxy-1-N-Fmoc-amino-1-cyclohexylcarboxylic acid Wang resin of the present invention.

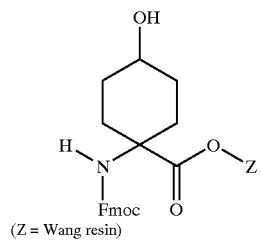

(Z = Wang resin)

A coated (SIGMACOTE®) vial was charged with Wang resin (1.0 g, 1.0 mmol active sites) followed by DMF (5 ml). Then, 4-Hydroxy-1-N-Fmoc-amino-1-cyclohexylcarboxylic acid (4.0 mmol) was dissolved in DMF (4 ml) and added to the resin/DMF followed by diisopropylcarboduimide (0.613 ml, 4.0 mmol). Dimethylaminopyridine (0.122 g, 1.0 mmol) was dissolved in DMF (1 ml) and added to the above mixture which was then placed on an orbital shaker for 16 h at ambient temp. The resin was then filtered in a fritted syringe and washed with DMF followed by $CH_2Cl_2$ and MeOH (approximately 30 ml each). The resin was suspended during each wash cycle prior to filtration. The 4-Hydroxy-1-N-Fmoc-amino-1-cyclohexylcarboxylic acid Wang resin was dried in vacuo to a constant weight (40% loading typical).

Example 16

The following example illustrates the synthesis of 4-tert-Butoxy-1-N-Fmoc-amino-1-cyclohexylcarboxylic acid Merrifield resin of the present invention.

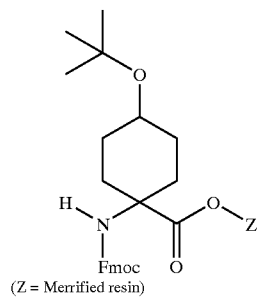

(Z = Merrified resin)

To 4-tert-Butoxy-1-N-Fmoc-amino-1-cyclohexylcarboxylic acid (5.0 mmol) in MeOH (24 ml) and water (2.4 ml) was added 20% aq. $Cs_2CO_3$ until pH 7. Volatiles were removed in vacuo. The residue was azeotroped with 1/1 MeOH/toluene (2×10 ml) and dried in vacuo to yield the Cesium salt of 4-tert-Butoxy-1-N-Fmoc-amino-1-cyclohexylcarboxylic acid.

A coated (SIGMACOTE®) vial was charged with Merrifield resin (2.0 g, 2.0 mmol active sites) and DMF (13 ml) followed by the Cesium salt of 4-tert-Butoxy-1-N-Fmoc-amino-1-cyclohexylcarboxylic acid (2.0 mmol). The mixture was placed in a 50° C. sand bath on an orbital shaker for 20 h. The resin was then filtered ina fritted syringe and washed with DMF, 50% DMF/H₂O, 50% H₂O/MeOH, and MeOH (~40 ml each). The resin was suspended during each wash cycle prior to filtration. Drying in vacuo to a constant weight afforded 4-tert-Butoxy-1-N-Fmoc-amino-1-cyclohexylcarboxylic acid Merrifield resin. (30% loading typical).

Example 17

The following example illustrates the synthesis of 4-tert-Butoxy-1-N-Fmoc-amino-1-cyclohexylcarboxylic acid Wang resin of the present invention.

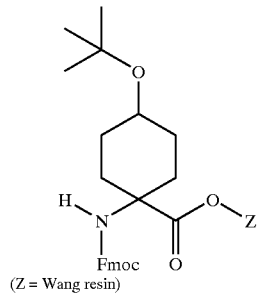
(Z = Wang resin)

A coated (SIGMACOTE®) vial was charged with Wang resin (1.0 g, 10 mmol active sites) followed by DMF (5 ml). Then, 4-tert-Butoxy-1-N-Fmoc-amino-1-cyclohexylcarboxylic acid (4.0 mmol) was dissolved in DMF (4 ml) and added to the resin/DMF followed by diisopropylcarbodiimide (0.613 ml, 4.0 mmol). Dimethylaminopyridine (0.122 g, 1.0 mmol) was dissolved in DMF (1 ml) and added to the above mixture which was then placed on an orbital shaker for 16 h at ambient temp. The resin was then filtered in a fritted syringe and washed with DMF followed by CH₂Cl₂ and MeOH (approximately 30 ml each). The resin was suspended during each wash cycle prior to filtration. The 4-tert-Butoxy-1-N-Fmoc-amino-1-cyclohexylcarboxylic acid Wang resin was dried in vacuo to a constant weight (40% loading typical).

Example 18

The following example illustrates the synthesis of N-Fmoc-aminocyclohexyl-carboxylate Merrifield resin of the present invention.

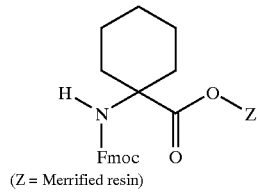
(Z = Merrified resin)

To N-Fmoc-aminocyclohexyl-carboxylic acid (5.0 mmol) in MeOH (24 ml) and water (2.4 ml) was added 20% aq. Cs₂CO₃ until pH 7. Volatiles were removed in vacuo and the residue was azeotroped with 1/1 MeOH/toluene (2×10 ml) and dried in vacuo.

A coated (SIGMACOTE®) vial was charged with Merrifield resin (2.0 g, 2.0 mmol active sites) and DMF (13 ml) followed by the above Cs salt (2.0 mmol). The mixture was placed in a 50° C. sand bath on an orbital shaker for 20 h. The resin was then filtered in a fritted syringe and washed with DMF, 50% DMF/H₂O, 50% H₂O/MeOH, and MeOH (~40 ml each). The resin was suspended during each wash cycle prior to filtration. Drying in vacuo to a constant weight afforded N-Fmoc-aminocyclohexylcarboxylate Merrifield resin (30% loading typical).

Example 19

The following example illustrates the synthesis of N-Fmoc-aminocyclohexyl-carboxylate Wang resin of the present invention.

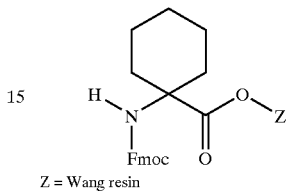
Z = Wang resin

A coated (SIGMACOTE®) vial was charged with Wang resin (1.0 g, 1.0 mmol active sites) followed by DMF (5 ml). The N-Fmoc-aminocyclohexylcarboxylic acid (4.0 mmol) was dissolved in DMF (4 ml) and added to the resin/DMF followed by diisopropylcarbodiimide (0.613 ml, 4.0 mmol). Dimethylamino pyridine (0.122 g, 1.0 mmol) was dissolved in DMF (1 ml) and added to the above mixture which was then placed on an orbital shaker for 16 h at ambient temp. The resin was then filtered in a fritted syringe and washed with DMF followed by CH₂Cl₂ and MeOH (~30 ml each). The resin was suspended during each wash cycle prior to filtration. The N-Fmoc-aminocyclohexyl-carboxylate Wang resin was dried in vacuo to a constant weight (40% loading typical).

Example 20

The following example illustrates the synthesis of N-Fmoc-amino-4-(ethyleneketal)cyclohexylcarboxylate Wang resin of the present invention.

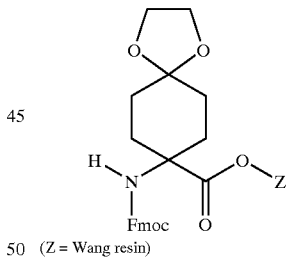
(Z = Wang resin)

A coated (SIGMACOTE®) vial was charged with Wang resin (1.0 g, 1.0 mmol active sites) followed by DMF (5 ml). The N-Fmoc-amino-4-(ethyleneketal)-cyclohexylcarboxylic acid (4.0 mmol) was dissolved in DMF (4 ml) and added to the resin/DMF followed by diisopropylcarbodiimide (0.613 ml, 4.0 mmol). Dimethylamino pyridine (0.122 g, 1.0 mmol) was dissolved in DMF (1 ml) and added to the above mixture which is then placed on an orbital shaker for 16 h at ambient temp. The resin was then filtered in a fritted syringe and washed with DMF followed by CH₂Cl₂ and MeOH (~30 ml each). The resin was suspended during each wash cycle prior to filtration. The resin was dried in vacuo to a constant weight to afford the N-Fmoc-amino-4-(ethyleneketal)cyclohexylcarboxylate Wang resin (40% loading typical).

Example 21

The following laboratory procedure illustrates the preparation of 4-N-Fmoc-amino-4-carboxytetrahydropyran.

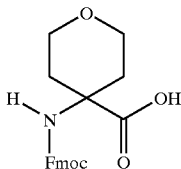

To the mixture of ammonia formate (18.95 g, 0.3 mole) in methanol (600 mL) was added tetrahydro-4H-pyran-4-on (14.96 g, 0.15 mole) and t-butyl isocyanide (14.93 g, 0.18 mole). The reaction mixture was refluxed for ~3 hr and solvent was evaporated. The crude product was used in the following hydrolysis reaction. MS (ESP+); m/z 229 (MH+). To the crude product was added 600 ml of 7 N HCl and the reaction mixture was stirred at reflux for ~3 h, then it was concentrated to half of its initial volume and left in the refrigerator for overnight. The solid 4-amino-4-carboxytetrahydropyran was filtered off thoroughly and washed with ethyl acetate, the aqueous part was concentrated again and more 4-amino-4-carboxytetrahydropyran was collected. Yield ~75%.

MS (ESP+): m/z 146 (MH+); $^1$H NMR (CD$_3$OD, 400 MHz, HCl salt): δ1.87 (m, 2H), 2.21 (m, 2H), 3.85 (m, 4H).

4-Amino-4-carboxytetrahydropyran hydrochloride (4.59 g, 25.3 mmole) was dissolved in a solution of dichloromethane (230 ml) and DIEA (17.69 ml, 101.2 mmole) was added. The reaction mixture was cooled to −10° C. and trimethylsilyl chloride (TMSCl, 7.06 ml, 55.7 mmole) was added, followed by addition of FmocCl (6.55 g, 25.3 mmole) at room temperature. The mixture was stirred overnight The solvent was distilled under vacuum, and the residue was treated with 2.5% sodium carbonate solution. After extraction with ethyl ether, the aqueous phase was acidified to pH 3 with 1 N HCl solution. After extraction with ethyl acetate, the organic solution was dried and evaporated to give 15 g (82%) of pure N-Fmoc-amino-carboxytetrahydropyran.

MS (ESP+) m/z 368.46 (MH+).

Example 22

The following laboratory procedure illustrates the preparation of 4-Boc-amino-4-carboxytetrahydropyran.

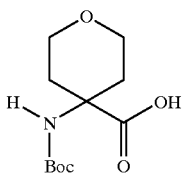

4-Amino-4-carboxytetrahydropyran hydrochloride (10 g, 55 mmole) was suspended in 1:1 dioxane/water mixture. Then 5 equiv of potassium carbonate was added, and the solution was cooled to 0° C. Then, 2.5 equivalents of di-tert-butyl-dicarbonate was added and the mixture stirred at room temperature for 48 hr. The reaction mixture was concentrated to half of its initial volume and extracted with hexane. The water phase was acidified to pH 3–4 with 1 N HCl solution. After extraction with ethyl acetate, the organic solution was dried and evaporated. Yield 3 g (22%).

MS (ESP+): m/z 246 (MH+); $^1$H NMR (CD$_3$OD, 300 MHz): 3.71 (m, 4H), 2.07 (m, 2H), 1.92 (m, 2H), 1.42 (m, 9H).

Example 23

The following laboratory procedure illustrates the preparation of 1-N-tert-butoxycarbonyl-4-(9-fluorenylmethoxycarbonyl amino)piperidine-4-carboxylic acid.

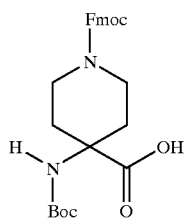

A 12 L round-bottom flask was equipped with a mechanical stirrer and charged with 500 g (3.25 mol) of 4-piperidone monohydrate hydrochloride, 685 g (6.99 mol) of ammonium carbonate, 4.2 L of methanol and 2.6 L of water. The mixture was allowed to stir at room temperature until all solids were dissolved. Then 443 g (6.82 mol) of potassium cyanide dissolved in 1.7 L water was added dropwise to the reaction mixture over a period of 15 minutes. The reaction was allowed to stir at room temperature for 48 h. The precipitated light yellow solid was collected in a Buchner funnel using suction filtration. This light yellow solid was washed with water until pure white (Note 2). The product was placed in a vacuum oven and dried under maximum vacuum at 80° C. This gave 440 g (80% yield) of the hydantoin.

Note, potassium cyanide is a potent poison and should always be handled carefully with gloves. Any exposure to acid releases highly toxic cyanide gas.

Also note, precipitated hydantoin must be washed with sufficient amounts of water to remove any residual ammonia, which can interfere with subsequent reactions. If ammonia odor or yellow color persists after initial water washes, additional washes should be performed.

A 12 L round-bottom flask was equipped with a mechanical stirrer and charged with 367 g (2.17 mol) of piperidine-4-spiro-5'-hydantoin, 6.0 L of 1,2-dimethoxyethane, and 221 g (2.17 mol) of triethylamine. This suspension was allowed to stir for 30 minutes. While stirring, 2368 g (10.9 mol) of solid di-tert-butyl dicarbonate was added to the reaction mixture, followed by 2.7 g (0.021 mol) of 4-dimethylaminopyridine (DMAP). A catalytic amount (2.7 g) of DMAP was added every 12 h during the course of the reaction. The reaction was allowed to stir vigorously for 72 h. During this period, the reaction becomes thicker. The precipitated yellow solid was collected in a Buchner funnel using suction filtration. The resulting yellow solid was triturated with 4 L of diethyl ether for 2 h. The solid was again collected in a Buchner funnel using suction filtration. The resulting light yellow solid was washed with 4 L of diethyl ether. The product was air dried overnight to give 910 g (87% yield) of the tri-Boc product.

$^1$H NMR (300 MHz; CDCl$_3$) δ4.29–4.01 (m, 2H), 3.57–3.42 (app dt, 2H), 2.67 (dt, 2H), 1.76 (m, 2H), 1.58 (s, 9H), 1.54 (s, 9H), 1.47 (s, 9H).

Note, triturating with diethyl ether was found necessary to successfully remove residual t-butyl carbonate anhydride and any t-butyl carbamate which may be produced as a result of residual traces of ammonia from the previous step.

A 12 L round-bottom flask was equipped with a mechanical stirrer and charged with 875 g (1.82 mol) of 1-tert-butyloxycarbonylpiperidine-4-spiro-5'-(1',3'-bis(tert-butyloxycarbonyl))hydantoin, followed by 4.8 L of tetrahydrofuran (THF). While stirring, 4.8 L of 3.0 M potassium hydroxide was added in one portion. The reaction mixture was allowed to stir for 48 h. The layers were separated and the bottom layer was drained into a round bottom flask. Residual THF was removed by rotary evaporation. The aqueous layer was then cooled to 4° C. and acidify slowly to pH 7 using a 6.0 M aqueous HCl solution. The resulting white precipitate is filtered, washed with water, and dried under vacuum at 70° C. This gave 421 g (96% yield) of the pure amino acid.

Note, the solution will become homogeneous and phase separate due to the heavy ionic content of the aqueous layer. Di-tert-butyl iminodicarboxylate, which is produced as a result of the hydrolysis, is selectively soluble in the THF layer, while the amino carboxylate salt of the product remains in solution in the aqueous layer.

Note, the temperature is not allowed to rise above 15° C. during the addition of the HCl solution. For each liter of aqueous solution, usually takes 400 mL of 6.0 M aqueous HCl solution to bring pH to 7.

A 12 L round-bottom flask was equipped with a mechanical stirrer and charged with 273 g (1.12 mol) of the amino acid, 394 g (3.72 mol) of sodium carbonate, 4 L of water, and 4 L of 1,4 dioxane. This suspension was allowed to stir for 30 minutes to become homogenous. While stirring, 317 g (1.23 mol) of 9-fluorenylmethylchloroformate was added in one portion. The solution was allowed to stir for 16 h (TLC (Ethyl Acetate: Hexane 8:2) Fmoc-Cl Rf=0.8, Product Rf=0.4, Starting Material Rf=0.0, Stain with PMA or Ninhydrin). The reaction was poured into 4 L water and extracted 2×3 L with diethyl ether. The aqueous layer was then acidified with 2 M aqueous HCl solution to pH 2 and the suspension was extracted 2×3 L with ethyl acetate. The combined organic layers were dried with sodium sulfate, filtered, and concentrated. The resulting sticky solid was triturated with hexanes followed by concentration. The resulting white solid was then removed from the flask and dried in vacuum at 40° C. This gave 400 g (77%) of the desired product.

$^1$H NMR (300 MHz, d$_6$-DMSO): δ7.88 (d, 2H), 7.71 (d, 2H), 7.62 (d, 1H), 7.39(t, 2H), 7.25 (t, 2H), 4.37 (m, 3H), 3.76 (m, 2H), 3.04 (m, 2H), 1.96 (m, 2H), 1.58 (m, 2H), 1.38 (s, 9H).

Example 24

The following laboratory procedure illustrates the preparation of N-Fmoc-amino-3-hydroxycyclopentyl-carboxylic acid.

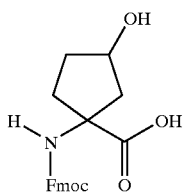

To a solution of 87 g (373 mmol) of 1,4-dibromo-2-butanol in dry dichloromethane (1500 mL) containing pyridinium p-toluenesulfonate (2.5 g, 3 mol %) was added 3,4-dihydro-2H-pyran (51 mL, 560 mmol, 1.5 eq) and the resulting mixture was stirred at room temperature for 5 h. Saturated sodium bicarbonate solution (300 mL) was added and the organic layer was separated from the aqueous one. The organic solution was washed with water (500 mL), saturated sodium chloride solution (500 mL), and dried over anhydrous sodium sulfate. After solvent removal, 118 grams (100%) of a light brownish oil was obtained which was used for the next step without further purification.

$^1$H-NMR (300 MHz, CDCl$_3$) δΔ4.71 (bs, 1H), 4.10–3.30 (m, 7H), 2.37–2.05 (m,2H). 1.90–1.40 (m, 6H).

To a suspension of sodium hydride (33.0 g, 820 mmol) in anhydrous THF (1000 mL) was added dropwise a solution of N-(diphenylmethylene)glycine ethyl ester (100 g, 373 mmol) in anhydrous THF (300 mL) under nitrogen and the resulting mixture was stirred at room temperature for 30 min. A solution of 2-tetrahydropyranyl-1,4-dibromo-2-butanol (118 g, 373 mmol) in anhydrous THF (100 mL) was added and the resulting mixture was stirred at room temperature for 2 h and then at reflux for 4 h. The reaction was cooled down to 0° C. using an ice bath and 1000 ml of 2.5N aqueous HCl solution was added. The resulting mixture was stirred at room temperature overnight. Ether (500 mL) was added and the aqueous layer was separated from the organic one. The aqueous solution was extracted with ether (2×500 mL) and then basified to pH 7 using sodium bicarbonate. Sodium bicarbonate (1.5 mole, 4.0 eq) was then added to the aqueous solution followed by the addition of a solution of Fmoc-OSu (150 g, 450 mmol, 1.2 eq) in 1,4-dioxane (1000 mL) and the resulting mixture was stirred at room temperature overnight. Dioxane was removed using rotary evaporation and the aqueous solution was extracted with ether (3×500 mL). The aqueous solution was acidified to pH 3 using 2 Naqueous HCl and the product was extracted with ethyl acetate (3×500 mL). The combined organic extracts were washed with saturated sodium chloride solution (500 mL) and dried over anhydrous sodium sulfate. After solvent removal, 118 g (80%) of the desired product was obtained.

$^1$H-NMR (300 MHz, CDCl$_3$) δ7.80–7.10 (m, 8H), 6.08 (bs, 1H), 4.60–3.90 (m, 5H,), 2.70–1.35 (m, 6H), 1.18 (t, 3H,J=7.5 Hz).

To a solution of N-Fmoc-amino-(3-hydroxy-cyclopentyl) carboxylic acid ethyl ester (59 g, 149 mmol) in THF (300 mL) was added a solution of lithium hydroxide monohydrate (18.8 g, 447 mmol, 3.0 eq) in water (300 mL) and the resulting mixture was stirred at room temperature overnight. Ether (100 mL) was added and the aqueous layer was separated from the organic one. The aqueous solution was extracted with ether (2×50 mL) and then basified to pH 7 using 2.0 N aqueous HCl. Sodium bicarbonate (596 mmol, 4.0 eq) was then added to the aqueous solution followed by the addition of a solution of Fmoc-Osu (60 g, 180 mmol, 1.2 eq) in 1,4-dioxane (300 mL) and the resulting mixture was stirred at room temperature overnight. Dioxane was removed using rotary evaporation and the aqueous solution was extracted with ether (3×100 mL). The aqueous solution was acidified to pH 3 using 2 N aqueous HCl and the product was extracted with ethyl acetate (3×100 mL). The combined organic extracts were washed with saturated sodium chloride solution (100 mL) and dried over anhydrous sodium sulfate. After solvent removal, 46 g (85%) of the desired product was obtained.

$^1$H-NMR (300 MHz, DMSO)δ12.25 (bs, 1H 7.90–7.25 (m, 8H), 7.65 (s, 1H), 4.10–4.30 (m, 3H), 2.50–1.40 (m, 6H).

MS calculated for $C_{21}H_{21}NO_5$ 368 (M+H), found 368.

Example 25

The following laboratory procedure illustrates the preparation of N-Boc-amino-3-hydroxycyclopentyl-carboxylic acid.

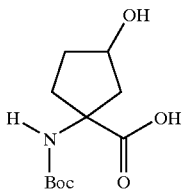

To a solution of N-Fmoc-amino-(3-hydroxycyclopentyl) carboxylic acid ethyl ester (11.3 g, 28.72 mmol) in THF (50 mL) was added a solution of lithium hydroxide monohydrate (3.6 g, 86.16 mmol, 3.0 eq) in water (50 ml) and the resulting mixture was stirred at room temperature overnight. Ether (100 mL) and water (100 mL) were added and the aqueous layer was separated from the organic phase. The aqueous solution was extracted with ether (2×50 mL) and then basified to pH 7 using 2.0N aqueous HCl. Potassium carbonate (144 mmol, 5.0 eq) was then added to the aqueous solution followed by the addition of a solution of $Boc_2O$ (15.7 g, 71.8 mmol, 2.5 eq) in 1,4-dioxane (150 mL) and the resulting mixture was stirred at room temperature for 2 days. Dioxane was removed using rotary evaporation and the aqueous solution was extracted with ether (3×50 mL). The aqueous solution was acidified to pH 3 using 2N HCl and the product was extracted with ethyl acetate (6×50 mL). The combined organic extracts were then dried over anhydrous sodium sulfate. After solvent removal, 2.5 g (36%) of the desired product was obtained.

$^1$ H-NMR (300 MHz, DMSO)δ7.18 (bs, 1H), 4.65 (bs, 1H), 4.10 (m, 2H), 2.50–1.40 (m, 6H), 1.30(s, 9H).

To a solution of N-Fmoc-amino-(3-hydroxy-cyclopentyl) carboxylic acid (271 mg, 0.74 mmol) in DMF (5.0 mL) were added N,N-diisopropylethylamine (0.13 mL, 1.0 eq), catalytic amount of sodium iodide, and benzyl bromide (0.11 mL, 1.2 eq) at room temperature. The resulting mixture was stirred at room temperature overnight. Water (15 mL) was added and the product was extracted with ethyl acetate (3×50 mL). The combined organic extracts were washed with saturated sodium chloride solution (50 mL) and dried over anhydrous sodium sulfate. The solvent was removed using rotary evaporation and the crude product was purified by flash column chromatography (hexane/ethyl acetate, 1/1) to yield the desired product in quantitative yield.

$^1$H-NMR (300 MHz, CDCl$_3$) δ 7.80–7.20 (m, 13H), 5.55 (bs, 1H), 5.18 (s, 2H), 4.50–4.25 (m, 2H), 4.22–4.10 (m, 1H), 2.60–1.70 (m, 6H).

A solution of N-Fmoc-amino-(3-hydroxycyclopentyl) carboxylic acid benzyl ester (338 mg, 0.74 mmol) in dry dichloromethane (10 mL) was cooled to −78° C. To this solution was added phosphoric acid (0.05 mL, prepared by dissolving 4.0 g of $P_2O_5$ in 11.0 mL of 85% $H_3PO_4$) and boron trifluoride diethyl etherate (0.1 mL) and isobutylene (10 mL). The mixture was allowed to warm up gradually to room temperature with stirring. Saturated sodium bicarbonate (10 mL) and ethyl acetate (25 mL) were added and the organic layer was separated from the aqueous layer. The aqueous layer was extracted with ethyl acetate (10 mL) and the combined organic extracts were washed with saturated sodium chloride solution and dried over anhydrous sodium sulfate. The solvent was removed using rotary evaporator and the crude product was purified using flash column chromatography (hexane/ethyl acetate, 4/1) to yield 370 mg (98%) of the desired product.

$^1$H-NMR (300 MHz, CDCl$_3$) δ7.80–7.20 (m, 13H), 5.90 (bs, 1H), 5.18 (s, 2H), 4.40–4.10 (m, 3H), 2.40–1.75 (m, 6H), 1.18 (s, 9H).

A solution of N-Fmoc-amino-3-tert-butoxy-cyclopentylcarboxylic acid benzyl ester (20 g, 39 mmol) in anhydrous ethanol (1000 mL) containing 1.0 g of 10 wt % palladium on activated carbon was stirred at room temperature for 4 h under hydrogen using a hydrogen balloon. The palladium catalyst was removed by passing through celite and the ethanol solution was further decolorized by passing through a short path of silica gel (230–400 mesh). The solvent was removed in vacuo. After drying under vacuum overnight, 18 g (97%) of the desired product was obtained.

$^1$H-NMR (300 MHz, DMSO) δ7.90–7.25 (m, 9H), 4.30–4.05 (m, 3H), 2.50–1.30(m,6H) 1.18 (s, 9H). MS calcd for $C_{25}H_{29}NO_5$ 424 (M+H), found 424.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or the scope of the appended claims.

We claim:

1. A compound of the following formula

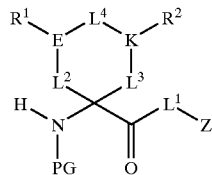

wherein

Z comprises the residue of a solid polymer support having hydroxyl or amino functionality;

$L^1$ comprises a divalent group of the formula —O—, —NH—, —O—CH$_2$—C$_6$H$_4$—CH$_2$O—;

$L^2$ and $L^3$ comprise, independently, alkylene, alkenylene, alkynylene, or a direct single bond;

$L_4$ comprises alkylene, —O—, —S—, —C(O)—, —S(O)—, —S(O)$_2$—,

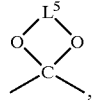

or a direct single or double bond;

$L^5$ comprises —CH$_2$CH$_2$— or —CH$_2$CH$_2$CH$_2$—;

E and K comprise, independently, —N—, —CH—, or —C═;

PG comprises hydrogen or an amino protecting group;

$R^1$ and $R^2$ comprise, independently, alkyl, alkenyl, alkynyl, cycloalkyl, heterocyclyl, aryl, heteroaryl, hydrogen, halo, —O—G$^3$, —O—G$^4$, —G$^3$, —G$^4$, or —N(G$^3$)G$^4$;

$R^1$ and $R^2$ may be taken together to constitute a cycloalkyl or heterocyclyl ring, or, where $L^4$ is a direct bond, $R^1$ and $R^2$ may be taken together to constitute a fused aryl or heteroaryl ring;

$G^3$ and $G^4$ comprise, independently,

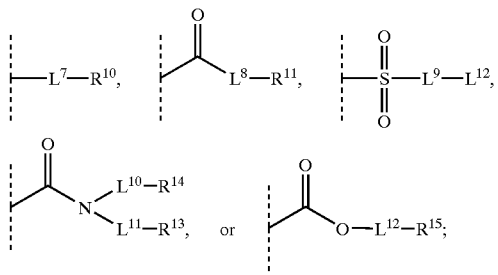

where $L^7$, $L^8$, $L^9$, $L^{10}$, $L^{11}$, $L^{12}$ comprise, independently, alkylene, alkenylene, alkynylene, cycloalkylene, cycloalkenylene, arylene, heterocyclylene, heteroarylene, fused cycloalkylarylene, fused cycloakylheteroarylene, fused heterocyclylarylene, fused heterocyclylheteroarylene, or a direct bond; and $R^{10}$, $R^{11}$, $R^{12}$, $R^{13}$, $R^{14}$, $R^{15}$ comprise, independently, alkyl, alkenyl, alkynyl, cycloalkyl, cycloalkenyl, heterocyclyl, heteroaryl, aryl, fused cycloalkylaryl, fused cycloakylheteroaryl, fused heterocyclylaryl, fused heterocyclylheteroaryl, —NR$^{18}$R$^{19}$, —OR$^{18}$, —SR$^{18}$, or hydrogen, where R$^{18}$ and R$^{19}$ are as defined below;

$R^{18}$ and $R^{19}$ comprise, independently, hydrogen, alkyl, alkynyl, alkenyl, cycloalkyl, cycloalkenyl, aryl, heterocyclyl, or heteroaryl.

2. The compound of claim 1, wherein the groups $L^2$, $L^3$, $L^4$, E, and K comprise a ring with 3 to 8 members.

3. The compound of claim 2, wherein PG is selected from the group consisting of t-butoxycarbonyl, 9-fluorenylmethoxycarbonyl, and benzyloxycarbonyl.

4. The compound of claim 2, wherein E and K are —CH—, represented by the formula

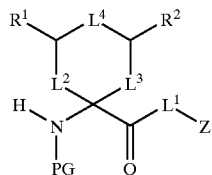

and wherein, $L^2$ and $L^3$ comprise, independently, —CH$^2$—, —CH$_2$CH$_2$—, or a direct single bond;

$L^4$ comprises —CH$_2$—, —C(O)—,

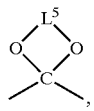

or a direct single bond;

$L^5$ comprises —CH$_2$CH$_2$— or —CH$_2$CH$_2$CH$_2$—;

$R^1$ and $R^2$ comprises, independently, alkyl, alkenyl, alkynyl, cycloalkyl, heterocyclyl, aryl, heteroaryl, hydrogen, halo, —O—G$^3$, —O—G$^4$, —G$^3$, —G$^4$, or —N(G$^3$)G$^4$;

$R^1$ and $R^2$ may be taken together to constitute a cycloalkyl or heterocyclyl ring;

$G^3$ and $G^4$ comprise, independently,

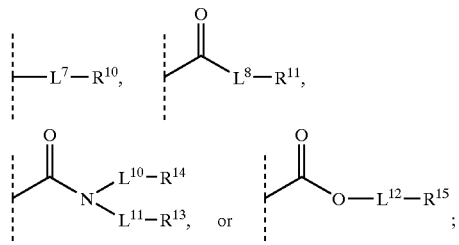

where $L^7$, $L^8$, $L^{10}$, $L^{11}$, $L^{12}$ comprise, independently, alkylene, alkenylene, alkynylene, cycloalkylene, cycloalkenylene, arylene, heterocyclylene, heteroarylene, fused cycloalkylarylene, fused cycloakylheteroarylene, fused heterocyclylarylene, fused heterocyclylheteroarylene, or a direct bond; and $R^{10}$, $R^{11}$, $R^{13}$, $R^{14}$, $R^{15}$ comprise, independently, alkyl, alkenyl, alkynyl, cycloalkyl, cycloalkenyl, heterocyclyl, heteroaryl, aryl, fused cycloalkylaryl, fused cycloakylheteroaryl, fused heterocyclylaryl, fused heterocyclylheteroaryl, —NR$^{18}$R$^{19}$, —OR$^{18}$, —SR$^{18}$, or hydrogen, where R$^{18}$ and R$^{19}$ are as defined below;

$R^{18}$ and $R^{19}$ comprise, independently, hydrogen, alkyl, alkynyl, alkenyl, cycloalkyl, cycloalkenyl, aryl, heterocyclyl, or heteroaryl.

5. The compound of claim 4 of the formula

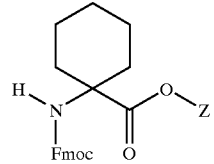

wherein Z comprises the Wang resin.

6. The compound of claim 4 of the formula

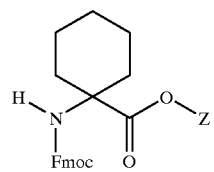

wherein Z comprises the Merrifield resin.

7. The compound of claim 4 of the formula

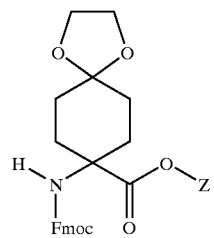

wherein Z comprises the Wang resin.

8. The compound of claim 4 of the formula

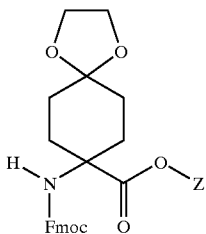

wherein Z comprises the Merrifield resin.

9. The compound of claim 4 of the formula

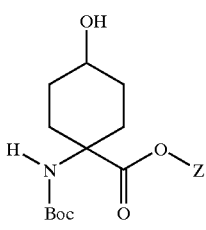

wherein Z comprises the Wang resin.

10. The compound of claim 4 of the formula

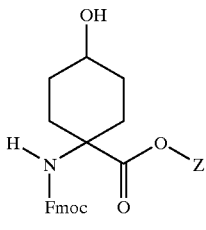

wherein Z comprises the Wang resin.

11. The compound of claim 4 of the formula

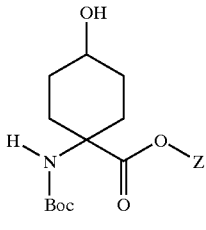

wherein Z comprises the Merrifield resin.

12. The compound of claim 4 of the formula

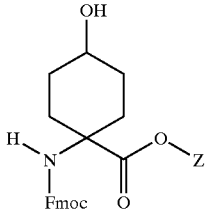

wherein Z comprises the Merrifield resin.

13. The compound of claim 4 of the formula

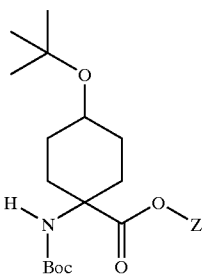

wherein Z comprises the Wang resin.

14. The compound of claim 4 of the formula

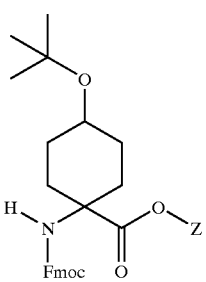

wherein Z comprises the Wang resin.

15. The compound of claim 4 of the formula

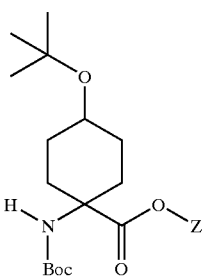

wherein Z comprises the Merrifield resin.

16. The compound of claim 4 of the formula

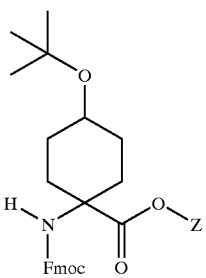

wherein Z comprises the Merrifield resin.

17. The compound of claim 4 of the formula

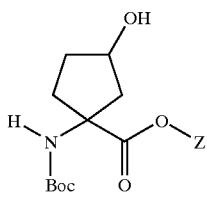

wherein Z comprises the Wang resin.

18. The compound of claim 4 of the formula

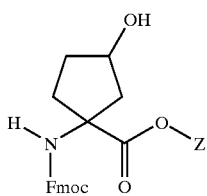

wherein Z comprises the Wang resin.

19. The compound of claim 4 of the formula

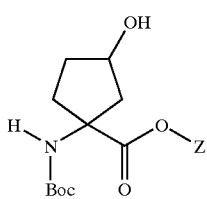

wherein Z comprises the Merrifield resin.

20. The compound of claim 4 of the formula

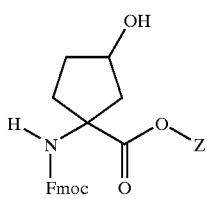

wherein Z comprises the Merrifield resin.

21. The compound of claim 4 of the formula

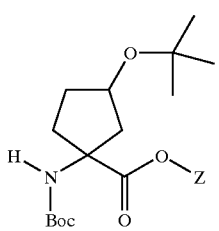

wherein Z comprises the Wang resin.

22. The compound of claim 4 of the formula

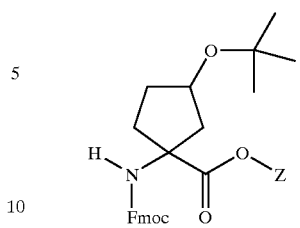

wherein Z comprises the Wang resin.

23. The compound of claim 4 of the formula

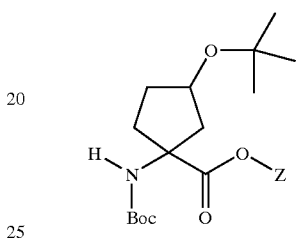

wherein Z comprises the Merrifield resin.

24. The compound of claim 4 of the formula

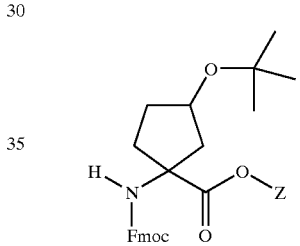

wherein Z comprises the Merrifield resin.

25. The compound of claim 4 of the formula

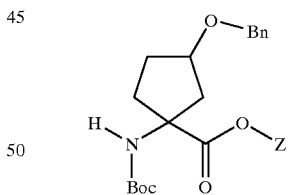

wherein Z comprises the Wang resin.

26. The compound of claim 4 of the formula

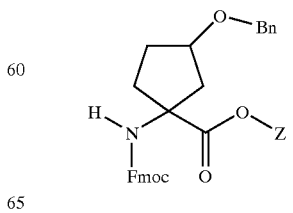

wherein Z comprises the Wang resin.

27. The compound of claim 4 of the formula

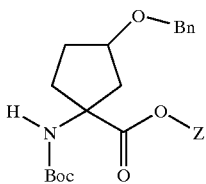

wherein Z comprises the Merrifield resin.

28. The compound of claim 4 of the formula

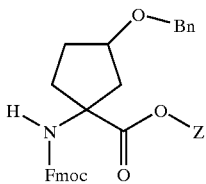

wherein Z comprises the Merrifield resin.

29. The compound of claim 2, wherein E and K are —CH—, represented by the formula

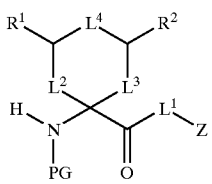

and wherein,
  $L^2$ and $L^3$ comprise, independently, —CH$_2$—, —CH$_2$CH$_2$—, or a direct single bond;
  $L^4$ comprises —O—, —S—, —S(O)—, or —S(O)$_2$—;
  $R^1$ and $R^2$ comprise, independently, alkyl, alkenyl, alkynyl, cycloalkyl, heterocyclyl, aryl, heteroaryl, hydrogen, halo, —O—G$^3$, —O—G$^4$, —G$^3$, —G$^4$, or —N(G$^3$)G$^4$;
  $R^1$ and $R^2$ may be taken together to constitute a heterocyclyl ring;
  G$^3$ and G$_4$ comprise, independently,

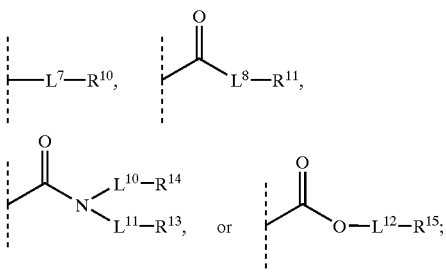

where
  $L^7$, $L^8$, $L^{10}$, $L^{11}$, $L^{12}$ comprise, independently, alkylene, alkenylene, alkynylene, cycloalkylene, cycloalkenylene, arylene, heterocyclylene, heteroarylene, fused cycloalkylarylene, fused cycloakylheteroarylene, fused heterocyclylarylene, fused heterocyclylheteroarylene, or a direct bond; and
  $R^{10}$, $R^{11}$, $R^{13}$, $R^{14}$, $R^{15}$ comprise, independently, alkyl, alkenyl, alkynyl, cycloalkyl, cycloalkenyl, heterocyclyl, heteroaryl, aryl, fused cycloalkylaryl, fused cycloakylheteroaryl, fused heterocyclylaryl, fused heterocyclylheteroaryl, —NR$^{18}$R$^{19}$, —OR$^{18}$, —SR$^{18}$, or hydrogen, where R$^{18}$ and R$^{19}$ are as defined below;

$R^{18}$ and $R^{19}$ comprise, independently, hydrogen, alkyl, alkynyl, alkenyl, cycloalkyl, cycloalkenyl, aryl, heterocyclyl, or heteroaryl.

30. The compound of claim 29 of the formula

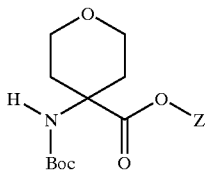

wherein Z comprises the Wang resin.

31. The compound of claim 29 of the formula

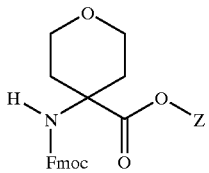

wherein Z comprises the Wang resin.

32. The compound of claim 29 of the formula

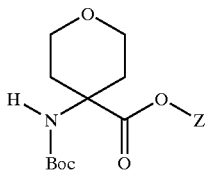

wherein Z comprises the Merrifield resin.

33. The compound of claim 29 of the formula

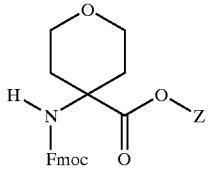

wherein Z comprises the Merrifield resin.

34. The compound of claim 29 of the formula

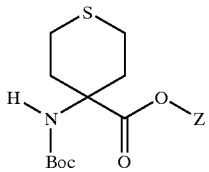

wherein Z comprises the Wang resin.

35. The compound of claim 29 of the formula

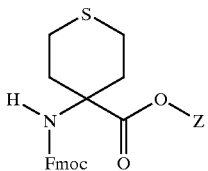

wherein Z comprises the Wang resin.

36. The compound of claim 29 of the formula

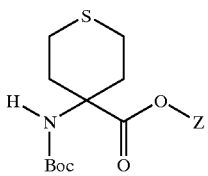

wherein Z comprises the Merrifield resin.

37. The compound of claim 29 of the formula

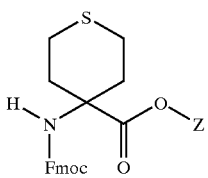

wherein Z comprises the Merrifield resin.

38. The compound of claim 29 of the formula

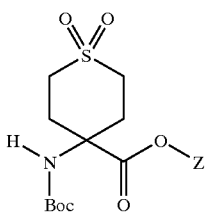

wherein Z comprises the Wang resin.

39. The compound of claim 29 of the formula

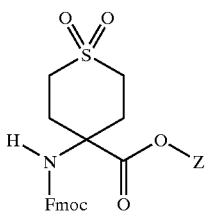

wherein Z comprises the Wang resin.

40. The compound of claim 29 of the formula

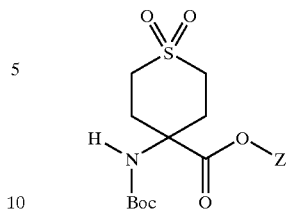

wherein Z comprises the Merrifield resin.

41. The compound of claim 29 of the formula

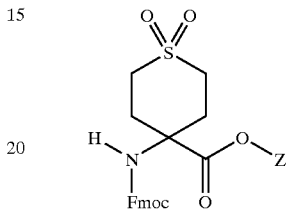

wherein Z comprises the Merrifield resin.

42. The compound of claim 2, wherein E comprises —CH—, K comprises —N—, $L^3$ comprises —CH$_2$CH$_2$—, $L^4$ comprises a direct single bond, represented by the formula

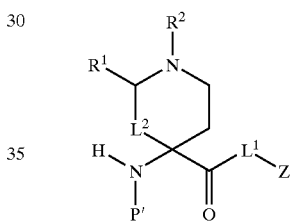

and wherein,
  $L^2$ comprises —CH$_2$—, —CH$_2$CH$_2$—, or a direct single bond;
  $R^1$ comprises alkyl, alkenyl, alkynyl, cycloalkyl, heterocyclyl, aryl, heteroaryl, hydrogen, halo, —O—$G^3$, —$G^3$, or —N($G^3$)$G^4$;
  $R^2$ comprises alkyl, alkenyl, alkynyl, cycloalkyl, heterocyclyl, aryl, heteroaryl, hydrogen, or —$G^5$;
  $R^1$ and $R^2$ may be taken together to constitute a heterocyclyl ring;
  $G^3$ and $G^4$ comprise, independently,

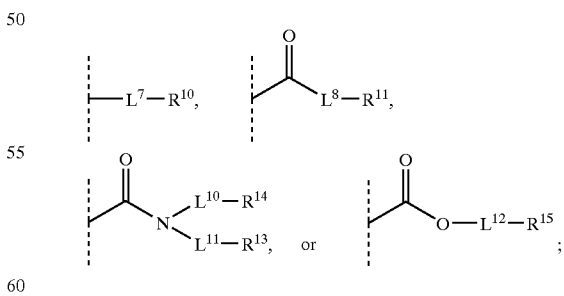

where
  $L^7$, $L^8$, $L^{10}$, $L^{11}$, $L^{12}$ comprise, independently, alkylene, alkenylene, alkynylene, cycloalkylene, cycloalkenylene, arylene, heterocyclylene, heteroarylene, fused cycloalkylarylene, fused cycloakylheteroarylene, fused heterocyclylarylene, fused heterocyclylheteroarylene, or a direct bond; and $R^{10}$, $R^{11}$, $R^{13}$, $R^{14}$, $R^{15}$ comprise, independently, alkyl, alkenyl, alkynyl, cycloalkyl, cycloalkenyl, heterocyclyl, heteroaryl, aryl, fused cycloalkylaryl, fused cycloakylheteroaryl, fused heterocyclylaryl, fused heterocyclylheteroaryl, —$NR^{18}R^{19}$, —$OR^{18}$, —$SR^{18}$, or hydrogen, where $R^{18}$ and $R^{19}$ are as defined below;

$R^{18}$ and $R^{19}$ comprise, independently, hydrogen, alkyl, alkynyl, alkenyl, cycloalkyl, cycloalkenyl, aryl, heterocyclyl, or heteroaryl;

$G^5$ comprises

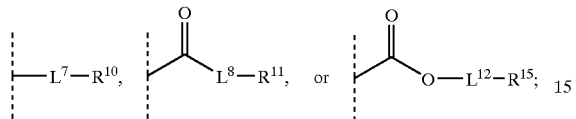

where $L^7$, $L^8$, $L^{12}$ comprise, independently, alkylene, alkenylene, alkynylene, cycloalkylene, cycloalkenylene, arylene, heterocyclylene, heteroarylene, fused cycloalkylarylene, fused cycloakylheteroarylene, fused heterocyclylarylene, fused heterocyclylheteroarylene, or a direct bond; and $R^{10}$, $R^{11}$, $R^{15}$ comprise, independently, alkyl, alkenyl, alkynyl, cycloalkyl, cycloalkenyl, heterocyclyl, heteroaryl, aryl, fused cycloalkylaryl, fused cycloakylheteroaryl, fused heterocyclylaryl, fused heterocyclylheteroaryl, —$NR^{18}R^{19}$, —$OR^{18}$, —$SR^{18}$, or hydrogen, where $R^{18}$ and $R^{19}$ are as defined below;

$R^{18}$ and $R^{19}$ comprise, independently, hydrogen, alkyl, alkynyl, alkenyl, cycloalkyl, cycloalkenyl, aryl, heterocyclyl, or heteroaryl.

43. The compound of claim 42 of the formula

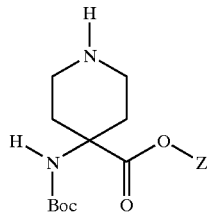

wherein Z comprises the Wang resin.

44. The compound of claim 42 of the formula

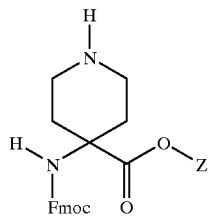

wherein Z comprises the Wang resin.

45. The compound of claim 42 of the formula

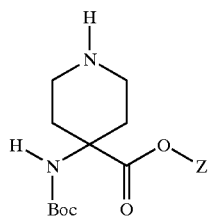

wherein Z comprises the Merrifield resin.

46. The compound of claim 42 of the formula

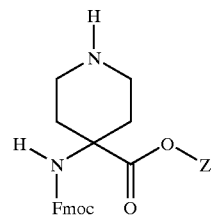

wherein Z comprises the Merrifield resin.

47. The compound of claim 42 of the formula

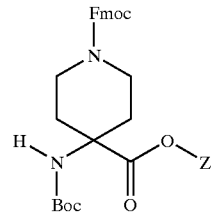

wherein Z comprises the Wang resin.

48. The compound of claim 42 of the formula

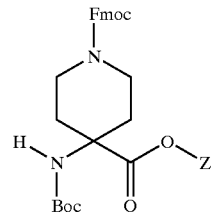

wherein Z comprises the Merrifield resin.

49. The compound of claim 42 of the formula

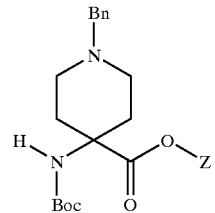

wherein Z comprises the Wang resin.

50. The compound of claim 42 of the formula

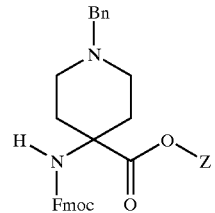

wherein Z comprises the Wang resin.

51. The compound of claim 42 of the formula

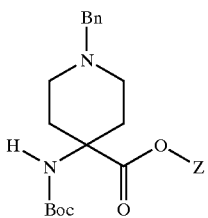

wherein Z comprises the Merrifield resin.

52. The compound of claim 42 of the formula

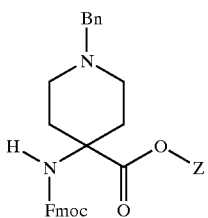

wherein Z comprises the Merrifield resin.

53. The compound of claim 42 of the formula

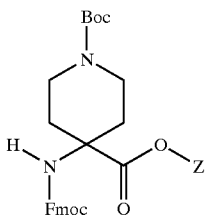

wherein Z comprises the Wang resin.

54. The compound of claim 42 of the formula

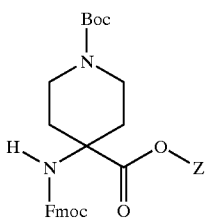

wherein Z comprises the Merrifield resin.

55. The compound of claim 2, wherein E comprises —CH—, K comprises —N—, $L^3$ comprises —CH$_2$—, $L^4$ comprises —CH$_2$—, represented by the formula

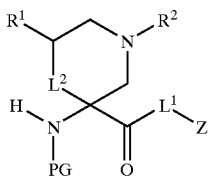

and wherein, $L^2$ comprises —CH$_2$—, —CH$_2$CH$_2$—, or a direct single bond;

$R^1$ comprises alkyl, alkenyl, alkynyl, cycloalkyl, heterocyclyl, aryl, heteroaryl, hydrogen, halo, —O—G$_3$, —G$^3$, or —N(G$_3$)G$_4$;

$R^2$ comprises alkyl, alkenyl, alkynyl, cycloalkyl, heterocyclyl, aryl, heteroaryl, hydrogen, or —G$^5$;

$R^1$ and $R^2$ may be taken together to constitute a heterocyclyl ring;

$G^3$ and $G^4$ comprise, independently,

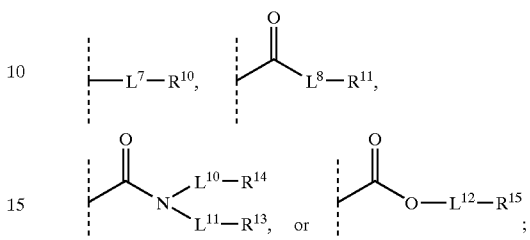

where $L^7, L^8, L^{10}, L^{11}, L^{12}$ comprise, independently, alkylene, alkenylene, alkynylene, cycloalkylene, cycloalkenylene, arylene, heterocyclylene, heteroarylene, fused cycloalkylarylene, fused cycloakylheteroarylene, fused heterocyclylarylene, fused heterocyclylheteroarylene, or a direct bond; and $R^{10}, R^{11}, R^{13}, R^{14}, R^{15}$ comprise, independently, alkyl, alkenyl, alkynyl, cycloalkyl, cycloalkenyl, heterocyclyl, heteroaryl, aryl, fused cycloalkylaryl, fused cycloakylheteroaryl, fused heterocyclylaryl, fused heterocyclylheteroaryl, —NR$^{18}$R$^{19}$, —OR$^{18}$, —SR$^{18}$, or hydrogen, where $R^{18}$ and $R^{19}$ are as defined below;

$R^{18}$ and $R^{19}$ comprise, independently, hydrogen, alkyl, alkynyl, alkenyl, cycloalkyl, cycloalkenyl, aryl, heterocyclyl, or heteroaryl, $G^5$ comprises

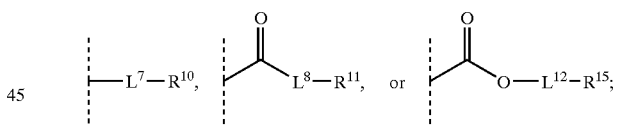

where $L^7, L^8, L^{12}$ are, independently, alkylene, alkenylene, alkynylene, cycloalkylene, cycloalkenylene, arylene, heterocyclylene, heteroarylene, fused cycloalkylarylene, fused cycloakylheteroarylene, fused heterocyclylarylene, fused heterocyclylheteroarylene, or a direct bond; and $R^{10}, R^{11}, R^{15}$ are, independently, alkyl, alkenyl, alkynyl, cycloalkyl, cycloalkenyl, heterocyclyl, heteroaryl, aryl, fused cycloalkylaryl, fused cycloakylheteroaryl, fused heterocyclylaryl, fused heterocyclylheteroaryl, —NR$^{18}$R$^{19}$, —OR$^{18}$, —SR$^{18}$, or hydrogen, where $R^{18}$ and $R^{19}$ are as defined below;

$R^{18}$ and $R^{19}$ are, independently, hydrogen, alkyl, alkynyl, alkenyl, cycloalkyl, cycloalkenyl, aryl, heterocyclyl, or heteroaryl.

56. The compound of claim 55 of the formula

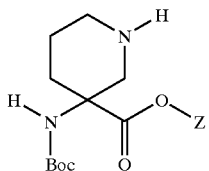

wherein Z comprises the Wang resin.

57. The compound of claim 55 of the formula

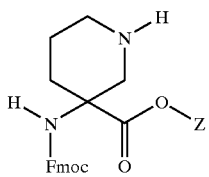

wherein Z comprises the Wang resin.

58. The compound of claim 55 of the formula

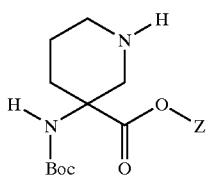

wherein Z comprises the Merrifield resin.

59. The compound of claim 55 of the formula

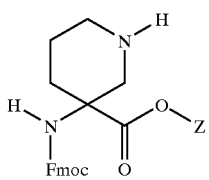

wherein Z comprises the Merrifield resin.

60. The compound of claim 55 of the formula

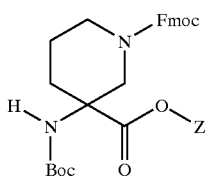

wherein Z comprises the Wang resin.

61. The compound of claim 55 of the formula

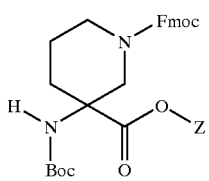

wherein Z comprises the Merrifield resin.

62. The compound of claim 55 of the formula

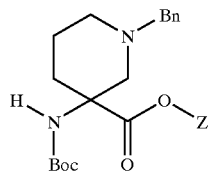

wherein Z comprises the Wang resin.

63. The compound of claim 55 of the formula

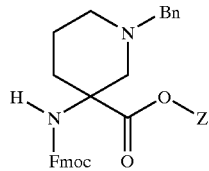

wherein Z comprises the Wang resin.

64. The compound of claim 55 of the formula

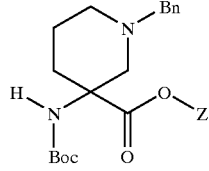

wherein Z comprises the Merrifield resin.

65. The compound of claim 55 of the formula

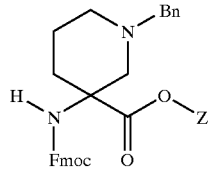

wherein Z comprises the Merrifield resin.

66. The compound of claim 55 of the formula

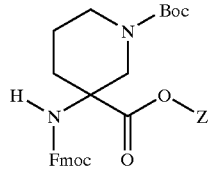

wherein Z comprises the Wang resin.

67. The compound of claim 55 of the formula

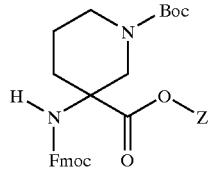

wherein Z comprises the Merrifield resin.

* * * * *